United States Patent

Pieper et al.

[11] Patent Number: 5,922,717
[45] Date of Patent: *Jul. 13, 1999

[54] PIPERAZINE DERIVATIVES, MEDICAMENTS COMPRISING THESE COMPOUNDS, THEIR USE AND PROCESSES FOR THEIR PREPARATION

[75] Inventors: Helmut Pieper; Volkhard Austel, both of Biberach; Frank Himmelsbach; Günter Linz, both of Mittelbiberach; Brian Guth, Warthausen; Johannes Weisenberger, Biberach, all of Germany

[73] Assignee: Dr. Karl Thomae GmbH, Biberach an der Riss, Germany

[*] Notice: This patent issued on a continued prosecution application filed under 37 CFR 1.53(d), and is subject to the twenty year patent term provisions of 35 U.S.C. 154(a)(2).

[21] Appl. No.: 08/576,528

[22] Filed: Dec. 21, 1995

[30] Foreign Application Priority Data

Dec. 23, 1994 [DE] Germany ............... 44 46 301
Jul. 21, 1995 [DE] Germany ............... 195 26 678
Sep. 12, 1995 [DE] Germany ............... 195 33 639

[51] Int. Cl.[6] ............ C07D 211/58; C07D 401/06; A61K 31/445; A61K 31/995
[52] U.S. Cl. ............ 514/252; 544/360; 544/364
[58] Field of Search ............ 544/360, 364; 514/252

[56] References Cited

U.S. PATENT DOCUMENTS 4,539,322  9/1985  Campbell et al. .................. 514/253
4,895,846  1/1990  Poindexter et al. ................ 514/252

FOREIGN PATENT DOCUMENTS 0024282   3/1981   European Pat. Off. .
074768 A2  3/1983  European Pat. Off. ...... C07D 213/74
210782    2/1987   European Pat. Off. ...... C07D 213/56
0483667   5/1992   European Pat. Off. .
0567966  11/1993   European Pat. Off. .
0612741   8/1994   European Pat. Off. .
0638553   2/1995   European Pat. Off. .
0639575   2/1995   European Pat. Off. .
721941    2/1996   European Pat. Off. ...... C07D 211/58
94/22834 10/1994   WIPO .................... C07D 213/74
94/22835 10/1994   WIPO .................... C07D 213/74
96/10022  4/1996   WIPO .................... C07D 401/04

*Primary Examiner*—José G. Dees
*Assistant Examiner*—Sabiha N. Qaz
*Attorney, Agent, or Firm*—R. P. Raymond; A. R. Stempel; M-E. M. Devlin

[57] ABSTRACT

The present invention relates to piperazine derivatives of the general formula

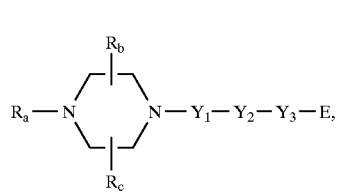

(I)

in which $R_a$, $Y_1$ to $Y_3$ and E are defined herein, tautomers thereof, stereoisomers thereof, including their mixtures, and salts thereof, and in particular physiologically tolerated salts thereof with inorganic or organic acids or bases. These compounds have valuable pharmacological properties, such as aggregation-inhibiting activity. This invention also relates to medicaments comprising these compounds and to processes for the preparation of these compounds.

6 Claims, No Drawings

PIPERAZINE DERIVATIVES, MEDICAMENTS COMPRISING THESE COMPOUNDS, THEIR USE AND PROCESSES FOR THEIR PREPARATION

The present invention relates to piperazine derivatives of the general formula

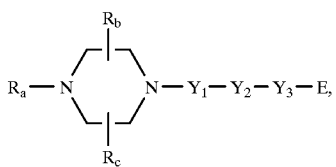

(I)

tautomers thereof, stereoisomers thereof, including their mixtures, and salts thereof, in particular salts thereof with physiologically tolerated acids or bases, which have valuable pharmacological properties, preferably aggregation-inhibiting actions, medicaments comprising these compounds and their use and to processes for their preparation.

In the above general formula I, $R_a$ is a 3-pyrrolidinyl, 3-piperidinyl, 4-piperidinyl, 3-hexamethyleniminyl or 4-hexamethyleniminyl group, where the hydrogen atom of the abovementioned alkylenimino rings can in each case be replaced by a $C_{1-5}$-alkyl or aryl-$C_{1-3}$-alkyl group, in which the alkyl part in each case can be substituted by a carboxyl, $C_{1-3}$-alkoxycarbonyl, aminocarbonyl, N-$C_{1-3}$-alkyl-aminocarbonyl, N,N-di-($C_{1-3}$-alkyl)-aminocarbonyl, vinyl or ethynyl group or else, if the abovementioned substituents are not on an a-carbon atom adjacent to a nitrogen atom, can be substituted by a hydroxyl, $C_{1-3}$-alkoxy, amino, $C_{1-3}$-alkylamino or di-($C_{1-3}$-alkyl) amino group, or can be replaced by a radical which can be split off in vivo, $R_b$ and $R_c$, which can be identical or different, are hydrogen atoms or $C_{1-5}$-alkyl, aryl or aryl-$C_{1-5}$-alkyl groups, or $R_b$ and $R_c$, together with the ethylene bridge in between, are an o-phenylene group, where one or two methylene groups in the 1,4-piperazinylene group of the above general formula I additionally in each case can be replaced by a carbonyl group, $Y_1$ is an —$A_1$—, —CO—, —CO—CO—, —$A_1$—CO—, —CO—$A_1$—, —$SO_2$—$A_2$—, —$A_2$—$SO_2$—, —CO—$A_1$—CO—, —CO—$NR_1$—CO—, —CO—$NR_1$—$A_2$—, —CO—$NR_1$—$A_2$—CO—, —CO—$A_2$—$NR_1$—CO—, —CO—$A_2$—O— or —CO—$A_2$—$NR_1$— group, in which $R_1$ is a hydrogen atom or a $C_{1-5}$-alkyl, aryl or aryl-$C_{1-3}$-alkyl group, $A_1$ is an n-$C_{1-5}$-alkylene group which is optionally substituted by a $C_{1-5}$-alkyl, cyclohexyl-$C_{1-3}$-alkyl, aryl or aryl-$C_{1-3}$-alkyl group, or else by an $R_1O$ group, if this is not in the α-position relative to a nitrogen atom, and $A_2$ is an n-$C_{1-4}$-alkylene group which is optionally substituted by a $C_{1-5}$-alkyl, aryl or aryl-$C_{1-3}$-alkyl group, $Y_2$ is a phenylene, cyclohexylene or pyridinylene group, a 3-piperidinylene, 4-piperidinylene or 1,4-piperazinylene group, in which a methylene group adjacent to a nitrogen atom in each case can be replaced by a carbonyl group, where a 4-piperidinylene group additionally can be substituted by an $R_1O$ group in the 4-position, with the proviso that no N,O— or O,O-acetal and no N,O or N,N bond is formed in the linkage with $Y_1$ or $Y_3$, a 1,4-ketopiperazinylene group, which can be substituted by a $C_{1-5}$-alkyl group in the a-position relative to the carbonyl group, where the alkyl group additionally can be substituted by a phenyl group which is optionally substituted by an $R_1O$ group, or by a $C_{1-3}$-alkoxycarbonyl or carboxyl group, or an —$NR_1$—B— or —O—B— group, where the linkage with the $Y_1$ group is effected via the nitrogen atom of the —$NR_1$— group or via the oxygen atom of the —O—B— group, in which $R_1$ is defined as above and B is a phenylene, cyclohexylene, piperidinylene or pyridinylene group, where the linkage of the piperidinylene group with the radical —$NR_1$— or with the oxygen atom in each case is effected via the 3- or 4-position and in which a methylene group adjacent to a nitrogen atom additionally can be replaced by a carbonyl group, $Y_3$ is a —CO—, —$A_2$—CO—, —$CH_2$—CH($NHR_2$)—CO—, —$NR_2$—$A_3$—CO—, —$CH_2$—$NR_2$—$A_3$—CO—, —O—$A_3$—CO—, —CO—$A_3$—CO— or —CO—$NR_1$—$A_3$—CO— group, in which $R_1$ and $A_2$ are defined as above, $A_3$ is an n-$C_{1-3}$-alkylene group which is optionally substituted by a $C_{1-5}$-alkyl, aryl, pyridyl or aryl-$C_{1-3}$-alkyl group and $R_2$ is a hydrogen atom, a $C_{1-5}$-alkyl, aryl-$C_{1-3}$-alkyl, aryl, $C_{1-5}$-alkoxycarbonyl, $C_{1-5}$-alkylsulphonyl, aryl-$C_{1-3}$-alkylsulphonyl or arylsulphonyl group, or a formyl group which is optionally substituted by a $C_{1-4}$-alkyl, aryl or aryl-$C_{1-3}$-alkyl group, and the linkage of the —$A_2$—CO— group with the radical $Y_2$ is effected via the radical $A_2$, that of the —$NR_2$—$A_3$—CO— group is effected via the $NR_2$ group and that of the —O—$A_3$—CO— group is effected via the oxygen atom, but where an —$NR_2$—$A_3$—CO—, —$CH_2$—$NR_2$—$A_3$—CO— or —O—$A_3$—CO— group cannot be linked with a nitrogen atom of the radical $Y_2$, and E is a hydroxyl group, an alkoxy group having 1 to 6 carbon atoms, a phenylalkoxy group, in which the alkoxy part can contain 1 to 3 carbon atoms, a cycloalkoxy group having 3 to 9 carbon atoms, in which the cycloalkyl part having 5 to 8 carbon atoms additionally can be substituted by one or two alkyl groups having in each case 1 to 3 carbon atoms, a cycloalkoxy group having 5 to 8 carbon atoms, in which a methylene group in the 3- or 4-position in the cycloalkyl part is replaced by an oxygen atom or by an imino group which is optionally substituted by an alkyl, phenylalkyl or phenylalkoxycarbonyl group, in which the alkyl and alkoxy part in each case can contain 1 to 3 carbon atoms, or is optionally substituted by an alkanoyl group having 2 to 6 carbon atoms, and the cycloalkyl part additionally can be substituted by one or two alkyl groups having in each case 1 to 3 carbon atoms, a cycloalkenyloxy group, in which the cycloalkenyl part can contain 4 to 7 carbon atoms, an alkenyloxy, phenylalkenyloxy, alkynyloxy or phenylalkynyloxy group, with the proviso that no bond to the oxygen atom starts from a carbon atom which carries a double or triple bond, and in which the alkenyl and alkynyl part in each case can contain 3 to 5 carbon atoms, a cycloalkylalkoxy group, in which the cycloalkyl part can contain 3 to 8 carbon atoms and the alkoxy part can contain 1 to 3 carbon atoms, a bicycloalkoxy group having a total of 8 to 10 carbon atoms, which additionally can be substituted in the bicycloalkyl part by one or two alkyl groups having in each case 1 to 3 carbon atoms, a 1,3-dihydro-3-oxo-1-isobenzofuranyloxy group or an $R_5$—CO—O—($R_3CR_4$)—O— group, in which $R_3$ is a hydrogen atom or a $C_{1-6}$-alkyl, $C_{3-7}$-cycloalkyl or phenyl group, $R_4$ is a hydrogen atom or a $C_{1-6}$-alkyl group and $R_5$ is a $C_{1-5}$-alkyl, $C_{1-5}$-alkoxy, $C_{5-7}$-cycloalkyl or $C_{5-7}$-cycloalkoxy group, or E is an α-amino group of a naturally occurring amino acid or esters thereof.

The terms "an aryl group", "a phenyl group" or "a phenylene group" mentioned in the definition of the above radicals in each case are to be understood as meaning, in particular, a phenyl or phenylene group which is optionally mono-, di- or trisubstituted by fluorine, chlorine, bromine or iodine atoms or by alkyl, trifluoromethyl, nitro, amino, alkylamino, dialkylamino, alkanoylamino, hydroxyl, alkoxy, carboxyl, alkoxycarbonyl, hydroxycarbonylalkoxy, alkoxycarbonylalkoxy, aminocarbonyl, alkylaminocarbonyl or dialkylaminocarbonyl groups, where the substituents can be identical or different and the abovementioned alkyl and alkoxy parts in each case can contain 1 to 3 carbon atoms, the esters of a naturally occurring α-amino group are to be understood as meaning the $C_{1-6}$-alkyl, $C_{2-6}$-alkenyl, $C_{5-7}$-cycloalkyl, phenyl or phenyl-$C_{1-3}$-alkyl esters thereof, such as the methyl, ethyl, n-propyl, isopropyl, tert-butyl, allyl, phenyl or benzyl ester, and a radical which can be split off in vivo is to be understood as meaning an alkanoyl group having a total of 1 to 6 carbon atoms, or a benzoyl, allyloxycarbonyl, $C_{1-5}$-alkoxycarbonyl or phenyl-$C_{1-3}$-alkoxycarbonyl group, such as the formyl, acetyl, propionyl, butanoyl, pentanoyl, hexanoyl, benzoyl, allyloxycarbonyl, methoxycarbonyl, ethoxycarbonyl, propoxycarbonyl, isopropoxycarbonyl, butoxycarbonyl, tert-butoxycarbonyl, pentoxycarbonyl, hexoxycarbonyl, benzyloxycarbonyl, phenylethoxycarbonyl or phenylpropoxycarbonyl group.

Preferred compounds of the above general formula I are those in which $R_a$ is a 3-pyrrolidinyl, 3-piperidinyl, 4-piperidinyl, 3-hexamethyleniminyl or 4-hexamethyleniminyl group, where the hydrogen atom of the abovementioned alkylenimino rings in each case can be replaced by a $C_{1-5}$-alkyl or phenyl-$C_{1-3}$-alkyl group, in which the alkyl part in each case can be substituted by a carboxyl, $C_{1-3}$-alkoxycarbonyl, aminocarbonyl, N-$C_{1-3}$-alkyl-aminocarbonyl or N,N-di-($C_{1-3}$-alkyl)-aminocarbonyl group or else, if the abovementioned substituents are not on an α-carbon atom adjacent to a nitrogen atom, can be substituted by a hydroxyl, $C_{1-3}$-alkoxy, amino, $C_{1-3}$-alkylamino or di-($C_{1-3}$-alkyl) amino group, or can be replaced by a radical which can be split off in vivo, such as a $C_{1-4}$-alkoxycarbonyl or benzyloxycarbonyl group, $R_b$ and $R_c$, which can be identical or different, are hydrogen atoms or $C_{1-3}$-alkyl or phenyl-$C_{1-3}$-alkyl groups, or $R_b$ and $R_c$, together with the ethylene bridge in between, are an o-phenylene group, where one or two methylene groups in the 1,4-piperazinylene group of the above general formula I additionally in each case can be replaced by a carbonyl group, $Y_1$ is an —$A_1$—, —CO—, —CO—CO—, —$A_1$—CO—, —CO—$A_1$—, —CO—$A_1$—CO—, —CO—$NR_1$—$A_2$—, —CO—$A_2$—O— or —CO—$A_2$—$NR_1$— group, in which $R_1$ is a hydrogen atom or a $C_{1-5}$-alkyl or phenyl-$C_{1-3}$-alkyl group, $A_1$ is an n-$C_{1-5}$-alkylene group which is optionally substituted by a $C_{1-5}$-alkyl or phenyl-$C_{1-3}$-alkyl group or else by an $R_1O$ group, if this is not in the α-position relative to a nitrogen atom, where the phenyl group can be substituted by a hydroxyl, $C_{1-3}$-alkoxy or benzyloxy group, and $A_2$ is an n-$C_{1-4}$-alkylene group which is optionally substituted by a $C_{1-5}$-alkyl or phenyl-$C_{1-3}$-alkyl group, $Y_2$ is a phenylene, cyclohexylene or pyridinylene group, a 4-piperidinylene or 1,4-piperazinylene group, in which a methylene group adjacent to a nitrogen atom in each case can be replaced by a carbonyl group, where a 4-piperidinylene group additionally can be substituted by an $R_1O$ group in the 4-position, with the proviso that no N,O— or O,O-acetal and no N,O or N,N bond is formed in the linkage with $Y_1$ or $Y_3$, or an —$NR_1$—B— group, where the linkage with the $Y_1$ group is effected via the nitrogen atom of the —$NR_1$— group, in which $R_1$ is defined as above and B is a phenylene, cyclohexylene, piperidinylene or pyridinylene group, where the linkage of the piperidinylene group with the radical —$NR_1$— in each case is effected via the 4-position and in which a methylene group adjacent to a nitrogen atom additionally can be replaced by a carbonyl group, $Y_3$ is a —CO—, —$A_2$—CO—, —$CH_2$—CH($NHR_2$)—CO—, —$NR_2$—$A_3$—CO—, —$CH_2$—$NR_2$—$A_3$—CO—, —O—$A_3$—CO—, —CO—$A_3$—CO— or —CO—$NR_1$—$A_3$—CO— group, in which $R_1$ and $A_2$ are defined as above, $A_3$ is an n-$C_{1-3}$-alkylene group which is optionally substituted by a $C_{1-5}$-alkyl, phenyl, pyridyl or phenyl-$C_{1-3}$-alkyl group and $R_2$ is a hydrogen atom, a $C_{1-5}$-alkyl, phenyl-$C_{1-3}$-alkyl, $C_{1-5}$-alkoxycarbonyl, $C_{1-5}$-alkylsulphonyl, phenyl-$C_{1-3}$-alkylsulphonyl or phenylsulphonyl group or a formyl group which is optionally substituted by a $C_{1-4}$-alkyl, phenyl or phenyl-$C_{1-3}$-alkyl group, and the linkage of the —$A_2$—CO— group with the radical $Y_2$ is effected via the radical $A_2$, that of the —$NR_2$—$A_3$—CO— group is effected via the $NR_2$ group and that of the —O—$A_3$—CO— group is effected via the oxygen atom, but where an —$NR_2$—$A_3$—CO—, —$CH_2$—$NR_2$—$A_3$—CO— or —O—$A_3$—CO— group cannot be linked with a nitrogen atom of the radical $Y_2$, and E is a hydroxyl or a $C_{1-6}$-alkoxy, phenyl-$C_{1-3}$-alkoxy or $C_{5-7}$-cycloalkoxy group or an $R_5$—CO—O—($R_3CR_4$)—O— group, in which $R_3$ is a hydrogen atom or a $C_{1-6}$-alkyl, $C_{3-7}$-cycloalkyl or phenyl group, $R_4$ is a hydrogen atom or a $C_{1-6}$-alkyl group and $R_5$ is a $C_{1-5}$-alkyl, $C_{1-5}$-alkoxy, $C_{5-7}$-cycloalkyl or $C_{5-7}$-cycloalkoxy group, or E is an α-amino group of a naturally occurring amino acid and $C_{1-6}$-alkyl and benzyl esters thereof, tautomers thereof, stereoisomers thereof, including their mixtures, and salts thereof.

Particularly preferred compounds of the above general formula I are those in which $R_a$ is a 3-pyrrolidinyl or 4-piperidinyl group, where the hydrogen atom of the abovementioned alkylenimino rings in each case can be replaced by a $C_{1-5}$-alkyl or phenyl-$C_{1-3}$-alkyl group or by a radical which can be split off in vivo, such as a $C_{1-4}$-alkoxycarbonyl or benzyloxycarbonyl group, $R_b$ and $R_c$, which can be identical or different, are hydrogen atoms or $C_{1-3}$-alkyl or phenyl-$C_{1-3}$-alkyl groups, or $R_b$ and $R_c$, together with the ethylene bridge in between, are an o-phenylene group, where one or two methylene groups in the 1,4-piperazinylene group of the above general formula I additionally in each case can be replaced by a carbonyl group, $Y_1$ is an —$A_1$—, —CO—, —CO—CO—, —$A_1$—CO—, —CO—$A_1$—, —CO—CH$_2$—CO—, —CO—NR$_1$—$A_2$—, —CO—$A_2$—O— or —CO—$A_2$—NR$_1$— group, in which $R_1$ is a hydrogen atom or a $C_{1-5}$-alkyl or phenyl-$C_{1-2}$-alkyl group, $A_1$ is an n-$C_{1-5}$-alkylene group which is optionally substituted by a $C_{1-5}$-alkyl or phenyl-$C_{1-2}$-alkyl group or else by an $R_1O$ group, if this is not in the α-position relative to a nitrogen atom, where the phenyl group can be substituted by a hydroxyl or methoxy group, and $A_2$ is an n-$C_{1-3}$-alkylene group, $Y_2$ is a 1,4-cyclohexylene or 1,4-phenylene group, a 4-piperidinylene or 1,4-piperazinylene group, in which a methylene group adjacent to a nitrogen atom in each case can be replaced by a carbonyl group, a 4-piperidinylene group which is substituted by an $R_1O$ group in the 4-position, but where no N,O— or O,O-acetal and no N,O or N,N bond may be formed in the linkage with $Y_1$ or $Y_3$, or an —NR$_1$—B— group, where the linkage with the $Y_1$ group is effected via the nitrogen atom of the —NR$_1$— group, in which $R_1$ is defined as above and B is a 1,3-phenylene, 1,4-phenylene, 1,4-cyclohexylene or 4-piperidinylene group, where the linkage of the piperidinylene group with the radical —NR$_1$— in each case is effected via the 4-position, $Y_3$ is a —CO—, —$A_2$—CO—, —NR$_2$—$A_3$—CO—, —CH$_2$—NR$_2$—$A_3$—CO—, —O—$A_3$—CO—, —CO—$A_3$—CO— or —CO—NR$_1$—$A_3$—CO— group, in which $R_1$ and $A_2$ are defined as above, $A_3$ is an n-$C_{1-3}$-alkylene group which is optionally substituted by a $C_{1-5}$-alkyl, phenyl, pyridyl or phenyl-$C_{1-2}$-alkyl group and $R_2$ is a hydrogen atom or a $C_{1-3}$-alkyl, phenyl-$C_{1-3}$-alkyl, $C_{1-5}$-alkoxycarbonyl, $C_{1-3}$-alkanoyl, $C_{1-5}$-alkylsulphonyl or phenylsulphonyl group, and the linkage of the —$A_2$—CO—group with the radical $Y_2$ is effected via the radical $A_2$, that of the —NR$_2$—$A_3$—CO— group is effected via the NR$_2$ group and that of the —O—$A_3$—CO— group is effected via the oxygen atom, but where an —NR$_2$—$A_3$—CO—, —CH$_2$—NR$_2$—$A_3$—CO— or —O—$A_3$—CO— group cannot be linked with a nitrogen atom of the radical Y2, and E is a hydroxyl, $C_{1-5}$-alkoxy, phenyl-$C_{1-3}$-alkoxy or $C_{5-7}$-cycloalkoxy group or an $R_5$—CO—O—($R_3CR_4$)—O— group, in which $R_3$ is a hydrogen atom or a $C_{1-3}$-alkyl or $C_{5-7}$-cycloalkyl group, $R_4$ is a hydrogen atom and $R_5$ is a $C_{1-5}$-alkyl or $C_{1-3}$-alkoxy group, or E is an α-amino group of a naturally occurring amino acid and $C_{1-6}$-alkyl or benzyl esters thereof, tautomers thereof, stereoisomers thereof, including their mixtures, and salts thereof.

Especially preferred compounds of the above general formula I are those in which $R_a$ is a 3-pyrrolidinyl or 4-piperidinyl group, where the hydrogen atom of the abovementioned alkylenimino rings in each case can be replaced by a $C_{1-3}$-alkyl or benzyl group or by a tert-butyloxycarbonyl group, $R_b$ and $R_c$ in each case are a hydrogen atom, $Y_1$ is an ethylene group which is optionally substituted by a hydroxyl group, or a —CO—, —CO—CO—, —$A_1$—CO—, —CO—$A_1$—, —CO—CH$_2$—CO—, —CO—NH—$A_2$—, —CO—CH$_2$—O— or —CO—CH$_2$—NH— group, in which $A_1$ is a $C_{1-2}$-alkylene group which is optionally substituted by a methyl or methoxybenzyl group and $A_2$ is a $C_{1-2}$-alkylene group, $Y_2$ is a 1,4-cyclohexylene, 1,4-phenylene, 4-piperidinylene or 1,4-piperazinylene group, a 4-hydroxy-1,4-piperidylene group, but where no N,O— or O,O-acetal and no N,O or N,N bond may be formed in the linkage with $Y_1$ or $Y_3$, or —NH—B— group, where the linkage with the $Y_1$ group is effected via the nitrogen atom of the —NH— group, and B is a 1,3-phenylene, 1,4-phenylene, 1,4-cyclohexylene or 4-piperidinylene group, where the linkage of the piperidinylene group with the radical —NH— in each case is effected via the 4-position, $Y_3$ is a —CO—, —$A_2$—CO—, —NR$_2$—$A_3$—CO—, —CH$_2$—NR$_2$—$A_3$—CO—, —O—$A_3$—CO—, —CO—$A_3$—CO— or —CO—NH—$A_3$—CO— group, in which $A_2$ is defined as above, $A_3$ is a $C_{1-2}$-alkylene group which is optionally substituted by a methyl or phenyl group and $R_2$ is a hydrogen atom or a methyl, benzyl, acetyl or phenylsulphonyl group, and the linkage of the —$A_2$—CO— group with the radical $Y_2$ is effected via the radical $A_2$, that of the —NR$_2$—$A_3$—CO— group is effected via the NR$_2$ group and that of the —O—$A_3$—CO— group is effected via the oxygen atom, but where an —NR$_2$—$A_3$—CO—, —CH$_2$—NR$_2$—$A_3$—CO— or —O—$A_3$—CO—group cannot be linked with a nitrogen atom of the radical $Y_2$, and E is a hydroxyl, $C_{1-5}$-alkoxy, benzyloxy or $C_{5-7}$-cycloalkoxy group or E is an α-amino group of a naturally occurring amino acid and $C_{1-6}$-alkyl or benzyl esters thereof, in particular those compounds of the above general formula I in which $R_a$ is a 4-piperidinyl group, $R_b$ and $R_c$ in each case are a hydrogen atom, $Y_1$ is a —CO—, —COCH$_2$—, —COCH$_2$CH$_2$— or —CO—CH$_2$—O— group, $Y_2$ is a 1,4-phenylene, 4-piperidinylene, 1,4-piperazinylene or —NH—B— group, where the linkage with the $Y_1$ group is effected via the nitrogen atom of the —NH— group, and B is a 1,4-phenylene or 1,4-cyclohexylene group, $Y_3$ is a —CO—, —CH$_2$CO—, —CH$_2$CH$_2$CO—, —CH$_2$CH$_2$CH$_2$CO—, —O—CH$_2$—CO—, or —CO—NH—CH$_2$CH$_2$—CO— group, and E is a hydroxyl, $C_{1-5}$-alkoxy or $C_{5-7}$-cycloalkoxy group, tautomers thereof, stereoisomers thereof, including their mixtures, and salts thereof.

Particularly valuable compounds which may be mentioned are, for example, the following:

(a) [4-trans-[3-[4-(4-piperidinyl)-piperazin-1-yl]propionyl]-amino]cyclohexanecarboxylic acid, (b) [3-[4-trans-[4-(4-piperidinyl)-piperazin-1-yl]carbonylamino]cyclohexyl]propionic acid, (c) N-[[4-(4-piperidinyl)-piperazin-1-yl]carbonyl]-4-(4-piperidinyl)-butyric acid, (d) N-[[4-(4-piperidinyl)-piperazin-1-yl]carbonyl]-3-(piperidin-4-yloxy)-propionic acid, (e) N-[4-[[4-(4-piperidinyl)-piperazin-1-yl]carbonyl] piperidinyl]-β-alanine, (f) [4-[[4-(4-piperidinyl)-piperazin-1-yl]carbonylamino] phenoxy]acetic acid, (g) [4-[[4-(4-piperidinyl)-piperazin-1-yl]acetyl]phenoxy] acetic acid, (h) [4-[2-[[4-(piperidin-4-yl)-piperazin-1-yl]-carbonyl]-ethyl]-piperidin-1-yl]-acetic acid, and $C_{1-5}$-alkyl and $C_{5-6}$-cycloalkyl esters thereof, but in particular the compound (f) [4-[[4-(4-piperidinyl)-piperazin-1-yl]carbonylamino] phenoxy]acetic acid and the butyl, isobutyl, cyclopentyl or cyclohexyl ester thereof, tautomers thereof, stereoisomers thereof and salts thereof.

According to the invention, the new compounds are obtained, for example, by the following processes:

a. To prepare a compound of the general formula I in which $Y_1$ is a —CO—CO—, —$A_1$—CO—, —$A_2$—SO$_2$—, —CO—$A_1$—CO—, —CO—NR$_1$—$A_2$—CO— or —CO—$A_2$—NR$_1$—CO— group and the carbonyl group of the radical $Y_1$ is bonded with an oxygen or nitrogen atom of the radical $Y_2$:

Reaction of a compound of the general formula

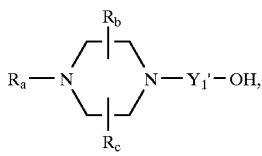

(II)

in which $R_a$ to $R_c$ are defined as above and $Y_1'$ is a —CO—CO—, —$A_1$—CO—, —$A_2$—SO$_2$—, —CO—$A_1$—CO—, —CO—NR$_1$—$A_2$—CO— or —CO—$A_2$—NR$_1$—CO— group, or reactive derivatives thereof, with a compound of the general formula

H—$Y_2'$—$Y_3$—E', (III)

in which $Y_3$ is defined as above, $Y_2'$ has the meanings mentioned above for $Y_2$, with the proviso that the hydrogen atom is bonded to a basic nitrogen atom or to an oxygen atom of the radical $Y_2$, and E' has the meanings mentioned above for E, with the exception of the $R_5$—CO—O—($R_3CR_4$)—O— group.

The reaction of a carboxylic acid of the general formula II is carried out, if appropriate, in a solvent or solvent mixture, such as methylene chloride, dimethylformamide, benzene, toluene, chlorobenzene, tetrahydrofuran, benzene/tetrahydrofuran or dioxane, or in a corresponding amine of the general formula III, if appropriate in the presence of a dehydrating agent, for example in the presence of isobutyl chloroformate, tetraethyl orthocarbonate, trimethyl orthoacetate, 2,2-dimethoxypropane, tetramethoxysilane, thionyl chloride, trimethylchlorosilane, phosphorus trichloride, phosphorus pentoxide, N,N'-dicyclohexylcarbodiimide, N,N'-dicyclohexylcarbodiimide/ N-hydroxysuccinimide, N,N'-dicyclohexylcarbodiimide/1-hydroxy-benzotriazole, 2-(1H-benzotriazol-1-yl)-1,1,3,3-tetramethyluronium tetrafluoroborate, 2-(1H-benzotriazol-1-yl)-1,1,3,3-tetramethyluronium tetrafluoroborate/1-hydroxy-benzotriazole, N,N'-carbonyldiimidazole or triphenylphosphine/carbon tetrachloride, and if appropriate with the addition of a base, such as pyridine, 4-dimethylaminopyridine, N-methylmorpholine or triethylamine, expediently at temperatures between 0 and 150° C., preferably at temperatures between 0 and 100° C.

The reaction of a corresponding reactive compound of the general formula II, such as esters, imidazolides or halides thereof, with an amine of the general formula III is preferably carried out in a corresponding amine as the solvent, if appropriate in the presence of a further solvent, such as methylene chloride or ether, and preferably in the presence of a tertiary organic base, such as triethylamine, N-ethyl-diisopropylamine or N-methyl-morpholine, at temperatures between 0 and 150° C., preferably at temperatures between 50 and 100° C.

b. To prepare a compound of the general formula I in which at least one of the radicals $R_a$, $R_2$ and E must contain a reactive hydrogen atom, with the proviso that E has the meanings mentioned above for E, with the exception of the $R_5$—CO—O—($R_3CR_4$)—O— group:

Conversion of a compound of the general formula

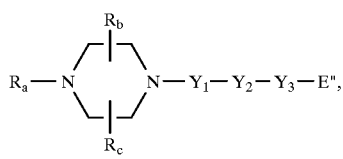

(IV)

in which $R_a$ to $R_c$ and $Y_1$ to $Y_3$ are defined as above and

E" is a hydroxyl group or, together with the adjacent carbonyl group of the radical $Y_3$, is a group which can be converted into a carboxyl group by elimination of a protective radical which can be split off by means of hydrolysis, treatment with an acid or base, thermolysis or hydrogenolysis, but where at least one of the radicals $R_a$, $R_2$ or E" must contain a radical which can be split off, into a compound of the general formula I in which at least one of the radicals $R_a$, $R_2$ and E must contain a reactive hydrogen atom, with the proviso that E has the meanings mentioned above for E, with the exception of the $R_5$—CO—O—($R_3CR_4$)—O— group.

As protective groups for a hydroxyl group of a carboxyl group, for example, the functional derivatives of a carboxyl group, such as unsubstituted or substituted amides, esters, thioesters, trimethylsilyl esters, ortho esters or imino esters thereof, can be converted into a carboxyl group by means of hydrolysis, esters with tertiary alcohols, for example the tert-butyl ester, can be converted into a carboxyl group by means of treatment with an acid or thermolysis and esters with aralkanols, for example the benzyl ester, can be converted into a carboxyl group by means of hydrogenolysis.

The hydrolysis is expediently carried out either in the presence of an acid, such as hydrochloric acid, sulphuric acid, phosphoric acid, acetic acid, trichloroacetic acid, trifluoroacetic acid or mixtures thereof, or in the presence of a base, such as lithium hydroxide, sodium hydroxide or potassium hydroxide, in a suitable solvent, such as water, water/methanol, water/ethanol, water/isopropanol, methanol, ethanol, water/tetrahydrofuran or water/dioxane, at temperatures between −10 and 120° C., for example at temperatures between room temperature and the boiling point of the reaction mixture.

Under the abovementioned reaction conditions, any N-acylamino or $C_{1-5}$-alkoxycarbonyl groups present, such as an N-trifluoroacetylamino or tert-butyloxycarbonyl group, can be converted into the corresponding amino groups.

If E" in a compound of the formula IV is, for example, the tert-butyloxy group, the tert-butyl group can also be split off by treatment with an acid, such as trifluoroacetic acid, formic acid, p-toluenesulphonic acid, sulphuric acid, hydrochloric acid, phosphoric acid or polyphosphoric acid, if appropriate in an inert solvent, such as methylene chloride, chloroform, benzene, toluene, diethyl ether, tetrahydrofuran or dioxane, preferably at temperatures between −10 and 120° C., for example at temperatures between 0 and 60° C., or else thermally, if appropriate in an inert solvent, such as methylene chloride, chloroform, benzene, toluene, tetrahydrofuran or dioxane, and preferably in the presence of a catalytic amount of an acid, such as p-toluenesulphonic acid, sulphuric acid, phosphoric acid or polyphosphoric acid, preferably at the boiling point of the solvent used, for example at temperatures between 40 and 120° C. Under the abovementioned reaction conditions, any N-tert-butyloxycarbonylamino groups present can be converted into the corresponding amino groups.

If E" in a compound of the formula IV is, for example, the benzyloxy group, the benzyl group can also be split off hydrogenolytically in the presence of a hydrogenation catalyst, such as palladium/charcoal, in a suitable solvent, such as methanol, ethanol, ethanol/water, glacial acetic acid, ethyl acetate, dioxane or dimethylformamide, preferably at temperatures between 0 and 50° C., for example at room temperature, under a hydrogen pressure of 1 to 5 bar. During the hydrogenolysis, other radicals can be converted simultaneously, for example a nitro group into an amino group, a benzyloxy group into a hydroxyl group and an N-benzylamino, N-benzylimino, N-benzyloxycarbonylamino or N-benzyloxycarbonylimino group into a corresponding amino or imino group.

c. To prepare a compound of the general formula I in which E is defined as above, with the exception of the hydroxyl group, and $Y_2$ is a phenylene, cyclohexylene, 3-piperidinylene or 4-piperidinylene group which is bonded to $Y_3$ via an oxygen atom or the $NR_2$ group of the radical $Y_3$ and $A_3$ is an ethylene group which is optionally substituted by a $C_{1-5}$-alkyl, aryl, pyridyl or aryl-$C_{1-3}$-alkyl group:

Reaction of a compound of the general formula

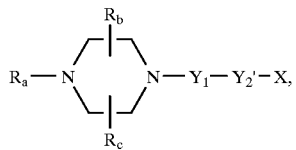

(V)

in which $R_a$ to $R_c$ and $Y_1$ are defined as above, $Y_2'$ is a phenylene, cyclohexylene, 3-piperidinylene or 4-piperidinylene group and X is a hydroxyl or $HNR_2$ group, in which
$R_2$ is a hydrogen atom or a $C_{1-5}$-alkyl, aryl-$C_{1-3}$-alkyl or aryl group, with a compound of the general formula

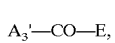

(VI)

in which
E is defined as above, with the exception of the hydroxyl group, and
$A_3'$ is a vinyl group which is optionally substituted by a $C_{1-5}$-alkyl, phenyl, pyridyl or phenyl-$C_{1-3}$-alkyl group.

The reaction is preferably carried out in a solvent, such as methanol, ethanol, methylene chloride, tetrahydrofuran, toluene, dioxane, dimethyl sulphoxide or dimethylformamide, if appropriate in the presence of a tertiary organic base, such as N-ethyl-diisopropylamine or N-methyl-morpholine, at temperatures between −30 and 150° C., but preferably at temperatures between 0 and 100° C.

d. Reaction of a compound of the general formula

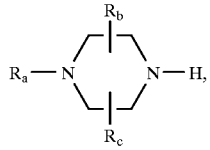

(VII)

in which $R_a$ to $R_c$ are defined as above, with a compound of the general formula

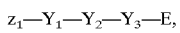

(VIII)

in which
$Y_1$, $Y_2$, $Y_3$ and E are defined as above and
$Z_1$ is a nucleofugic leaving group, such as a halogen atom, for example a chlorine, bromine or iodine atom, a sulphonic acid ester group, for example a methanesulphonyloxy or p-toluenesulphonyloxy group, an imidazolyl, triazolyl or 4-nitrophenyloxy group or else, if $Y_1$ is a carbonyl group,
$Z_1$ together with $R_1$ of an —$NR_1$—B— group is a further carbon-nitrogen bond.

The reaction is preferably carried out in a solvent, such as methanol, ethanol, methylene chloride, tetrahydrofuran, toluene, dioxane, dimethyl sulphoxide or dimethylformamide, if appropriate in the presence of an inorganic or a tertiary organic base or if appropriate in the presence of a dehydrating agent at temperatures between −30 and 200° C.

The reaction of a compound of the general formula VIII in which $Z_1$ is a nucleofugic leaving group or with an isocyanate of the general formula VIII is preferably carried out in a solvent, such as methylene chloride, acetonitrile, tetrahydrofuran, dioxane, toluene, dimethylformamide or dimethyl sulphoxide, if appropriate in the presence of a base, such as sodium hydride, potassium carbonate, potassium tert-butylate or N-ethyl-diisopropylamine, at temperatures between −20 and 100° C., preferably at temperatures between 0 and 60° C.

e. To prepare a compound of the general formula I in which E is defined as above, with the exception of the hydroxyl group:

Reaction of a compound of the general formula

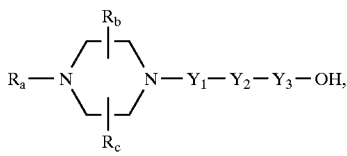

(IX)

in which
$R_a$ to $R_c$ and $Y_1$ to $Y_3$ are defined as above, with an alcohol of the general formula

     (X)

or with the formamide acetal thereof,
or with a compound of the general formula

     (XI)

in which
$R_d$ is an alkyl group having 1 to 6 carbon atoms, a phenylalkyl group in which the alkyl part can contain 1 to 3 carbon atoms, a cycloalkyl group having 3 to 9 carbon atoms, in which the cycloalkyl part having 5 to 8 carbon atoms additionally can be substituted by one or two alkyl groups having in each case 1 to 3 carbon atoms, a cycloalkyl group having 5 to 8 carbon atoms, in which a methylene group in the 3- or 4-position in the cycloalkyl part is replaced by an oxygen atom or by an imino group which is optionally substituted by an alkyl, phenylalkyl or phenylalkoxycarbonyl group in which the alkyl and alkoxy part in each case can contain 1 to 3 carbon atoms, or is optionally substituted by an alkanoyl group having 2 to 6 carbon atoms, and the cycloalkyl part additionally can be substituted by one or two alkyl groups having in each case 1 to 3 carbon atoms, a cycloalkenyl group in which the cycloalkenyl part can contain 4 to 7 carbon atoms, an alkenyl, phenylalkenyl, alkynyl or phenylalkynyl group, with the proviso that no bond to the oxygen atom starts from a carbon atom which carries a double or triple bond, and in which the alkenyl and alkynyl part in each case can contain 3 to 5 carbon atoms, a cycloalkylalkyl group in which the cycloalkyl part can contain 3 to 8 carbon atoms and the alkyl part can contain 1 to 3 carbon atoms, a bicycloalkyl group having a total of 8 to 10 carbon atoms, which additionally can be substituted in the bicycloalkyl part by one or two alkyl groups having in each case 1 to 3 carbon atoms, or a 1,3-dihydro-3-oxo-1-isobenzofuranyloxy group,
$R_e$ has the meanings mentioned above for $R_d$ and additionally is an $R_5$—CO—O—$(R_3CR_4)$—O— group, in which
$R_3$ to $R_5$ are defined as above, and
$Z_2$ is a leaving group, such as a halogen atom, for example a chlorine or bromine atom.

The reaction with an alcohol of the general formula X is expediently carried out in a solvent or solvent mixture, such as methylene chloride, benzene, toluene, chlorobenzene, tetrahydrofuran, benzene/tetrahydrofuran or dioxane, but preferably in an alcohol of the general formula X, if appropriate in the presence of an acid, such as hydrochloric acid, or in the presence of a dehydrating agent, for example in the presence of isobutyl chloroformate, thionyl chloride, trimethylchlorosilane, hydrochloric acid, sulphuric acid, methanesulphonic acid, p-toluenesulphonic acid, phosphorus trichloride, phosphorus pentoxide, N,N'-dicyclohexylcarbodiimide, N,N'-dicyclohexylcarbodiimide/N-hydroxysuccinimide, N,N'-carbonyldiimidazole or N,N'-thionyldiimidazole, triphenylphosphine/carbon tetrachloride or triphenylphosphine/diethyl azodicarboxylate, if appropriate in the presence of a base, such as potassium carbonate, N-ethyl-diisopropylamine or N,N-dimethylamino-pyridine, expediently at temperatures between 0 and 150° C., preferably at temperatures between 0 and 80° C.

The reaction with a compound of the general formula XI is expediently carried out in a solvent, such as methylene chloride, tetrahydrofuran, dioxane, dimethyl sulphoxide, dimethylformamide or acetone, if appropriate in the presence of a reaction accelerator such as sodium iodide or potassium iodide, and preferably in the presence of a base, such as sodium carbonate or potassium carbonate, or in the presence of a tertiary organic base, such as N-ethyldiisopropylamine or N-methyl-morpholine, which can also simultaneously serve as the solvent, or if appropriate in the presence of silver carbonate or silver oxide, at temperatures between −30 and 100° C., but preferably at temperatures between −10 and 80° C.

f. To prepare a compound of the general formula I in which $A_1$ is an n-$C_{1-5}$-alkyl group which is substituted by a hydroxyl group:

Reduction of a compound of the general formula

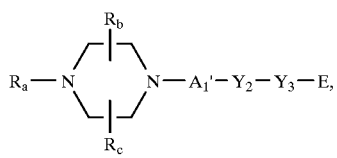

(X)

in which
$R_a$ to $R_c$, E, $Y_2$ and $Y_3$ are defined as above and $A_1'$ is an n-$C_{1-5}$-alkyl group in which a methylene group is replaced by a carbonyl group.

The reduction is preferably carried out in a solvent, such as water or methanol, ethanol, tetrahydrofuran, dioxane or mixtures thereof with water, at temperatures between 0 and 100° C., preferably at temperatures between 20° C. and the boiling point of the solvent used.

However, the reduction is preferably carried out with a complex metal hydride, such as sodium borohydride or lithium borohydride, expediently at a pH of 6–7 and at room temperature, or with hydrogen in the presence of a hydrogenation catalyst, for example in the presence of palladium/charcoal, under a hydrogen pressure of 1 to 5 bar and preferably at temperatures between 20° C. and the boiling point of the solvent used.

g. Reductive alkylation of a ketone of the general formula $$R_a'—H, \quad (XI)$$

in which $R_a'$ has the meanings mentioned above for $R_a$, with the proviso that a ring methylene group is replaced by a carbonyl group, with an amine of the general formula

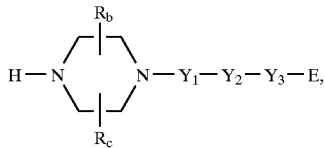
(XII)

in which $R_b$, $R_c$, E and $Y_1$ to $Y_3$ are defined as above.

The reductive alkylation is preferably carried out in a solvent, such as water or methanol, ethanol, tetrahydrofuran, dioxane, formic acid, acetic acid, trifluoroacetic acid, sulphuric acid or mixtures thereof with water, at temperatures between 0 and 100° C., preferably at temperatures between 20° C. and the boiling point of the solvent used.

However, the reductive alkylation is preferably carried out with a complex metal hydride, such as sodium borohydride, lithium borohydride, sodium cyanoborohydride, zinc borohydride, sodium triacetoxyborohydride or borane/pyridine, expediently at a pH of 1–7, if appropriate in the presence of a dehydrating agent, such as a molecular sieve or titanium(IV) isopropylate, and at room temperature, or with hydrogen in the presence of a hydrogenation catalyst, for example in the presence of palladium/charcoal, under a hydrogen pressure of 1 to 5 bar, preferably at temperatures between 20° C. and the boiling point of the solvent used.

h. To prepare a compound of the general formula I in which $R_2$ is an n-$C_{1-5}$-alkyl or aryl-$C_{1-3}$-alkyl group:

Alkylation of a compound of the general formula (XIII)

in which $R_a$ to $R_c$, E, $Y_1$ and $Y_2$ are defined as above and
$Y_3'$ is a —$CH_2CH(NH_2)$—CO— or —NH—$A_3$—CO— group, in which $A_3$ is defined as above, with a compound of the general formula $$Z_3—R_f, \quad (XIV)$$

in which $R_f$ is an n-$C_{1-5}$-alkyl or aryl-$C_{1-3}$-alkyl group and
$Z_3$ is a nucleofugic leaving group, such as a halogen atom, for example a chlorine, bromine or iodine atom, a hydroxyl or sulphonic acid ester group, for example a methanesulphonyloxy or p-toluenesulphonyloxy group, or else $Z_3$, together with a hydrogen atom of the adjacent carbon atom, is an oxygen atom of a carbonyl group.

The reaction is preferably carried out in a solvent, such as methanol, ethanol, methylene chloride, tetrahydrofuran, toluene, dioxane, dimethyl sulphoxide or dimethylformamide, if appropriate in the presence of an inorganic or a tertiary organic base and, if $Z_3$, together with a hydrogen atom of the adjacent carbon atom, is an oxygen atom, in the presence of a reducing agent at temperatures between 0 and 100° C., preferably at temperatures between 20° C. and the boiling point of the solvent used.

The reaction with a compound of the general formula XIV in which $Z_3$ is a nucleofugic leaving group is preferably carried out in a solvent, such as methylene chloride, acetonitrile, tetrahydrofuran, toluene, dimethylformamide or dimethyl sulphoxide, if appropriate in the presence of a base, such as sodium hydride, potassium carbonate, potassium tert-butylate or N-ethyl-diisopropylamine, at temperatures between 0 and 60° C.

The reductive aminoalkylation with a compound of the general formula XIV in which $Z_3$, together with a hydrogen atom of the adjacent carbon atom, is an oxygen atom is preferably carried out in the presence of a complex metal hydride, such as sodium borohydride, lithium borohydride, sodium cyanoborohydride, zinc borohydride, sodium triacetoxyborohydride or borane/pyridine, expediently at a pH of 1–7, if appropriate in the presence of a dehydrating agent, such as a molecular sieve or titanium(IV) isopropylate, and at room temperature, or with hydrogen in the presence of a hydrogenation catalyst, for example in the presence of palladium/charcoal, under a hydrogen pressure of 1 to 5 bar, preferably at temperatures between 20° C. and the boiling point of the solvent used. The methylation can also be carried out with formaldehyde in the presence of formic acid as the reducing agent at elevated temperatures, for example at temperatures between 60 and 120° C.

i. To prepare a compound of the general formula I in which the hydrogen atom of the imino group of the radical $R_a$ is replaced by an n-$C_{1-5}$-alkyl or aryl-$C_{1-3}$-alkyl group or by a radical which can be split off in vivo, such as a $C_{1-6}$-alkanoyl, benzoyl, allyloxycarbonyl, $C_{1-5}$-alkoxycarbonyl or phenyl-$C_{1-3}$-alkoxycarbonyl group:

Reaction of a compound of the general formula (XV)

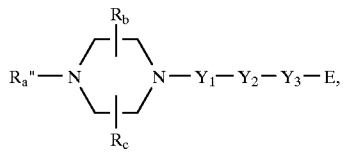

in which $R_b$, $R_c$, E and $Y_1$ to $Y_3$ are defined as above and
$R_a''$ has the meanings mentioned above for $R_a$, with the proviso that the imino group is unsubstituted, with a compound of the general formula $$R_g—Z_4, \quad (XVI)$$

in which $R_g$ is an n-$C_{1-5}$-alkyl or aryl-$C_{1-3}$-alkyl group or a radical which can be split off in vivo, such as a $C_{1-6}$-alkanoyl, benzoyl, allyloxycarbonyl, $C_{1-5}$-alkoxycarbonyl or phenyl-$C_{1-3}$-alkoxycarbonyl group and $Z_4$ is a nucleofugic leaving group, such as a halogen atom, for example a chlorine, bromine or iodine atom, a sulphonic acid ester group, for example a methanesulphonyloxy or p-toluenesulphonyloxy group, or else, if $R_g$ is an n-$C_{1-5}$-alkyl or aryl-$C_{1-3}$-alkyl group, $Z_4$, together with a hydrogen atom of the adjacent carbon atom, is an oxygen atom.

The reaction is preferably carried out in a solvent, such as methanol, ethanol, methylene chloride, tetrahydrofuran, toluene, dioxane, dimethyl sulphoxide or dimethylformamide, if appropriate in the presence of an inorganic or a tertiary organic base and, if $Z_3$, together with a hydrogen atom of the adjacent carbon atom, is an oxygen atom, in the presence of a reducing agent at temperatures between 0 and 100° C., preferably at temperatures between 20° C. and the boiling point of the solvent used.

The reaction with a compound of the general formula XVI in which $Z_4$ is a nucleofugic leaving group is preferably carried out in a solvent, such as methylene chloride, acetonitrile, tetrahydrofuran, toluene, dimethylformamide or dimethyl sulphoxide, if appropriate in the presence of a base, such as sodium hydride, potassium carbonate, potassium tert-butylate or N-ethyl-diisopropylamine, at temperatures between 0 and 60° C.

The reaction with a compound of the general formula XVI in which $Z_4$, together with a hydrogen atom of the adjacent carbon atom, is an oxygen atom is preferably carried out in the presence of a complex metal hydride, such as sodium borohydride, lithium borohydride, sodium cyanoborohydride, zinc borohydride, sodium triacetoxyborohydride or borane/pyridine, expediently at a pH of 1–7, if appropriate in the presence of a dehydrating agent, such as a molecular sieve or titanium(IV) isopropylate, and at room temperature, or with hydrogen in the presence of a hydrogenation catalyst, for example in the presence of palladium/charcoal, under a hydrogen pressure of 1 to 5 bar, preferably at temperatures between 20° C. and the boiling point of the solvent used. The methylation can also be carried out with formaldehyde in the presence of formic acid as the reducing agent at elevated temperatures, for example at temperatures between 60 and 120° C.

k. To prepare a compound of the general formula I in which $R_a$ is a 4-piperidinyl group:

Reduction of a compound of the general formula

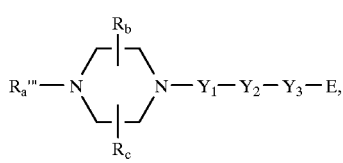

(XVII)

in which

E, $R_b$, $R_c$ and $Y_1$ to $Y_3$ are defined as above and $R_a'''$ is an N-benzyl-pyridinium group.

The reduction is preferably carried out in a solvent, such as water or methanol, ethanol, tetrahydrofuran, dioxane or mixtures thereof with water, in the presence of a reducing agent, such as sodium borohydride, at temperatures between 0 and 100° C., preferably at temperatures between 20° C. and the boiling point of the solvent used. However, the reaction is particularly advantageously carried out without prior isolation of a compound of the general formula XVII.

l. To prepare a compound of the general formula I in which $Y_3$ is an —$NR_2$—$CH_2$—CO— group in which $R_2$ is a hydrogen atom or a $C_{1-5}$-alkyl, aryl or aryl-$C_{1-3}$-alkyl group:

Reductive alkylation of a compound of the general formula

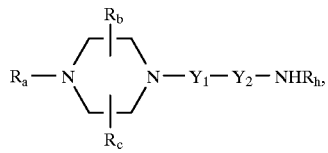

(XVIII)

in which $R_{a\ to\ Rc}$, $Y_1$ and $Y_2$ are defined as above and $R_h$ is a hydrogen atom or a $C_{1-5}$-alkyl, aryl or aryl-$C_{1-3}$-alkyl group, with glyoxalic acid or the hydrate thereof.

The reductive alkylation is preferably carried out in a solvent, such as water or methanol, ethanol, tetrahydrofuran, dioxane or mixtures thereof with water, in the presence of a reducing agent, such as sodium borohydride, at temperatures between 0 and 100° C., preferably at temperatures between 20° C. and the boiling point of the solvent used.

In the reactions described above, any reactive groups present, such as carboxyl, amino or imino groups, can be protected during the reaction by customary protective groups which are split off again after the reaction.

For example, a possible protective radical for a carboxyl group is the trimethylsilyl, methyl, ethyl, tert-butyl, benzyl or tetrahydropyranyl group and a possible protective radical for an amino or imino group is the formyl, acetyl, trifluoroacetyl, allyloxycarbonyl, ethoxycarbonyl, tert-butoxycarbonyl, benzyloxycarbonyl, benzyl, methoxybenzyl or 2,4-dimethoxybenzyl group, and for the amino group additionally the phthalyl group.

The subsequent splitting off, where appropriate, of a protective radical used is preferably carried out hydrolytically in an aqueous solvent, for example in water, isopropanol/water, acetic acid/water, tetrahydrofuran/water or dioxane/water, in the presence of an acid, such as trifluoroacetic acid, hydrochloric acid or sulphuric acid, or in the presence of an alkali metal base, such as sodium hydroxide or potassium hydroxide, or by means of ether cleavage, for example in the presence of iodotrimethylsilane, at temperatures between 0 and 120° C., preferably at temperatures between 10 and 100° C.

However, a benzyl, methoxybenzyl or benzyloxycarbonyl radical is split off, for example, hydrogenolytically, for example with hydrogen in the presence of a catalyst, such as palladium/charcoal, in a solvent, such as methanol, ethanol, ethyl acetate or glacial acetic acid, if appropriate with the addition of an acid, such as hydrochloric acid, at temperatures between 0 and 100° C., but preferably at temperatures between 20 and 60° C., and under a hydrogen pressure of 1 to 7 bar, but preferably 3 to 5 bar. However, a 2,4-dimethoxybenzyl radical is preferably split off in trifluoroacetic acid in the presence of anisole.

A tert-butyl or tert-butyloxycarbonyl radical is preferably split off by treatment with an acid, such as trifluoroacetic acid or hydrochloric acid, or by treatment with iodotrimethylsilane, if appropriate using a solvent, such as methylene chloride, dioxane, methanol or ether.

A trifluoroacetyl radical is preferably split off by treatment with an acid, such as hydrochloric acid, if appropriate in the presence of a solvent, such as acetic acid, at temperatures between 50 and 120° C., or by treatment with sodium hydroxide solution or aqueous lithium hydroxide solution, if appropriate in the presence of a solvent, such as tetrahydrofuran or methanol, at temperatures between 0 and 50° C.

An allyloxycarbonyl radical is split off by treatment with a catalytic amount of tetrakis-(triphenylphosphine)-palladium(0), preferably in a solvent, such as tetrahydrofuran, and preferably in the presence of an allyl group acceptor, such as morpholine or 1,3-dimedone, at temperatures between 0 and 100° C., preferably at room temperature, and under an inert gas, or by treatment with a catalytic amount of tris-(triphenylphosphine)-rhodium(I) chloride in a solvent, such as aqueous ethanol, and if appropriate in the presence of a base, such as 1,4-diazabicyclo[2.2.2]octane at temperatures between 20 and 70° C.

A phthalyl radical is preferably split off in the presence of hydrazine or a primary amine, such as methylamine, ethylamine or n-butylamine, in a solvent, such as methanol, ethanol, isopropanol, toluene/water or dioxane, at temperatures between 20 and 50° C.

The resulting compounds of the general formula I, as has already been mentioned above, can furthermore be separated into their enantiomers and/or diastereomers. Thus, for example, cis/trans mixtures can be separated into their cis and trans isomers, and compounds having at least one optically active carbon atom can be separated into their enantiomers.

Thus, for example, the resulting cis/trans mixtures can be separated into their cis and trans isomers by chromatography, the resulting compounds of the general formula I which occur in racemates can be separated into their optical antipodes by methods known per se (see Allinger N. L. and Eliel E. L. in "Topics in Stereochemistry", Volume 6, Wiley Interscience, 1971) and compounds of the general formula I having at least 2 stereogenic centres can be separated into their diastereomers on the basis of their physico-chemical differences by methods known per se, for example by chromatography and/or fractional crystallization, and, if these diastereomers are obtained in racemic form, they can then be separated into the enantiomers as mentioned above.

The separation into enantiomers is preferably carried out by column separation over chiral phases or by recrystallization from an optically active solvent or by reaction with an optically active substance which forms salts or derivatives, such as, for example, esters or amides, with the racemic compound, in particular acids and their activated derivatives or alcohols, and separation of the diastereomeric salt mixture or derivative obtained in this manner, for example on the basis of different solubilities, it being possible for the free antipodes to be liberated from the pure diastereomeric salts or derivatives by the action of suitable agents. Particularly customary optically active acids are, for example, the D and L forms of tartaric acid or dibenzoyltartaric acid, di-o-tolyl-tartaric acid, maleic acid, mandelic acid, camphorsulphonic acid, glutamic acid, aspartic acid or quinic acid. A possible optically active alcohol is, for example, (+)- or (−)-menthol, and a possible optically active acyl radical in amides is, for example, (+)- or (−)-menthyloxycarbonyl.

The resulting compounds of the formula I furthermore can be converted into their salts, in particular, for pharmaceutical use, into their physiologically tolerated salts with inorganic or organic acids. Possible acids for this are, for example, hydrochloric acid, hydrobromic acid, sulphuric acid, phosphoric acid, fumaric acid, succinic acid, lactic acid, citric acid, tartaric acid or maleic acid.

If desired, the new compounds of the formula I thus obtained, if these contain a carboxyl group, furthermore can then be converted into their salts with inorganic or organic acids, in particular for pharmaceutical use, into their physiologically tolerated salts. Possible bases for this are, for example, sodium hydroxide, potassium hydroxide, arginine, cyclohexylamine, ethanolamine, diethanolamine and triethanolamine.

The compounds used as starting substances are known from the literature in some cases or they are obtained by processes known from the literature (see Examples I to XLVI).

As already mentioned above, the new piperazine derivatives of the general formula I and salts thereof, in particular physiologically tolerated salts thereof with inorganic or organic acids or bases, have valuable pharmacological properties, and, in addition to an antiinflammatory action and an action which inhibits bone destruction, in particular antithrombotic, antiaggregatory and tumour- or metastasis-inhibiting actions.

The compounds of the general formula I have been investigated for their bilogical actions, for example, as follows:

1. Inhibition of the Binding of $^3$H-BIBU 52 to Human Platelets:

A suspension of human platelets in plasma is incubated with $^3$H-BIBU 52 [=(3S,5S)-5-[(4'-amidino-4-biphenylyl)-oxymethyl]-3-[(carboxyl)methyl]-2-pyrrolidinone[3-$^3$H-4-biphenylyl]], which replaces the ligand $^{125}$I-fibrinogen known from the literature, (see DE-A-4,214-245) and varius concentrations of the substance to be tested. The free and bound ligand are separated by centrigation and determined quantitatively by scintillation counting. The inhibition of $^3$H-BIBU 52 binding by the test substance is determined from the measurement values.

For this, donor blood is withdrawn form an anticubital vein and anticoagulated with trisodium citrate (final concentration 13 mM). The blood is centriged at 170×g for 10 minutes and the supernatant platelet-rich plasma (PRP) is removed. The residual blood is centriged off under severe conditions once more to isolate the plasma. The PRP is diluted 1:10 with autologous plasma. 750 $\mu$l are incubated with 50 $\mu$l of physiological saline solution, 100 $\mu$l of test substance solution, 50 $\mu$l of 14C-sucrose (3,700 Bq) and 50 $\mu$l of $^3$H-BIBU 52 (final centration: 5 nM) at room temperature for 20 minutes. To measure the non-specific binding, 100 $\mu$l of BIBU 52 (final concentration: 30 $\mu$l) are employed instead of the test substance. The samples are centrifuged at 10,000×g for 20 seconds and the supernatant is removed. 100 $\mu$l of this are measured for determination of the free ligand. The pellet is dissolved in 500 $\mu$l of 0.2N NaOH, 2 $\mu$l of scintillator and 25 $\mu$l of 5N HCl are added to 450 $\mu$l and the sample is measured. The residual plasma which still remains in the pellet is determined from the $^{14}$C content and the bound ligand is determined from the $^3$H measurement. After subtraction of the non-specific binding, the pellet activity is plotted against the concentration f the test substance and the concentration for 50% inhibition of binding is determined.

2. Antithrombotic Action:

Method

Platelet aggregation is measured in platelet-rich plasma of healthy test persons by the method of Born and Cross (J. Physiol. 170, 397 (1964)). To inhibit coagulation, 3.14% sodium citrate is added to the blood in a volume ratio of 1:10.

Collagen-induced aggregation

The course of the decrease in the optical density of the platelet suspension after addition of the substance which induces aggregation is measured and recorded photometrically. The rate of aggregation is concluded from the angle of inclination of the density curve. The point on the curve at which the highest light transmission exists is used to calculate the "optical density".

The amount of collagen is as low as possible, but is enough to result in a reaction curve which proceeds irreversibly. Commercially available collagen from Hormonchemie, Munich is used.

Before addition of the collagen, the plasma is incubated with the substance for in each case 10 minutes at 37° C.

An $EC_{50}$ which is based on a 50% change in "optical density" in the sense of inhibition of aggregation is determined graphically from the measurement figures obtained.

The following table contains the results found:

| Substance (Example No.) | Fibrinogen binding test $IC_{50}$ [µM] | Inhibition of platelet aggregation $EC_{50}$ [µM] |
|---|---|---|
| 1 | 0.510 | 0.240 |
| 1 (1) | 0.076 | 0.095 |
| 1 (13) | 0.270 | 0.320 |
| 1 (30) | 0.210 | 0.640 |
| 1 (5) | 0.078 | 0.250 |
| 1 (23) | 0.067 | 0.098 |
| 1 (19) | 0.200 | 0.390 |
| 4 | 0.270 | 0.360 |
| 2 (15) | 38 | >10 |
| 3 (7) | 0.270 | 0.110 |
| 2 (11) | 33 | 0.420 |
| 4 (6) | 13 | 0.280 |
| 4 (7) | 18 | 0.100 |
| 4 (8) | 0.170 | 0.120 |
| 4 (9) | 4.700 | 0.160 |
| 4 (10) | 0.590 | 0.091 |
| 4 (11) | 19 | 0.110 |
| 4 (12) |  | 0.290 |
| 4 (13) | 0.310 | 0.130 |
| 3 (11) | 0.630 | 0.980 |
| 22 (8) | 0.027 | 0.100 |
| 24 (1) | 0.012 | 0.094 |

The compounds of Examples 4(6) to 4(13) furthermore display high plasma levels of the corresponding acid (see Example 1(23)) over a period of more than 8 hours after peroral administration of 1 mg/kg to Rhesus monkeys.

The new compounds are tolerated well since, for example, no toxic side effects were observed after intravenous administration of 200 mg/kg of the compound according to the invention of Example 1(23) to mice.

On the basis of their inhibiting action on cell/cell and cell/matrix interactions, the new piperazine derivatives of the general formula I and their physiologically tolerated salts are suitable for combating or preventing diseases in which smaller or larger cell aggregates occur or cell/matrix interactions play a role, for example in combating or preventing venous and arterial thromboses, cerebrovascular diseases, pulmonary embolisms, cardiac infarction, arteriosclerosis, osteoporosis and the metastasing of tumours, and treatment of genetically caused or else acquired disturbances in the interactions of cells with one another or with solid structures. They are furthermore suitable for concomitant treatment of thrombolysis with fibrinolytics or vascular interventions, such as transluminal angioplasty, or else in the treatment of states of shock, psoriasis, diabetes and inflammations.

The dose for combating or preventing the abovementioned diseases is between 0.1 mg and 30 mg/kg of body weight, preferably 1 mg to 15 mg/kg of body weight, with up to 4 administrations per day. For this, the compounds of the formula I prepared according to the invention can be incorporated, if appropriate in combination with other active substances, such as thromboxane receptor antagonists and thromboxane synthesis inhibitors or combinations thereof, serotonin antagonists, α-receptor antagonists, alkyl nitrates, such as glycerol trinitrate, phosphodiesterase inhibitors, prostacyclin and analogues thereof, fibrinolytics, such as tPA, prourokinase, urokinase or streptokinase, or anticoagulants, such as heparin, dermatan sulphate, activated protein C, vitamin K antagonists, hirudin, inhibitors of thrombin or other activated coagulation factors, together with one or more inert customary carriers and/or diluents, for example with maize starch, lactose, sucrose, microcrystalline cellulose, magnesium stearate, polyvinylpyrrolidone, citric acid, tartaric acid, water, water/ethanol, water/glycerol, water/sorbitol, water/polyethylene glycol, propylene glycol, stearyl alcohol, carboxymethylcellulose or fat-containing substances, such as hard fat, or suitable mixtures thereof, into the customary pharmaceutical formulations, such as tablets, coated tablets, capsules, powders, suspensions, solutions, sprays or suppositories.

The following examples are intended to illustrate the invention in more detail:

PREPARATION OF THE STARTING COMPOUNDS:

EXAMPLE I

Methyl 4-amino-piperidin-1-ylacetate dihydrochloride a) 4-tert-Butyloxycarbonylamino-N-benzyl-piperidine A solution of 60 g (0.276 mol) of di-tert-butyl dicarbonate in 150 ml of dry dioxane is added dropwise to a solution of 50 g (0.26 mol) of 4-amino-1-benzyl-piperidine in 300 ml of dry dioxane, while stirring and cooling. When the addition has ended, the mixture is stirred at room temperature for 4 hours and is concentrated to dryness in vacuo. The residue which remains is triturated with a little ether and petroleum ether, filtered off with suction and washed with petroleum ether.

Yield: 70.6 g (92.60% of theory), Melting point: 114–115° C.; $R_f$ value: 0.60 (silica gel; methylene chloride/methanol=9:1)

b) 4-tert-Butyloxycarbonylamino-piperidine

A solution of 5 g (0.017 mol) of 4-tert-butyloxycarbonylamino-N-benzyl-piperidine in 50 ml of methanol is acidified to pH 6 with ethereal hydrochloric acid and hydrogenated exhaustively over palladium-on-charcoal (10%) under a hydrogen pressure of 50 psi at room temperature. The catalyst is filtered off, the filtrate is concentrated to dryness in vacuo, the residue is triturated with ether and the solid is filtered off with suction.

Yield: 3.3 g (95.7% of theory), Mass spectrum: $M^+=200$; $R_f$ value: 0.13 (silica gel; methylene chloride/methanol=9:1)

c) Methyl 4-tert-butyloxycarbonylamino-piperidin-1-yl acetate

A solution of 3.0 g (0.013 mol) of 4-tert-butyloxycarbonyl-amino-piperidine, 1.9 g (0.13 mol) of methyl bromoacetate (1.2 ml) and 2.6 g (0.025 mol) of triethylamine (3.4 ml) is stirred overnight at room temperature. It is then concentrated to dryness in vacuo and the residue is partitioned between ethyl acetate and water. The organic phase is dried over sodium sulphate and concentrated.

Yield: 3.1 g (89.8% of theory), Mass spectrum: $M^+=272$; $R_f$ value: 0.43 (silica gel; methylene chloride/methanol=9:1)

d) Methyl 4-aminopiperidin-1-yl acetate dihydrochloride

A solution of 3.1 g (0.011 mol) of methyl 4-tert-butyloxycarbonyl-amino-piperidine acetate in 30 ml of methanol is acidified with 30 ml of ethereal hydrochloric acid and left to stand overnight at room temperature. It is then concentrated to dryness in vacuo, the residue is triturated with ether and the solid is filtered off with suction.

Yield: 2.4 g (100% of theory), Mass spectrum: M$^+$=140; R$_f$ value: 0.10 (silica gel; methylene chloride/methanol=9:1)

EXAMPLE II

Methyl 3-(4-piperidinyl)-propionate a) 3-(4-Piperidinyl)-propionic acid 50 g (0.335 mol) of 3-(4-pyridyl)-acrylic acid are hydrogenated in 800 ml of 50% strength acetic acid with the addition of 10 g of platinum dioxide as the catalyst at room temperature under a hydrogen pressure of 50 psi until the uptake of hydrogen has ended. After the catalyst has been filtered off, the filtrate is concentrated to dryness in vacuo and the residue which remains is crystallized from a little methanol, after addition of ether.

Yield: 47 g (89.2% of theory), Mass spectrum: M$^+$=157 b) Methyl 3-(4-piperidinyl)-propionate 46.7 g (0.39 mol) of thionyl chloride are slowly added to 500 ml of methanol at −20° C., while stirring. When the addition has ended, the mixture is stirred for a further 20 minutes and 56.1 g (0.357 mol) of 3-(4-piperidinyl)-propionic acid are then slowly added, also at −20° C. The mixture is stirred at −20° C for a further hour and the temperature is then allowed to rise to room temperature overnight, with further stirring. The clear solution thus obtained is concentrated to dryness in vacuo and the residue is crystallized from acetone.

Yield: 57 g (77.2% of theory); Mass spectrum: M$^+$=171

EXAMPLE III

Methyl N-[4-nitrophenyloxycarbonyl]-3-(4-piperidinyl)-propionate 8 ml (0.0573 mol) of triethylamine are added dropwise to a solution of 4.75 g (0.0229 mol) of methyl 3-(4-piperidinyl)-propionate and 4.93 g (0.0229 mol) of p-nitrophenyl chloroformate in 200 ml of dry tetrahydrofuran at 0° C., while stirring, and the mixture is stirred overnight at room temperature. It is then heated at room temperature for 4 hours and concentrated to dryness in vacuo. The residue is partitioned between methylene chloride and water and the organic phase is separated off, dried and concentrated. The residue which remains is purified over a silica gel column, methylene chloride being used as the eluting agent.

Yield: 9 g of an oil, which contains 4-nitrophenol as an impurity. Mass spectrum: M$^+$=336; R$_f$ value: 0.93 (silica gel; methylene chloride/methanol=9:1)

EXAMPLE IV

Methyl N-(4-nitrophenyloxycarbonyl)-4-(4-piperidinyl)-butyrate

Prepared from methyl 4-(4-piperidinyl)-butyrate hydrochloride, p-nitrophenyl chloroformate and N-ethyldiisopropylamine analogously to Example III. Oil which crystallizes slowly.

R$_f$ value: 0.11 (silica gel; methylene chloride/methanol= 9:1)

EXAMPLE V

N-tert-Butyloxycarbonyl-N-(4-piperidinyl)-β-alanine methyl ester hydrochloride a) N-[1-Benzyl-4-piperidinyl]-β-alanine methyl ester hydrochloride A solution of 50 g (0.263 mol) of 4-amino-1-benzyl-piperidine and 28.5 ml (0.263 mol) of ethyl acrylate in 300 ml of methanol is heated at the reflux temperature for 4 hours. It is then concentrated to dryness in vacuo, the residue is dissolved in acetone and the solution is acidified to pH 3 with ethereal hydrochloric acid and concentrated to dryness again in vacuo. The residue which remains is triturated with acetone. The crystalline product which has separated out is filtered off with suction and dried.

Yield: 48.7 g (50.2% of theory), Melting point: 172–180° C. (decomposition); R$_f$ value: 0.60 (silica gel; methylene chloride/methanol=9:1)

b) N-[1-Benzyl-4-piperidinyl]-N-tert-butyloxycarbonyl-β-alanine methyl ester hydrochloride A solution of 25 g (0.0716 mol) of N-[1-benzyl-4-piperidinyl]-β-alanine methyl ester hydrochloride, 15.8 g (0.072 mol) of di-tert-butyl dicarbonate and 20 ml (0.138 mol) of triethylamine in 100 ml of dioxane and 100 ml of water is left to stand at room temperature for 48 hours. It is then concentrated to dryness in vacuo and the residue is partitioned between ethyl acetate and water. The organic phase is dried over sodium sulphate and concentrated. The residue which remains is dissolved in ethanol and acidified to pH 6 with ethereal hydrochloric acid. The solution is concentrated to dryness in vacuo, the residue is stirred with acetone and the solid is filtered off with suction.

Yield: 24.1 g (81.5% of theory), Melting point: 196–197° C. (decomposition); R$_f$ value: 0.80 (silica gel; methylene chloride/methanol=9:1)

c) N-tert-Butyloxycarbonyl-N-(4-piperidinyl)-β-alanine methyl ester hydrochloride 24 g (0.05 mol) of N-[1-benzyl-4-piperidinyl]-N-tert-butyloxycarbonyl-β-alanine methyl ester hydrochloride are hydrogenated exhaustively in 900 ml of methanol at room temperature under a hydrogen pressure of 50 psi over palladium-on-charcoal (10%) as the catalyst. The catalyst is filtered off with suction and the solution is concentrated to dryness in vacuo.

Yield: 20.4 g of an oil, R$_f$ value: 0.17 (silica gel; methylene chloride/methanol=9:1)

EXAMPLE VI

N-tert-Butyloxycarbonyl-N-(4-piperidinyl)-glycine methyl ester hydrochloride a) N-[1-Benzyl-4-piperidinyl]-glycine methyl ester dihydrochloride Prepared from 4-amino-1-benzyl-piperidine, methyl bromoacetate and N-ethyl-diisopropylamine.

b) N-[1-Benzyl-4-piperidinyl]-N-tert-butyloxycarbonyl-glycine methyl ester dihydrochloride Prepared from N-[1-benzyl-4-piperidinyl]-glycine methyl ester hydrochloride, di-tert-butyl dicarbonate and triethylamine.

c) N-tert-Butyloxycarbonyl-N-(4-piperidinyl)-glycine methyl ester hydrochloride

Prepared from N-[1-benzyl-4-piperidinyl]glycine methyl ester hydrochloride by exhaustive hydrogenation over palladium-on-charcoal (10%).

EXAMPLE VII

N-Methyl-N-(4-piperidinyl)-β-alanine methyl ester dihydrochloride a) N-[1-Benzyl-4-piperidinyl]-N-methyl-β-alanine methyl ester dihydrochloride A suspension of 28.8 g (0.026 mol) of N-[1-benzyl-4-piperidinyl]-β-alanine methyl ester dihydrochloride, 2.7 g (0.09 mol) of paraformaldehyde and 5.2 g (0.083 mol) of sodium cyanoborohydride in 100 ml of ethanol is stirred at room temperature for 24 hours. It is then diluted with water and acidified to pH 2 with 1N hydrochloric acid. The mixture is extracted with ethyl acetate and the aqueous phase is rendered alkaline with dilute sodium hydroxide solution and extracted exhaustively with methylene chloride. The combined methylene chloride phases are dried and concentrated to dryness in vacuo. The residue is purified over a silica gel column, methylene chloride with 3% and with 5% of methanol being used as the eluting agent. The combined eluates are acidified to pH 3 with ethereal hydrochloric acid and concentrated to dryness in vacuo. Acetone is added to the residue and the solid is filtered off with suction.

Yield: 20.8 g (69.5% of theory); Melting point: 224–227° C.; $R_f$ value: 0.60 (silica gel; methylene chloride/methanol=4:1)

b) N-Methyl-N-(4-piperidinyl)-β-alanine methyl ester dihydro-chloride

Prepared by hydrogenation of N-[1-benzyl-4-piperidinyl]-N-methyl-β-alanine methyl ester dihydrochloride with palladium-on-charcoal (10%).

Yield: 15.8 g (95.4% of theory); Melting point: 194–195° C. (decomposition); $R_f$ value: 0.09 (silica gel; methylene chloride/methanol=9:1)

The following compound can be prepared analogously to Example VII:

(1) N-Methyl-N-(4-piperidinyl)-glycine methyl ester dihydrochloride a) N-[1-Benzyl-4-piperidinyl]-N-methyl-glycine methyl ester dihydrochloride Prepared from N-[1-benzyl-4-piperidinyl]glycine methyl ester dihydrochloride, paraformaldehyde and sodium cyanoborohydride.

b) N-Methyl-N-(4-piperidinyl)-glycine methyl ester dihydrochloride

Prepared from N-[1-benzyl-4-piperidinyl]-N-methyl-glycine methyl ester dihydrochloride by exhaustive hydrogenation over palladium-on-charcoal (10%).

EXAMPLE VIII

N-Acetyl-N-(4-piperidinyl)-β-alanine methyl ester hydrochloride a) N-Acetyl-N-[1-benzyl-4-piperidinyl]-β-alanine methyl ester hydrochloride A solution of 25 g (0.0716 mol) of N-(1-benzyl-4-piperidinyl)-β-alanine methyl ester hydrochloride, 20 ml (0.143 mol) of triethylamine and 8.1 ml (0.0859 mol) of acetic anhydride in 300 ml of methanol is left to stand overnight at room temperature and is then concentrated in vacuo. The residue is dissolved in water and the solution is brought to pH 8 with 2N sodium hydroxide solution and extracted exhaustively with ethyl acetate. The combined ethyl acetate extracts are dried and concentrated to dryness in vacuo. The residue is purified over a silica gel column with methylene chloride which contains 3% of methanol. The eluates are concentrated, the residue is dissolved in acetone and the solution is acidified to pH 6 with ethereal hydrochloric acid and concentrated. The residue is made to crystallize with acetone/ether.

Yield: 19 g (74.7% of theory), Melting point: 138–140° C. (decomposition); $R_f$ value: 0.50 (silica gel; methylene chloride/methanol=9:1)

b) N-Acetyl-N-(4-piperidinyl)-β-alanine methyl ester hydrochloride

Preparated analogously to Example Vc by hydrogenation with palladium-on-charcoal (10%).

Yield: 13.2 g (93.2% of theory), Highly hygroscopic solid; Mass spectrum: M$^+$=228; $R_f$ value: 0.09 (silica gel; methylene chloride/methanol=9:1)

EXAMPLE IX

N-Acetyl-N-(4-piperidinyl)-glycine methyl ester hydrochloride a) N-Acetyl-N-[1-benzyl-4-piperidinyl]-glycine methyl ester hydrochloride Prepared from N-[1-benzyl-4-piperidinyl]glycine methyl ester hydrochloride and acetic anhydride.

b) N—Acetyl-N-(4-piperidinyl)-glycine methyl ester hydrochloride

Prepared from N-acetyl-N-[1-benzyl-4-piperidinyl]glycine methyl ester hydrochloride by exhaustive hydrogenation over palladium-on-charcoal (10%).

EXAMPLE X

3-[4-[4-(1-Benzyl)-piperidinyl]-piperazin-1-yl] propionic acid dihydrochloride a) Methyl 3-[4-(1-benzyl)-piperazin-1-yl]propionate dihydrochloride Prepared from N-benzyl-piperazine and methyl acrylate analogously to Example Va.

Yield: 14.7 g (71.5% of theory), Mass spectrum: M$^+$=262; $R_f$ value: 0.42 (silica gel; methylene chloride/methanol/concentrated ammonia=9:1:0.1)

b) Methyl 3-(piperazin-1-yl)-propionate dihydrochloride

Prepared from methyl 3-[4-(1-benzyl)-piperazin-1-yl] propionate dihydrochloride by hydrogenation over palladium-on-charcoal (10%) analogously to Example Vc.

Yield: 10.5 g (99% of theory), Mass spectrum: M$^+$=172; $R_f$ value: 0.13(silica gel; methylene chloride/methanol/concentrated ammonia=9:1:0.1)

c) Methyl 3-[4-[4-(1-benzyl)-piperidinyl]-piperazin-1-yl] propionate

About 4 g of molecular sieve 3 Å are added to a solution of 1.9 g (0.01 mol) of N-benzyl-4-piperidone (1.9 ml) and 2.5 g (0.01 mol) of methyl 3-(piperazin-1-yl)-propionate dihydrochloride in 200 ml of methanol. 1.2 g (0.03 mol) of sodium cyanoborohydride are added and the mixture is stirred overnight at room temperature. Thereafter, the molecular sieve is filtered off with suction and the solution is concentrated to dryness in vacuo. The residue which remains is partitioned between ethyl acetate and water. The ethyl acetate solution is dried and concentrated to dryness in vacuo. The residue which remains is purified over a silica gel column, methylene chloride/methanol=20:1 and methylene chloride/methanol/concentrated ammonia=9:1:0.1 being used as the eluting agent.

Yield: 2 g of an oil (57.7% of theory), $R_f$ value: 0.25 (silica gel; methylene chloride/methanol/concentrated ammonia=9:1:0.1)

d) 3-[4-[4-(1-Benzyl)-piperidinyl]-piperazin-1-yl]propionic acid dihydrochloride Prepared from methyl 3-[4-[4-(1-benzyl)-piperidinyl]-piperazin-1-yl]propionate and half-concentrated hydrochloric acid analogously to Example 1.

Yield: 2.2 g (94.0% of theory), Mass spectrum: M$^+$=331; $R_f$ value: 0.17 (silica gel; methylene chloride/methanol/concentrated ammonia=4:1:0.1)

EXAMPLE XI

4-[4-[(1-Benzyl)-piperidinyl]piperazin-1-yl]acetic acid a) Methyl (4-benzyl-piperazin-1-yl)-acetate A solution of 6 g (0.034 mol) of N-benzyl-piperazine (6 ml), 5.2 g (0.034 mol) of methyl bromoacetate (3.3 ml) and 3.5 g (0.034 mol) of triethylamine (4.8 ml) in 100 ml of methanol is left to stand overnight at room temperature. The solution is then concentrated to dryness in vacuo and the residue is purified over a silica gel column (eluting agent: methylene chloride which contains 2% of methanol).

Yield: 7 g of an oil (82.8% of theory), $R_f$ value: 0.60 (silica gel; methylene chloride/methanol/concentrated ammonia=9:1:0.1)

b) Methyl piperazinoacetate dihydrochloride 7 g (0.028 mol) of methyl (4-benzyl-piperazin-1-yl)-acetate are hydrogenated exhaustively in 100 ml of methanol, which contains 1 ml of ethereal hydrochloric acid, over palladium-on-charcoal (10%) as the catalyst at room temperature under a hydrogen pressure of 50 psi. When the uptake of hydrogen has ended and the catalyst has been removed, the mixture is concentrated to dryness.

Yield: 4.5 g of an amorphous solid (100% of theory), $R_f$ value: 0.26 (silica gel; methylene chloride/methanol/concentrated ammonia=9:1:0.1)

c) Methyl 4-[4-(1-benzyl)-piperidinyl]-piperazinoacetate

A solution of 4.5 g (0.028 mol) of methyl piperazinoacetate dihydrochloride and 5.4 g (0.028 mol) of N-benzyl-4-piperidone (5.3 ml) in 100 ml of dry methanol is acidified to pH 6 with ethereal hydrochloric acid. 1.8 g (0.028 mol) of sodium cyanoborohydride and about 4 g of molecular sieve 3 Å are added to this solution at room temperature, while stirring, and stirring is continued overnight. After the molecular sieve has been filtered off, the solution is concentrated to dryness in vacuo and the residue is partitioned between ethyl acetate and water. The combined organic phases are dried and concentrated to dryness in vacuo. The residue which remains is purified over a silica gel column (eluting agent: methylene chloride/methanol/concentrated ammonia=30:1:0.1).

Yield: 6.4 g (81.2% of theory), Mass spectrum: $M^+=331$; $R_f$ value: 0.65 (silica gel; methylene chloride/methanol/concentrated ammonia=9:1:0.1)

d) 4-[4-[(1-Benzyl)-piperidinyl]piperazin-1-yl]acetic acid 2 g (0.047 mol) of lithium hydroxide are added to a solution of 3.1 g (0.0094 mol) of methyl 4-[4-(1-benzyl)-piperidinyl]piperazinoacetate in 30 ml of tetrahydrofuran and 35 ml of water and the mixture is stirred at room temperature for 6 hours. Thereafter, 2.5 g (0.047 mol) of ammonium chloride are added and the solution is concentrated to dryness in vacuo. The residue is extracted twice with absolute ethanol. The combined ethanol extracts are evaporated to dryness in vacuo. The residue which remains is purified over a silica gel column (eluting agent: methylene chloride/methanol/concentrated ammonia=4:1:0.1).

Yield: 2 g (67.4% of theory), Mass spectrum: $M^+=317$; $R_f$ value: 0.35 (silica gel; methylene chloride/methanol/concentrated ammonia=4:1:0.2)

EXAMPLE XII

N-[4-(1-tert-Butyloxycarbonyl)-piperidinyl]-piperazine a) 1-Benzyl-4-[4-(1-tert-butyloxycarbonyl)-piperidinyl]-piperazine Prepared from N-tert-butyloxycarbonyl-4-piperidone, N-benzyl-piperazine and sodium cyanoborohydride analogously to Example XIc.

Yield: 4.8 g (83.1% of theory), $R_f$ value: 0.45 (silica gel; methylene chloride/methanol=9:1)

b) N-[4-(1-tert-Butyloxycarbonyl)-piperidinyl]piperazine

Prepared from 1-benzyl-4-[4-(1-tert-butyloxycarbonyl)-piperidinyl]piperazine by hydrogenation with palladium dihydroxide-on-charcoal as the catalyst analogously to Example 3.

Yield: 3.0 g (83.3% of theory), $R_f$ value: 0.13 (silica gel; methylene chloride/methanol=9:1)

EXAMPLE XIII

[4-[(4-(1-tert-Butyloxycarbonyl)-piperidinyl] piperazin-1-yl]-malonic acid a) Ethyl [4-[4-(1-tert-butyloxycarbonyl)-piperidinyl]-piperazin-1-yl]malonate A solution of 2.8 g (0.0104 mol) of N-[4-(1-tert-butyloxycarbonyl)-piperidinyl]piperazine, 1.8 g (0.0104 mol) of malonic acid monoethyl ester potassium salt, 3.3 g (0.0104 mol) of 2-(1H-benzotriazol-1-yl)-1,1,3,3-tetramethyluronium tetrafluoroborate, 1.4 g (0.0104 mo) of 1-hydroxy-1-H-benzotriazole and 1 g (0.01 mol) of N-methyl-morpholine in 100 ml of dry dimethylformamide is left to stand overnight at room temperature. The solution is then concentrated to dryness in vacuo and the residue is purified by chromatography over a silica gel column (eluting agent: methylene chloride which contains 2% and 4% of methanol).

Yield: 1.5 g (37.1% of theory), $R_f$ value: 0.45 (silica gel; methylene chloride/methanol=9:1)

b) [4-[(4-(1-tert-Butyloxycarbonyl)-piperidinyl]piperazin-1-yl]malonic acid 5 ml of a 1N sodium hydroxide solution (0.042 mol) are added to a solution of 1.5 g (0.039 mol) of ethyl [4-[(4-(l-tert-butyloxycarbonyl)-piperidinyl]piperazin-1-yl]malonate in 50 ml of methanol and the mixture is left to stand at room temperature for 24 hours. Thereafter, 5 ml of a 1N hydrochloric acid are added and the solution is concentrated to dryness in vacuo. Absolute ethanol is added to the residue, and the mixture is concentrated in vacuo, 3 times. Thereafter, the residue is stirred with a mixture of absolute ethanol and methylene chloride (1:1), the undissolved inorganic salts are filtered off with suction and the solution is concentrated to dryness in vacue.

Yield: 1.2 g of a foamy substance (87.4% of theory), $R_f$ value: 0.11 (silica gel; methylene chloride/methanol=4:1)

EXAMPLE XIV

[4-[4-(4-(1-tert-Butyloxycarbonyl)-piperidinyl)-piperazin-1-yl]carbonylamino]piperidine a) N-Benzyl-[4-[4-(4-(1-tert-butyloxycarbonyl)-piperidinyl)-piperazin-1-yl]carbonylamino]piperidine Prepared from 4-amino-N-benzyl-piperidine, N-[4-(1-tert-butyloxycarbonyl)-piperidinyl]-piperazine, N,N'-carbonyldiimidazole and imidazole analogously to Example 6.

Yield: 5.7 g (63.8% of theory), $R_f$ value: 0.40 (silica gel; methylene chloride/methanol/concentrated ammonia=9:1:0.1)

b) [4-[4-(4-(1-tert-Butyloxycarbonyl)-piperidinyl)-piperazin-1-yl]carbonylamino]piperidine Prepared from N-benzyl-[4-[4-(4-(1-tert-butyloxycarbonyl)-piperidinyl)-piperazin-1-yl] carbonylamino]piperidine by hydrogenation over palladium dihydroxide-on-charcoal analogously to Example 3.

Yield: 4.3 g (92.6% of theory), $R_f$ value: 0.11 (silica gel; methylene; chloride/methanol/concentrated ammonia=9:1:0.1)

EXAMPLE XV

Methyl 4-(4-piperidinyl)-butyrate hydrochloride a) Diethyl 2-[2-(4-pyridyl)-ethyl]malonate hydrochloride 13.4 g (0.583 mol) of sodium are dissolved in 180 ml of absolute ethanol, and 204 ml (1.35 mol) of diethyl malonate are added in portions to the solution thus formed, a colourless precipitate forming. This precipitate is dissolved by heating to 30–40° C. and diluting with absolute ethanol, and a solution of 63 ml (0.583 mol) of 4-vinylpyridine in 120 ml of absolute ethanol is added dropwise in the course of 1.5 hours, while stirring. When the addition has ended, the mixture is heated at the reflux temperature for 3 hours and then concentrated to a small volume and diluted with 450 ml of half-concentrated hydrochloric acid. It is extracted twice with ether in order to remove excess diethyl malonate and the aqueous phase is rendered alkaline with sodium carbonate and extracted exhaustively with methylene chloride. The combined organic phases are dried and concentrated. The residue is purified over a silica gel column, ethyl acetate/cyclohexane=1:1 being used as the eluting agent. The oily residue (78.6 g=50.8% of theory) is dissolved in acetone and the solution is acidified to pH 3.5 with ethereal hydrochloric acid and concentrated. The residue crystallizes overnight and is triturated with acetone/ether and filtered off with suction.

Yield: 65 g (37% of theory), $R_f$ value: 0.80 (silica gel; methylene chloride/methanol=9:1)

b) Diethyl 2-[2-(4-piperidinyl)-ethyl]malonate hydrochloride 64.5 g (0.21 mol) of diethyl 2-[2-(4-pyridyl)-ethyl] malonate hydrochloride are hydrogenated exhaustively in 400 ml of absolute ethanol at room temperature under a hydrogen pressure of 50 psi over platinum dioxide as the catalyst. After the catalyst has been filtered off with suction, the solution which remains is concentrated to dryness in vacuo. The residue is brought to crystallization with acetone and is filtered off with suction.

Yield: 62.8 g (95.5% of theory) of highly hygroscopic crystals which deliquesce in air, $R_f$ value: 0.22 (silica gel; methylene chloride/methanol=9:1)

c) 4-(4-Piperidinyl)-butyric acid hydrochloride

A solution of 62 g (0.201 mol) of diethyl 2-[2-(4-piperidinyl)-ethyl]-malonate hydrochloride in 600 ml of concentrated hydrochloric acid is heated at the reflux temperature for 24 hours and then concentrated to dryness in vacuo. Toluene is added to the residue and the mixture is concentrated. This operation is repeated three more times.

Yield: 44.3 g of colourless crystals which still contain a little toluene, $R_f$ value: 0.19 (silica gel; methylene chloride/methanol=9:1)

d) Methyl 4-(4-piperidinyl)-butyrate hydrochloride 18 ml (0.242 mol) of thionyl chloride are slowly added dropwise to 800 ml of methanol at −10° C., while stirring. A solution of 44.3 g (0.201 mol) of 4-(4-piperidinyl)-butyric acid hydrochloride in 100 ml of methanol is then added dropwise at the same temperature, stirring is continued overnight at room temperature and the mixture is then concentrated to dryness in vacuo. The residue is partitioned between 50% strength potassium carbonate solution and ether. The aqueous phase is extracted twice more with ether. The combined ether extracts are dried and concentrated. The residue is dissolved in methanol and the solution is acidified to pH 6 with ethereal hydrochloric acid and concentrated to dryness in vacuo. The residue which remains is triturated with acetone. The crystals which have separated out are filtered off with suction.

Weight: 35.5 g (88.7% of theory); Melting point: 99–105° C. (decomposition)

EXAMPLE XVI

Methyl 4-piperidinyloxyacetate hydrochloride
a) Methyl N-tert-butyloxycarbonyl-4-piperidinyloxyacetate 2.3 g (0.05 mol) of sodium hydride (50% strength in oil) are added to a solution of 10 g (0.05 mol) of N-tert-butyloxycarbonyl-4-piperidinol in 100 ml of dry tetrahydrofuran, while stirring, and the mixture is stirred for a further 2 hours. 7.6 g (0.05 mol) of methyl bromoacetate (5 ml) are then added dropwise, while stirring further, and stirring is continued overnight. The unreacted sodium hydride is destroyed by addition of water. The mixture is extracted with ethyl acetate and the combined ethyl acetate extracts are dried and concentrated to dryness in vacuo. The residue is purified over a silica gel column (eluting agent: methylene chloride which contains 1% of methanol).

Yield: 4.9 g (36.1% of theory), Mass spectrum: $M^+$=273; $R_f$ value: 0.50 (silica gel; methylene chloride/methanol=9.5:0.5)

b) Methyl 4-piperidinyloxyacetate hydrochloride 30 ml of ethereal hydrochloric acid are added to a solution of 4.9 g (0.018 mol) of methyl N-tert-butyloxycarbonyl-4-piperidinyloxyacetate in 10 ml of methanol and the mixture is left to stand at room temperature for 4 hours. It is then concentrated to dryness in vacuo, ether is added to the residue and the solid is filtered off with suction.

Yield: 3.1 g of a colourless solid (82.5% of theory), Mass spectrum: $M^+$=173; $R_f$ value: 0.10 (silica gel; methylene chloride/methanol=9:1)

EXAMPLE XVII

α-Bromo-4-methoxycarbonylmethyloxy-acetophenone a) 4-Methoxycarbonylmethyloxy-acetophenone 9 g (0.06 mol) of methyl bromoacetate (5.6 ml) and 8 g (0.06 mol) of potassium carbonate are added to a solution of 8 g (0.06 mol) of 4-hydroxy-acetophenone in 100 ml of dry dimethylformamide. The mixture is heated at the reflux temperature for 5 hours and then stirred overnight at room temperature. The solution is concentrated to dryness in vacuo and the residue is partitioned between ethyl acetate and water. The combined organic extracts are dried and concentrated to dryness in vacuo. The residue is triturated with ether, filtered off with suction and dried.

Yield: 8.6 g of an amorphous solid (70.3% of theory), Mass spectrum: $M^+$=208; $R_f$ value: 0.45 (silica gel; ethyl acetate/cyclohexane=1:1)

b) α-Bromo-4-methoxycarbonylmethyloxy-acetophenone

A suspension of 0.0106 mol of bromodioxane (prepared from 1.7 g of bromine and 8 ml of dioxane) in dioxane is added dropwise to a solution of 2 g (0.0096 mol) of 4-methoxycarbonylmethyloxy-acetophenone in 40 ml of ether and 10 ml of dioxane at room temperature, while stirring. When the addition has ended, the mixture is stirred at room temperature for a further 2 hours and then concentrated to dryness in vacuo.

Yield: 1.3 g of crude product, $R_f$ value: 0.60 double spot (silica gel; ethyl acetate/cyclohexane=1:1)

The following compound can be prepared analogously to Example XVII:

(1) Methyl 4-(α-bromo-acetyl)-phenylacetate

Prepared from methyl 4-acetyl-phenylacetate and bromodioxane.

EXAMPLE XVIII

3-Methoxycarbonylmethyloxy-aniline
a) 3-Methoxycarbonylmethyloxy-nitrobenzene 8.8 g (0.065 mol) of potassium carbonate are added to a solution of 9 g (0.065 mol) of m-nitrophenol in 100 ml of dry dimethylformamide and the mixture is stirred at room temperature for ½ hour. 10.9 g (0.07 mol) of methyl bromoacetate (6.7 ml) are then added and the mixture is heated at 80° C. for 5 hours. The solution is then concentrated to dryness in vacuo and the residue is partitioned between ethyl acetate and water. The combined organic phases are dried and concentrated to dryness in vacuo. The residue is triturated with ether, filtered off with suction and dried.

Yield: 9.2 g (67.3% of theory), $R_f$ value: 0.55 (silica gel; methylene chloride)

b) 3-Methoxycarbonylmethyloxy-aniline 9.2 g (0.046 mol) of 3-methoxycarbonylmethoxy-nitrobenzene are hydrogenated exhaustively in methanol over 1.5 g of Raney nickel under a hydrogen pressure of 50 psi at room temperature. After the catalyst has been filtered off with suction, the solution is concentrated.

Yield: 7.0 g of an oil (88.7% of theory), $R_f$ value: 0.50 (silica gel; ethyl acetate/cyclohexane=1:1)

EXAMPLE XIX

4-Methyloxycarbonylmethyloxy-aniline a) 4-Methoxycarbonylmethyloxy-nitrobenzene

Prepared from 4-nitrophenol, methyl bromoacetate and caesium carbonate analogously to Example XVIIIa.

Yield: 10.4 g (91.2% of theory), Melting point: 86–88° C.

b) 4-Methoxycarbonylmethyloxy-aniline

Prepared from 4-methoxycarbonylmethyloxy-nitrobenzene by hydrogenation over Raney nickel analogously to Example XVIIIb.

Yield: 9.5 g of a resin (98.4% of theory), $R_f$ value: 0.60 (silica gel; methylene chloride/methanol=9:1)

EXAMPLE XX

Methyl 3-(4-amino-phenyl)-propionate hydrochloride 12.96 g (0.11 mol) of thionyl chloride (7.93 ml) are added dropwise to a solution of 15 g (0.0991 mol) of 3-(4-amino-phenyl)-propionic acid in 100 ml of methanol, while stirring and cooling with methanol/ice. When the addition has ended, the mixture is stirred for a further 30 minutes, while cooling, and is then stirred overnight at room temperature. It is then concentrated to dryness in vacuo and the residue is crystallized from methanol/ether.

Yield: 16.8 g (85.6% of theory), Melting point: 165–167° C.

EXAMPLE XXI 4-(Ethoxycarbonyl-2-ethyloxy)-piperidine trifluoroacetate a) 4-(Ethoxycarbonyl-2-ethyloxy)-N-tert-butyloxycarbonyl-piperidine 0.3 g (0.0027 mol) of potassium tert-butylate is added to a solution of 10 g (0.0497 mol) of N-tert-butyloxycarbonyl-4-piperidinol in 20 ml of dioxane, 13.5 ml (0.124 mol) of ethyl acrylate are then added dropwise, while stirring, and the mixture is heated at the reflux temperature for 7 hours. After the mixture has been stirred overnight at room temperature, it is concentrated to dryness in vacuo and the residue is partitioned between ethyl acetate and water. The organic phase is dried and concentrated to dryness in vacuo. The residue is purified over a silica gel column (eluting agent: cyclohexane/ethyl acetate=10:3).

Yield: 4.5 g of an oil (30% of theory), $R_f$ value: 0.80 (silica gel; methylene chloride/methanol=9:1)

b) 4-(Ethoxycarbonyl-2-ethyloxy)-piperidine trifluoroacetate 4.5 g (0.015 mol) of 4-(ethoxycarbonyl-2-ethyloxy)-N-tert-butyloxycarbonyl-piperidine are left to stand in a mixture of 30 ml of methylene chloride and 20 ml of trifluoroacetic acid at room temperature for 4 hours. The mixture is concentrated to dryness in vacuo and 4.5 g of a colourless oil are obtained.

$R_f$ value: 0.20 (silica gel; methylene chloride/methanol=9:1)

EXAMPLE XXII

Dimethyl 4-amino-1,2-phenylenedioxy-diacetate hydrochloride a) Dimethyl 4-nitro-1,2-phenylenedioxy-diacetate A solution of 10 g (0.0645 mol) of 4-nitrobenzocatechol, 12.8 ml (0.135 mol) of methyl bromoacetate and 18.7 g (0.135 mol) of potassium carbonate in 100 ml of dimethylformamide is heated at 80° C. for 5 hours. After cooling, the residue is partitioned between water and ethyl acetate and the organic phase is dried and concentrated in vacuo. The residue is triturated with ether and filtered off with suction.

Yield: 11.4 g (59% of theory), $R_f$ value: 0.90 (silica gel; methylene chloride)

b) Dimethyl 4-amino-1,2-phenylenedioxy-diacetate hydrochloride 11.4 g (0.0381 mol) of dimethyl 4-nitro-1,2-phenylenedioxy-diacetate are hydrogenated exhaustively in 160 ml of methanol and 40 ml of 1N hydrochloric acid at room temperature under a hydrogen pressure of 50 psi over palladium-on-charcoal (10%) as the catalyst. After the catalyst has been filtered off with suction, the solution which remains is concentrated to dryness in vacuo. The residue is triturated with acetone and filtered off with suction.

Yield: 10.6 g (93.9% of theory), $R_f$ value: 0.70 (silica gel; methylene chloride/methanol=9:1)

EXAMPLE XXIII

Ethyl 3-(4-amino-phenyloxy)-propionate hydrochloride a) Ethyl 3-(4-nitro-phenyloxy)-propionate A mixture of 10 g (0.0719 mol) of p-nitrophenol, 2 ml of Triton B and 20 ml (0.1797 mol) of methyl acrylate is heated at the reflux temperature for 20 hours and then concentrated to dryness under reduced pressure. The residue is partitioned between water and ethyl acetate. The organic phase is then dried and concentrated to dryness under reduced pressure. The residue is chromatographed over a silica gel column, methylene chloride being used as the eluting agent. The residue which remains is triturated with petroleum ether and filtered off with suction.

Melting point: 50–53° C.; $R_f$ value: 0.65 (silica gel; methylene chloride)

b) Ethyl 3-(4-amino-phenyloxy)-propionate hydrochloride

Prepared from ethyl 3-(4-nitro-phenyloxy)-propionate by exhaustive hydrogenation analogously to Example XXIIb, ethanol being used as the solvent.

$R_f$ value: 0.75 (silica gel; methylene chloride/methanol=9:1)

EXAMPLE XXIV

4-[2-(Ethoxycarbonyl-ethyl)-oxy]-benzoic acid a) Benzyl 4-[2-(ethoxycarbonyl-ethyl)-oxy]-benzoate A mixture of 10 g (0.0438 mol) of benzyl 4-hydroxy-benzoate, 12 ml (0.1095 mol) of methyl acrylate and 2 ml of Triton B is heated at the reflux temperature for 20 hours. After the mixture has been concentrated under reduced pressure, the residue is partitioned between water and ethyl acetate. The organic phase is dried and concentrated and the residue is purified over a silica gel column, methylene chloride being used as the eluting agent. Oil.

$R_f$ value: 0.85 (silica gel; methylene chloride/methanol= 9:1)

b) 4-[2-(Ethoxycarbonyl-ethyl)-oxy]-benzoic acid Prepared from benzyl 4-[2-(ethoxycarbonyl-ethyl)-oxy]-benzoate by exhaustive hydrogenation analogously to Example XXIIb, ethanol being used as the solvent.

Melting point: 141-1430° C., $R_f$ value:0.50 (silica gel; methylene chloride/methanol=9:1)

EXAMPLE XXV

4-[[4-[4-(1-Benzyl)-piperidinyl]-piperazin-1-yl]-carbonyl]-aniline a) 4-[[4-[4-(1-Benzyl)-piperidinyl)-piperazin-1-yl]-carbonyl]-tert-butyloxycarbonyl-aniline Prepared from 4-tert-butyloxycarbonylamino-benzoic acid, (4-(1-benzyl)-piperidinyl)-piperazine dihydrochloride, triethylamine and 2-(lH-benzotriazol-1-yl)-1,1,3,3-tetramethyluronium tetrafluoroborate analogously to Example XIIIa.

Melting point: 270-276° C. (decomposition)

b) 4-[[4-[4-(1-Benzyl)-piperidinyl]-piperazin-1-yl]-carbonyl]-aniline

Prepared from 4-[[4-[4-(1-benzyl)-piperidinyl]-piperazin-1-yl]-carbonyl]-tert-butyloxycarbonyl-aniline and 50% strength trifluoroacetic acid in methylene chloride analogously to Example 2. Foam. $R_f$ value: 0.11 (silica gel; methylene chloride/methanol=9:1)

EXAMPLE XXVI

3-[[4-(4-(1-tert-Butyloxycarbonyl)-piperidinyl)-piperazin-1-yl]carbonyl]-aniline a) 3-[[4-(4-(1-tert-Butyloxycarbonyl)-piperidinyl)-piperazin-1-yl]carbonyl]-nitrobenzene Prepared from 4-[(1-tert-butyloxycarbonyl)-piperidinyl]-piperazine hydrochloride, 3-nitro-benzoic acid, triethylamine and 2-(lH-benzotriazol-1-yl)-1,1,3,3-tetramethyluronium tetrafluoroborate analogously to Example XIIIa. Yellow foam. $R_f$ value: 0.45 (silica gel; methylene chloride/methanol =9:1)

b) 3-[[4-(4-(1-tert-Butyloxycarbonyl)-piperidinyl)-piperazin-1-yl]carbonyl]-aniline Prepared from 3-[[4-(4-(1-tert-butyloxycarbonyl)-piperidinyl)-piperazin-1-yl]carbonyl]-nitrobenzene by exhaustive hydrogenation analogously to Example XXIIb. Foam.

$R_f$ value: 0.35 (silica gel; methylene chloride/methanol/concentrated ammonia=95:5:0.5)

EXAMPLE XXVII

3-[2-(Ethoxycarbonyl-ethyl)-oxy]-benzoic acid a) Benzyl 3-F2-(ethoxycarbonyl-ethyl)-oxy]-benzoate Prepared from benzyl 3-hydroxy-benzoate, ethyl acrylate and Triton B analogously to Example 8.

$R_f$ value: 0.90 (silica gel; methylene chloride/methanol= 9:1)

b) 3-[2-(Ethoxycarbonyl-ethyl)-oxy]-benzoic acid

Prepared from benzyl 3-[2-(ethoxycarbonyl-ethyl)-oxy]-benzoate by exhaustive hydrogenation analogously to Example XXIIb, ethanol being used as the solvent.

Melting point: 88–90° C.

EXAMPLE XXVIII

3-[(4-Methoxycarbonylmethyl)-piperidinyl]-propionic acid hydrochloride a) tert-Butyl 3-[(4-methoxycarbonylmethyl)-piperidinyl]-propionate Prepared from methyl 4-piperidinyl-acetate hydrochloride, tert-butyl acrylate and Triton B analogously to Example 8.

$R_f$ value: 0.75 (silica gel; methylene chloride/methanol= 9:1)

b) 3-[[4-Methoxycarbonylmethyl)-piperidinyl]-propionic acid hydrochloride

Prepared from tert-butyl 3-[[4-methoxycarbonylmethyl)-piperidinyl]-propionate and 50% strength trifluoroacetic acid in methylene chloride analogously to Example 2. $R_f$ value: 0.25 (silica gel; methylene chloride/methanol=9 :1)

EXAMPLE XXIX

3-[4-[(4-(1-tert-Butyloxycarbonyl)-piperidinyl)-pipera-zin-1-yl]]-propionic acid a) Ethyl 3-[4-[(4-(1-tert-butyloxycarbonyl)-piperidinyl)-piperazin-1-yl]]-propionate Prepared from [4-(1-tert-butyloxycarbonyl)-piperidinyl]-piperazine hydrochloride, ethyl acrylate and Triton B analogously to Example 8.

$R_f$ value: 0.60 (silica gel; methylene chloride/methanol= 9:1)

b) 3-[4-[(4-(1-tert-Butyloxycarbonyl)-piperidinyl)-piperazin-1-yl]]-propionic acid Prepared from ethyl 3-[4-[[4-(1-tert-butyloxycarbonyl)-piperidinyl)-piperazin-1-yl]]-propionate and 1N sodium hydroxide solution analogously to Example XIIIb.

$R_f$ value: 0.10 (silica gel; methylene chloride/methanol= 9:1)

EXAMPLE XXX

Methyl [4-trans-[2S-(4-piperazinyl)-propionyl] amino-cyclohexanecarboxylate a) Methyl 4-trans-(N-tert-butyloxycarbonyl-L-alanyl)-amino-cyclohexanecarboxylate 1.8 ml (0.0145 mol) of isobutyl chloroformate are added to a solution of 2.5 g (0.013 mol) of N-tert-butyloxycarbonyl-L-alanine and 3.9 ml (0.028 mol) of triethylamine in 100 ml of dry dimethylformamide at -50° C., while stirring, and stirring is continued at room temperature for one hour. 2.6 g (0.013 mol) of methyl 4-amino-cyclohexanecarboxylate hydrochloride are then added and the mixture is left to stand overnight. After the mixture has been concentrated and the residue has been partitioned between water and ethyl acetate, the organic phase is dried and concentrated to dryness again. The residue is crystallized from ether/petroleum ether.

Yield: 3.47 g (80% of theory), Melting point: 136–137° C. $R_f$ value: 0.60 (silica gel; methylene chloride/methanol=9:1)

b) Methyl 4-trans-(L-alanyl)-amino-cyclohexanecarboxylate trifluoroacetate

Prepared from 3.4 g (0.01 mol) of methyl 4-trans-(tert-butyloxycarbonyl-L-alanyl)-amino-cyclohexanecarboxylate and 50% strength trifluoroacetic acid in methylene chloride analogously to Example 2.

Yield: 6 g of an oily crude product. $R_f$ value: 0.28 (silica gel; methylene chloride/methanol=9:1)

c) Methyl 4-trans-[2S-(4-(1-benzyl-piperazinyl))-propionyl] amino-cyclohexanecarboxylate A solution of the crude residue from Example XXXb (0.01 mol), 14 ml (0.08 mol) of N-ethyl-diisopropylamine and 2.8 g (0.01 mol) of N-benzyl-N,N-bis-(2-chloroethyl)-amine hydrochloride in 40 ml of ethanol is heated at the reflux temperature for 20 hours. The solution is then concentrated under reduced pressure and the residue is partitioned between water and ethyl acetate. The residue which remains after drying and concentration is purified by means of chromatography over a silica gel column, methylene chloride which contains 8% of methanol and 0.8% of concentrated ammonia being used as the eluting agent.

Yield: 2.1 g of an oily product (52.1% of theory), $R_f$ value: 0.55 (silica gel; methylene chloride/methanol=9:1)

d) Methyl 4-trans-[2S-(4-piperazinyl)-propionyl]amino-cyclohexanecarboxylate

Prepared by exhaustive hydrogenation of 2.05 g (0.0053 mol) of methyl 4-trans-[2S-(4-(1-benzyl-piperazinyl))-propionyl]aminocyclohexanecarboxylate with palladium-on-charcoal (10%) analogously to Example 3.

Yield: 1.4 g (88.8% of theory) of an oily product, $R_f$ value: 0.10 (silica gel; methylene chloride/methanol=9:1)

EXAMPLE XXXI

Methyl 4-trans-[2S-(4-piperazinyl)-3-(4-methoxyphenyl)propionyl]amino-cyclohexanecarboxylate a) Methyl 4-trans-(N-tert-butyloxycarbonyl-O-methyl-L-tyrosyl)-amino-cyclohexane carboxylate Prepared from N-tert-butyloxycarbonyl-O-methyl-L-tyrosine, methyl 4-amino-cyclohexanecarboxylate hydrochloride, isobutyl chloroformate and triethylamine analogously to Example XXXa.

Melting point: 151–1530C., $R_f$ value: 0.70 (silica gel; methylene chloride/methanol=9:1)

b) Methyl 4-trans-(O-methyl-L-tyrosyl)-amino-cyclohexane-carboxylate trifluoroacetate Prepared from methyl 4-trans-(N-tert-butyloxycarbonyl-O-methyl-L-tyrosyl)-amino-cyclohexanecarboxylate and 50% strength trifluoroacetic acid in methylene chloride analogously to Example 2.

$R_f$ value: 0.40 (silica gel; methylene chloride/methanol=9:1)

c) Methyl 4-trans-[2S-(1-benzyl-piperazin-4-yl)-3-(4-methoxy-phenyl)-propionyl]-amino-cyclohexanecarboxylate Prepared from methyl 4-trans-[(O-methyl-L-tyrosyl)-amino]-cyclohexanecarboxylate trifluoroacetate, N-ethyl-diisopropylamine and N-benzyl-N,N-bis-(2-chloroethyl)-amine hydrochloride analogously to Example XXXc.

Melting point: $R_f$ value:

d) Methyl 4-trans-[2S-(4-piperazinyl)-3-(4-methoxyphenyl)-propionyl]amino-cyclohexanecarboxylate Prepared by exhaustive hydrogenation of methyl 4-trans-[2S-(4-(1-benzylpiperazinyl))-3-(4-methoxyphenyl)-propionyl]-amino]-cyclohexanecarboxylate with palladium-on-charcoal (10%) analogously to Example 3.

Melting point: $R_f$ value: 0.25 (silica gel; methylene chloride/methanol/concentrated ammonia=9:1:0.1)

EXAMPLE XXXII

Methyl N-[2S-(4-piperazinyl)-propionyl]-4-piperidinyloxy-acetate a) Methyl N-(tert-butyloxycarbonyl-L-alanyl)-4-piperidinyloxy-acetate Prepared from N-tert-butyloxy-L-alanine, methyl 4-piperidinyloxyacetate hydrochloride, isobutyl chloroformate and triethylamine analogously to Example XXXa.

b) Methyl N-(L-alanyl)-4-piperidinyloxyacetate trifluoroacetate

Prepared from methyl N-(tert-butyloxycarbonyl-L-alanyl)-4-piperidinyloxyacetate and trifluoroacetic acid in methylene chloride analogously to Example 2.

c) Methyl N-[2S-(4-(1-benzyl-piperazinyl))propionyl]-4-piperidinyloxyacetate

Prepared from methyl N-[L-alanyl)-4-piperidinyloxyacetate trifluoroacetate, N-ethyl-diisopropylamine and N-benzyl-N,N-bis-(2-chloroethyl)-amine hydrochloride analogously to Example XXXc.

d) Methyl N-[2S-(4-piperazinyl)propionyl]-4-piperidinyloxy-acetate

Prepared by exhaustive hydrogenation of methyl N-[2S-(4-(1-benzyl-piperazinyl))-propionyl]-4-piperidinyloxy acetate with palladium-on- charcoal (10%) analogously to Example 3.

EXAMPLE XXXIII

Methyl N-[2S-(4-piperazinyl)-3-(4-methoxyphenyl)-propionyl]-4-piperidinyloxyacetate a) Methyl N-(tert-butyloxycarbonyl-O-methyl-L-tyrosyl)-4-piperidinyloxyacetate Prepared from N-tert- butyloxycarbonyl-O-methyl-L-tyrosine, methyl 4-piperidinyloxyacetate hydrochloride and isobutyl chloroformate with triethylamine analogously to Example XXXa.

b) Methyl N-(O-methyl-L-tyrosyl)-4-piperidinyloxy acetate trifluoroacetate

Prepared from methyl N-(tert-butyloxycarbonyl-O-methyl-L-tyrosyl)-4-piperidinyloxyacetate and 50% strength trifluoroacetic acid in methylene chloride analogously to Example 2.

c) Methyl N-[2S-(4-(1-benzyl-piperazinyl))-3-(4-methoxyphenyl-propionyl]-4-piperidinyloxyacetate Prepared from methyl N-(O-methyl-L-tyrosyl)-4-piperidinyloxy-acetate trifluoroacetate, N-ethyl-diisopropylamine and N-benzyl-N,N-bis-(2-chloroethyl)-amine hydrochloride analogously to Example XXXa.

d) Methyl N-[2S-(4-piperazinyl)-3-(4-methoxyphenyl)-propionyl]-4-piperidinyloxyacetate Prepared by exhaustive hydrogenation of methyl N-[2S-(4-piperazinyl)-3-(4-methoxyphenyl)-propionyl]-4-piperidinyloxyacetate with palladium-on-charcoal (10%) analogously to Example 3.

EXAMPLE XXXIV

[4-(4-(1-tert-Butyloxycarbonyl)-piperidinyl)-piperazin-1-yl]-oxalic acid a) Methyl [4-(4-(1-tert-butyloxycarbonyl)-piperidinyl)-piperazin-1-yl]-oxalate 2 g (16.3 mmol) of oxalic acid methyl ester chloride are added dropwise to a suspension of 5 g (16.3 mmol) of 4-(1-tert-butyloxycarbonyl)-piperidinyl]-piperazine hydrochloride and 4.6 ml (32.7 mmol) of triethylamine in 50 ml of dry tetrahydrofuran, while stirring and cooling with ice. The mixture is then stirred at room temperature for a further 4 hours. It is evaporated to dryness under reduced pressure and the residue is partitioned between water and ethyl acetate. The organic phase is dried over sodium sulphate and evaporated to dryness under reduced pressure.

Yield: 5.8 g of an oil (99.8% of theory) $R_f$ value: 0.47 (silica gel; methylene chloride/methanol/concentrated ammonia=9:1:0.1)

b) [4-(4-(1-tert-Butyloxycarbonyl)-piperidinyl)-piperazin-1-yl]-oxalic acid 49 ml of a 1N sodium hydroxide solution are added to a solution of 5.8 g (16.3 mmol) of methyl [4-(4-(1-tert-butyloxycarbonyl)-piperidinyl)-piperazin-1-yl]-oxalate in 100 ml of tetrahydrofuran and the mixture is stirred at room temperature for 3 hours. 49 ml of 1N hydrochloric acid are then added and the mixture is concentrated to dryness under reduced pressure. Absolute ethanol is added to the residue and the mixture is concentrated to dryness again. The residue is purified by means of chromatography over silica gel, methylene chloride/methanol/concentrated ammonia= 4:1:0.2 being used as the eluting agent.

Yield: 3.0 g (53.9% of theory), $R_f$ value: 0.25 (silica gel; methylene chloride/methanol/concentrated ammonia= 4:1:0.2); Mass spectrum: $M^+$=341

EXAMPLE XXXV

4-Methoxycarbonylmethyloxy-phenylacetic acid
a) Benzyl 4-methoxycarbonylmethyloxy-phenylacetate After stirring a suspension of 8.4 g (0.035 mol) of benzyl 4-hydroxy-phenylacetate and 4.8 g (0.035 mol) of dried potassium carbonate in 100 ml of dimethylformamide at room temperature for 45 minutes, 5.3 g (0.038 mol) of methyl bromoacetate are slowly added and the mixture is then heated at 80° C. for 5 hours, with further stirring. Thereafter, stirring is continued overnight at room temperature. The solid is filtered off and the mother liquor is concentrated to dryness under reduced pressure. The residue is purified over a silica gel column, methylene chloride being used as the eluting agent.

Yield: 7.9 g of an amorphous solid (72.9% of theory)
b) 4-Methoxycarbonylmethyloxy-phenylacetic acid 7.8 g (0.025 mol) of benzyl 4-methoxycarbonylmethyloxy-phenyl-acetate are hydrogenated exhaustively in 150 ml of methanol in the presence of 8 g of palladium hydroxide-on-charcoal at room temperature under a hydrogen pressure of 50 psi. After removal of the catalyst, the mother liquor is concentrated to dryness under reduced pressure. 4.7 g (89.5% of theory) of a resinous crude product remain.

EXAMPLE XXXVI

1-Iodo-2-(4-methoxycarbonylmethyloxyphenyl)-ethane
a) 2-(4-Methoxycarbonylmethyloxyphenyl)-ethanol Prepared from 2-(4-hydroxyphenyl)-ethanol, potassium carbonate and methyl bromoacetate analogously to Example XXXVa.
b) 1-Iodo-2-(4-methoxycarbonylmethyloxyphenyl)-ethane 5.5 g (21.6 mmol) of iodine are added to a solution of 4.16 g (19.6 mmol) of 2-(4-methoxycarbonylmethyloxyphenyl)-ethanol, 5.7 g (21.6 mmol) of triphenylphosphine and 1.84 g (29.3 mmol) of imidazole in 200 ml of toluene at room temperature, while stirring, and stirring is continued at room temperature for one hour. A precipitate separates out and is filtered off with suction and discarded. The mother liquor is concentrated to dryness under reduced pressure and the residue is heated with petroleum ether. The triphenyl oxide which has precipitated out is filtered off with suction and the mother liquor is concentrated to dryness again. A crude oil remains.

Yield: 2.8 9 (55% of theory).

EXAMPLE XXXVII

N-Benzyl-N-[4-trans-[4-(4-(1-tert-butyloxycarbonyl)-piperidinyl)-piperazin-1-yl]carbonylaminocyclohexyl]- amine
a) 4-trans-Benzyloxycarbonylaminocyclohexyl isocyanate 2.9 g (10.8 mmol) of diphenylphosphoryl azide are added to a solution of 3 g (10.8 mmol) of 4-trans-benzyloxycarbonylaminocyclohexylcarboxylic acid and 1.1 g (10.8 mmol) of triethylamine in 30 ml of dioxane and the mixture is heated at the reflux temperature for 5 hours. After cooling, it is concentrated to dryness under reduced pressure. The crude product (3.1 g) is used further without further purification.
b) N-[4-trans-[4-(4-(1-tert-Butyloxycarbonyl)-piperidinyl)-piperazin-1-yl]carbonylaminocyclohexyl]-benzyloxycarbonylamine A solution of 3 g (10.8 mmol) of crude 4-trans-benzyloxycarbonylaminocyclohexyl isocyanate, 3.3 g (10.8 mmol) of [4-(1-tert-butyloxycarbonyl)-piperidinyl]-piperazine hydrochloride and 1.1 g (10.8 mmol) of triethylamine in 10 ml of dioxane is left to stand at room temperature for 60 hours. It is then concentrated to dryness under reduced pressure and the residue is purified by chromatography over silica gel, methylene chloride/methanol 9:1 being used as the eluting agent.

Yield: 4.1 g (69% of theory), $R_f$ value: 0.50 (silica gel; methylene chloride/methanol =9:1)
c) N-[4-trans-[4-(4-(1-tert-Butyloxycarbonyl)-piperidinyl)-piperazin-1-yl]carbonylaminocyclohexyl]-amine4.1 g (7.5 mmol) of N-[4-trans-[4-(4-(1-tert-butyloxycarbonyl)-piperidinyl)-piperazin-1-yl]carbonylaminocyclohexyl]-benzyloxycarbonylamine are hydrogenated exhaustively in 100 ml of methanol over palladium-on-charcoal (10%).

3.3 g of an amorphous solid (100of theory)

$R_f$ value: 0.10 (silica gel; methylene chloride/methanol/concentrated ammonia=9:1:0.1)
d) N-Benzyl-N-[4-trans-[4-(4-(1-tert-butyloxycarbonyl)-piperidinyl)-piperazin-1-yl]carbonylaminocyclohexyl]-amine 3.3 g (8.1 mmol) of N-[4-trans-[4-(4-(1-tert-butyloxycarbonyl)-piperidinyl)-piperazin-1-yl]carbonylaminocyclohexyl]-amine are hydrogenated exhaustively together with 0.9 g (8.1 mmol) of benzaldehyde in 100 ml of methanol over Raney nickel at 50° C. under a hydrogen pressure of 50 psi. The crude product is purified by chromatography over silica gel, methylene chloride/methanol/concentrated ammonia=100:4.5:0.45 being used as the eluting agent.

Yield: 2.1 g (52.2% of theory), $R_f$ value: 0.65 (silica gel; methylene chloride/methanol/concentrated ammonia= 4:1:0.2)

EXAMPLE XXXVIII

Butyl 2-(4-isocyanato-phenoxy) acetate

A solution of 40 g (0.154 mmol) of benzyl 2-(4-aminophenoxy) acetate in 450 ml of toluene is slowly added to 240 ml (0.462 mmol) of a 1.93 molar solution of phosgene in toluene at 0° C., while cooling and stirring. When the addition has ended, the cooling is interrupted and the reaction solution is heated under reflux in an oil bath. After 3.5 hours, the oil bath is switched off and the solution is subsequently stirred overnight, during which it slowly comes to room temperature. Thereafter, the toluene is distilled off in vacuo. Yield: 43.7 g of a crude oil (100% of theory)

EXAMPLE XXXIX

Benzyl 2-(4-aminophenoxy)acetate
a) Benzyl 2-(4-nitrophenoxy)acetate 27.6 g (0.2 mol) of 4-nitrophenol are dissolved in 300 ml of dimethylformamide and, after addition of 27.6 g (0.2 mol) of dried potassium carbonate, the mixture is stirred at room temperature for 45 minutes. Thereafter, 50.4 g (0.22 mol= 34.9 ml) of benzyl bromoacetate are added dropwise, while stirring, and the suspension is then heated at 80° C. (oil bath temperature) for 5 hours. The oil bath is then switched off and the suspension is stirred for a further 15 hours, during which the reaction mixture slowly comes to room temperature. The undissolved inorganic salts are filtered off with suction and the mother liquor is concentrated to dryness in vacuo. The residue is dissolved in methylene chloride and, after washing twice with water, the solution is dried over sodium sulphate, filtered and concentrated. The product obtained is suspended in ether and filtered off with suction.
Yield: 55.4 g (96.4% of theory).
b) Benzyl 2-(4-aminophenoxy)acetate 27.0 g (0.094 mmol) of benzyl 2-(4-nitrophenoxy)acetate are dissolved in 1200 ml of methanol and hydrogenated in the presence of 5 g of rhodium-on-charcoal with hydrogen at room temperature under 3 bar. After about 2 hours, the uptake of hydrogen has ended and, after the catalyst has been filtered off with suction, the mother liquor is concentrated to dryness in vacuo. The residue is suspended in about 300 ml of methylene chloride and, after filtration, the filtrate is concentrated to dryness.
Yield: 19.9 g of an oil (82.3% of theory).

EXAMPLE XL

N-(1-Benzyl-3-pyrrolidinyl)-piperazine dihydrochloride a) N-(1-Benzyl-3-pyrrolidinyl)-N-ethoxycarbonyl-piperazine hydrochloride 14.5 g of sodium triacetoxyborohydride are added in portions to a solution of 9.4 g of 1-benzyl-3-pyrrolidinone, 8.8 g of ethyl piperazine-N-carboxylate and 3.0 ml of glacial acetic acid in 100 ml of tetrahydrofuran. The suspension is stirred at room temperature for 16 hours. Sodium carbonate solution is added and the aqueous phase is extracted with ethyl acetate. The organic phase is dried over sodium sulphate. After addition of a little methanol, a pH of 3 is established with ethereal hydrochloric acid and the solvent is evaporated off under reduced pressure. The residue is triturated with acetone and filtered off with suction.
Yield: 15.4 g (87% of theory), $R_f$ value: 0.56 (silica gel; methylene chloride/methanol/concentrated ammonia= 9:1:0.1)
b) N-(1-Benzyl-3-pyrrolidinyl)-piperazine dihydrochloride A solution of 21.4 g of N-(1-benzyl-3-pyrrolidinyl)-N-ethoxycarbonyl-piperazine hydrochloride in 200 ml of concentrated hydrochloric acid is heated at 130° C. in an autoclave for 8 hours. The solution is filtered over active charcoal and the solvent is evaporated off under reduced pressure. The residue is triturated with acetone and filtered off with suction.
Yield: 16.5 g (91% of theory), $R_f$ value: 0.58 (silica gel; methylene chloride/methanol/concentrated ammonia= 4:1:0.25)

EXAMPLE XLI 1-(3-Ethoxycarbonyl-propyl)-piperidin-4-yl-carboxylic acid a) Benzyl 1-(3-ethoxycarbonyl-propyl)-piperidin-4-yl-carboxylate A solution of 2.2 g of benzyl 4-piperidinylcarboxylate, 1.95 g of ethyl 4-bromobutyrate and 2.22 g of triethylamine in 25 ml of chloroform is heated under reflux for 3 hours. 0.5 ml of ethyl 4-bromobutyrate is added and the mixture is heated for a further 3 hours. The reaction solution is partitioned between methylene chloride and 0.5M sodium hydroxide solution. The organic phase is extracted with saturated sodium chloride solution and dried over sodium sulphate. The solvent is evaporated off under reduced pressure and the residue is chromatographed over silica gel with methylene chloride/methanol/concentrated ammonia (9:1:0.1).
Yield: 2.7 g (81% of theory) of an oil, $R_f$ value: 0.14 (silica gel; ethyl acetate/cyclohexane=1:2)
b) 1-(3-Ethoxycarbonyl-propyl)-piperidin-4-yl-carboxylic acid A solution of 2.7 g of benzyl 1-(3-ethoxycarbonyl-propyl)-piperidin-4-ylcarboxylate in 40 ml of ethanol is hydrogenated in the presence of 0.4 g of palladium-on-charcoal under a pressure of 50 psi at room temperature. The catalyst is filtered off and the solvent is evaporated off under reduced pressure. The residue is chromatographed over silica gel with methylene chloride/methanol/concentrated ammonia (4:1:0.2).
Yield: 1.7 g (85% of theory), $R_f$ value: 0.10 (silica gel; methylene chloride/methanol/concentrated ammonia 4:1:0.2)

EXAMPLE XLII

4-[2-(Carboxy)-ethyl]-1-[(ethoxycarbonyl)-methyl]-piperidine a) 4-[2-(Benzyloxycarbonyl)-ethyl]-piperidine 9.7 g of 4-(2-carboxyethyl)-piperidine hydrochloride (melting point 240–250° C., prepared by hydrogenation of 3-(4-pyridyl)-acrylic acid in glacial acetic acid in the presence of platinum oxide and subsequent treatment with hydrochloric acid), 30 ml of benzyl alcohol, 3 g of p-toluenesulphonic acid and 50 ml of toluene are heated for 1.5 hours using a water separator. The reaction mixture is concentrated under reduced pressure. 50 ml of ice-water are added to the residue and the mixture is extracted with tert-butyl methyl ether. The aqueous phase is rendered alkaline and extracted with tert-butyl methyl ether. The extract is washed with sodium chloride solution and dried and the solvent is evaporated off under reduced pressure.
Yield: 9.0 g (73% of theory), $R_f$ value: 0.18 (silica gel; methylene chloride/methanol/concentrated ammonia= 95:5:1)
b) 4-[2-(Benzyloxycarbonyl)-ethyl]-1-[(ethoxycarbonyl)-methyl]-piperidine 6.35 g of ethyl bromoacetate in 20 ml of acetonitrile are added dropwise to 9.0 g of 4-[2-(benzyloxycarbonyl)-ethyl]-piperidine and 5.2 g of N-ethyl-diisopropylamine in 70 ml of acetonitrile, while stirring in an ice-bath, and the mixture is stirred at room temperature for 18 hours. The solvent is evaporated off under reduced pressure and the residue is partitioned rapidly between tert-butyl methyl ether, ice-water and 10 ml of 2N sodium hydroxide solution. The organic phase is washed with ice-water and saturated sodium chloride solution and dried and the solvent is evaporated off under reduced pressure.
Yield: 10.5 g (83% of theory), $R_f$ value: 0.84 (silica gel; methylene chloride/methanol/concentrated ammonia= 95:5:1)
c) 4-[2-(Carboxy)-ethyl]-1-[(ethoxycarbonyl)-methyl]-piperidine 10 g of 4-[2-(benzyloxycarbonyl)-ethyl]-1-[(ethoxycarbonyl)-methyl]-piperidine are hydrogenated in 150 ml of tetrahydrofuran at room temperature under a hydrogen pressure of 50 psi in the presence of 1.3 g of palladium-on-active charcoal for 4 hours. The solvent is evaporated off under reduced pressure and the residue is crystallized with diethyl ether and a little acetone.
Yield: 5.8 g (79% of theory), Melting point: 65–670° C.

EXAMPLE XLIII

4-[2-(Carboxy)-ethyl]-1-[(cyclohexyloxycarbonyl)-methyl]-pipe-ridine

The preparation is carried out analogously to Examples XLIIa to c. Instead of ethyl bromoacetate, cyclohexyl bromoacetate (boiling point: 102–104° C. under 16 mbar, prepared by reaction of bromoacetyl chloride with cyclohexanol in pyridine/ethyl acetate in the presence of a catalytic amount of 4-dimethylaminopyridine) is employed. Melting point: 85–88° C.

EXAMPLE XLIV trans-4-[[4-[1-(tert-Butyloxycarbonyl)-piperidin-4-yl]-piperazin-1-yl]-carbonyl]-cyclohexanecarboxylic acid ( a) Ethyl trans-4-[[4-[1-(tert-butyloxycarbonyl)-piperidin-4-yl]-piperazin-1-yl]-carbonyl]-cyclohexanecarboxylate 1.68 g of N-[1-(tert-butyloxycarbonyl)-piperidin-4-yl]-piperazine, 1.0 g of trans-4-cyclohexanedicarboxylic acid monoethyl ester, 1.93 g of 2-(1H-benzotriazol-1-yl)-1,1,3,3-tetramethyluronium tetrafluoroborate and 1.5 g of triethylamine are stirred in 40 ml of anhydrous dimethylformamide at room temperature for 16 hours. The reaction solution is evaporated under reduced pressure and the residue is partitioned between 0.5N sodium hydroxide solution and ethyl acetate. The organic phase is washed with saturated sodium chloride solution and dried and the solvent is evaporated off under reduced pressure. The residue is chromatographed over silica gel with methylene chloride/methanol/concentrated ammonia (20:1:0.1).

Yield: 2.1 g (95% of theory), $R_f$ value: 0.87 (silica gel; methylene chloride/methanol/concentrated ammonia= 4:1:0.2)

(b) trans-4-[[-4-[1-(tert-Butyloxycarbonyl)-piperidin-4-yl]-piperazin-1-yl]-carbonyl]-cyclohexanecarboxylic acid Prepared from ethyl trans-4-[[-4-[1-(tert-butyloxycarbonyl)-piperidin-4-yl]-piperazin-1-yl]-carbonyl]-cyclohexane-carboxylate by hydrolysis with lithium hydroxide analogously to Example 24. Mass spectrum: $(M+H)^+=424$; $R_f$ value: 0.24 (silica gel; methylene chloride/methanol/concentrated ammonia=4:1:0.2)

EXAMPLE XLV 1-(1-Benzyl-piperidin-4-yl)-4-[(piperidin-4-yl)-carbonyl]-piperazine trihydrochloride (a) 1-(1-Benzyl-piperidin-4-yl)-4-[[1-(tert-butyloxycarbonyl)-piperidin-4-yl]carbonyl]-piperazine Prepared analogously to Example XIIIa. The residue is chromatographed over silica gel with methylene chloride/methanol/concentrated ammonia (9:1:0.1). $R_f$ value: 0.40 (silica gel; methylene chloride/methanol/concentrated ammonia=9:1:0.1)

b) 1-(1-Benzyl-piperidin-4-yl)-4-[(piperidin-4-yl)-carbonyl]-piperazine trihydrochloride A suspension of 1.7 g of 1-(1-benzyl-piperidin-4-yl)-4-[[1-(tert-butyloxycarbonyl)-piperidin-4-yl]-carbonyl]-piperazine in 20 ml of dioxane, 400 ml of methanol and 50 ml of ethereal hydrochloric acid is stirred at room temperature for 1 hour. Water is added until a clear solution forms. After 2 hours, the solvent is evaporated off under reduced pressure and the residue is dried.

Yield: 1.8 g (100% of theory), Melting point: 326–330° C.; Mass spectrum: $M^+=370$; $R_f$ value: 0.52 (silica gel; methylene chloride/methanol/concentrated ammonia= 4:1:0.2)

EXAMPLE XLVI tert-Butyl [4-(aminomethyl)-piperidin-1-yl]acetate
(a) tert-Butyl [4-(aminocarbonyl)-piperidin-1-yl]acetate 9.0 g of piperidine-4-carboxylic acid amide, 11.3 g of tert-butyl bromoacetate and 10.4 g of potassium carbonate in 100 ml of acetone are stirred at room temperature for 4 hours. The solvent is evaporated off under reduced pressure and the residue is dissolved in water. The aqueous phase is extracted with ethyl acetate, the organic phase is dried and the solvent is evaporated off under reduced pressure. The crude product is chromatographed over silica gel with methylene chloride/methanol/concentrated ammonia (9:1:0.1).

Yield: 15.0 g (88% of theory), $R_f$ value: 0.47 (silica gel; methylene chloride/methanol/concentrated ammonia= 9:1:0.1)

b) tert-Butyl [4-(aminomethyl)-piperidin-1-yl]acetate

A solution of 2.42 g of tert-butyl [4-(aminocarbonyl)-piperidin-1-yl]acetate in 30 ml of tetrahydrofuran is added dropwise to 20 ml of a 1M solution of diborane in tetrahydrofuran and the mixture is heated under reflux for 4 hours. 10 ml of a 1M solution of diborane in tetrahydrofuran are added and the mixture is refluxed for a further 5 hours. Water is added and the mixture is extracted with ethyl acetate. The aqueous phase is evaporated under reduced pressure and the residue is chromatographed over silica gel with methylene chloride/methanol/concentrated ammonia (4:1:0.25).

Yield: 0.95 g (42% of theory), $R_f$ value: 0.11 (silica gel; methylene chloride/methanol/concentrated ammonia= 9:1:0.1)

EXAMPLE XLVII

Methyl [4-(carboxymethyloxy)-1-piperidyl]acetate
a) Methyl [4-(tert-butyloxycarbonyl-methyloxy)-1-piperidyl]-acetate 2.2 ml of methyl bromoacetate are added to a solution of 5.0 g of tert-butyl 4-piperidyloxyacetate and 3.9 ml of N-ethyl-diisopropylamine in 40 ml of methanol at 0° C. The mixture is stirred at 0° C. for 10 minutes and at room temperature for a further 72 hours. The solvent is evaporated off under reduced pressure and the crude product is chromatographed over silica gel with methylene chloride/methanol/concentrated ammonia (16:1:0.1).

Yield: 4.19 g (64% of theory), $R_f$ value: 0.11 (silica gel; methylene chloride/methanol/concentrated ammonia= 9:1:0.1)

b) Methyl [4-(carboxy-methyloxy)-1-piperidyl]acetate

A solution of 2.52 g of methyl [4-(tert-butyloxycarbonyl-methyloxy)-1-piperidyl]acetate in 10 ml of trifluoroacetic acid and 10 ml of methylene chloride is stirred at room temperature for 4 hours. The solvent is evaporated under reduced pressure. 8.8 ml of 1N hydrochloric acid are added to the residue and the mixture is evaporated again. After addition of 40 ml of acetone, a precipitate separates out and is filtered off with suction and dried.

Yield: 1.55 g (66% of theory), $R_f$ value: 0.21 (silica gel; methylene chloride/methanol/concentrated ammonia= 4:1:0.25)

EXAMPLE XLVIII

Ethyl 1- (2-amino-ethyl) -4-piperidinecarboxylate
a) Ethyl 1-[2-(dibenzylamino)-ethyl]-4-piperidinecarboxylate A solution of 4.6 ml of ethyl 4-piperidinecarboxylate, 9.07 g of N-(2-chloroethyl)-dibenzylamine and 10.3 ml of N-ethyl-diisopropylamine in 20 ml of methanol is heated under reflux for 5 hours. The solvent is evaporated off under reduced pressure and the crude product is chromatographed over silica gel with methylene chloride/methanol/concentrated ammonia (16:1:0.1).

Yield: 7.9 g (69% of theory), $R_f$ value: 0.64 (silica gel; methylene chloride/methanol/concentrated ammonia= 9:1:0.1)

b) Ethyl 1-(2-amino-ethyl)-4-piperidinecarboxylate hydrochloride

A solution of 7.9 g of ethyl 1-[2-(dibenzylamino)-ethyl]-4-piperidinecarboxylate in 100 ml of ethanol and 21 ml of 1N hydrochloric acid is hydrogenated with hydrogen at 50° C. under a pressure of 3 bar in the presence of 1.0 g of palladium-on-charcoal. The catalyst is filtered off and the solvent is evaporated under reduced pressure. The residue is triturated with acetone and filtered off with suction.

Yield: 3.5 g (71% of theory), Melting point: 128–130° C. $R_f$ value: 0.12 (silica gel; methylene chloride/methanol/concentrated ammonia=9:1:0.1)

EXAMPLE IL trans-4-[N-(tert-Butyloxycarbonylmethyl)-N-(phenylsulphonyl)-aminomethyl]-cyclohexanecarboxylic acid a) Methyl trans-4-(aminomethyl)-cyclohexanecarboxylate A solution of 15.7 g of trans-4-(aminomethyl)-cyclohexanecarboxylic acid in 150 ml of ethereal hydrochloric acid and 1000 ml of absolute methanol is stirred at room temperature for 20 hours. The solvent is evaporated off under reduced pressure and the residue is triturated with ether and filtered off with suction.

Yield: 19.6 g (94% of theory), Melting point: 178–180° C.

b) Methyl trans-4-[N-(phenylsulphonyl)-aminomethyl]-cyclohexanecarboxylate 9.7 g of benzenesulphonyl chloride are added dropwise to a solution of 10.4 g of methyl trans-4-(aminomethyl)-cyclohexane-carboxylate and 150 g of pyridine in 100 ml of tetrahydrofuran and the mixture is stirred at room temperature for 16 hours. The solution is evaporated under reduced pressure and the solid which remains is stirred with water, and filtered off with suction, several times.

Yield: 8.1 g (52% of theory), $R_f$ value: 0.64 (silica gel; methylene chloride/methanol/concentrated ammonia=9:1:0.1)

c) Methyl trans-4-[N-(tert-butyloxycarbonylmethyl)-N-(phenylsulphonyl)-aminomethyl]-cyclohexane-carboxylate A suspension of 3.11 g of methyl trans-4-[N-(phenylsulphonyl)-aminomethyl]-cyclohexane-carboxylate, 1.95 g of tert-butyl bromoacetate and 4.0 g of potassium carbonate in 50 ml of acetone is heated under reflux for 4 hours. A further 1.95 g of tert-butyl bromoacetate are added and the mixture is heated for a further 4 hours. The solid is filtered off with suction and the filtrate is evaporated under reduced pressure. The residue is partitioned between ethyl acetate/water. The organic phase is dried and evaporated. The crude product is chromatographed over silica gel with cyclohexane/ethyl acetate (4:1).

Yield: 3.9 g (91% of theory), Melting point: 119–121° C. $R_f$ value: 0.32 (silica gel; cyclohexane/ethyl acetate =4:1)

d) trans-4-[N-(tert-Butyloxycarbonylmethyl)-N-(phenylsulphonyl)-aminomethyl]-cyclohexanecarboxylic acid A solution of 2.13 g of methyl trans-4-[N-(tert-butyloxycarbonylmethyl)-N-(phenylsulphonyl)-aminomethyl]-cyclohexane-carboxylate and 0.63 g of lithium hydroxide hydrate in 40 ml of tetrahydrofuran and 50 ml of water is stirred at room temperature for 3 hours. The solution is neutralized with 1M hydrochloric acid and the tetrahydrofuran is evaporated off. The aqueous phase is extracted with ethyl acetate and the organic phase is dried and evaporated. The crude product is chromatographed over silica gel with cyclohexane/ethyl acetate (1:2).

Yield: 1.55 g (75% of theory), Melting point: 129–132° C. $R_f$ value: 0.59 (silica gel; cyclohexane/ethyl acetate=1:2)

EXAMPLE L

N-(1-Methyl-piperidin-4-yl)-piperazine

Prepared from N-methyl-piperid-4-one and N-benzyl-piperazine by reductive aminoalkylation with sodium cyanoborohydride in methanol and subsequent elimination of the benzyl protective group by hydrogenation with hydrogen in the presence of palladium-on-charcoal.

$R_f$ value: 0.20 (silica gel; methylene chloride/methanol/concentrated ammonia=4:1:0.25)

EXAMPLE LI tert-Butyl [1-(2-carboxy-ethyl)-4-hydroxy-piperidin-4-yl]-acetate a) tert-Butyl (1-benzyl-4-hydroxy-piperidin-4-yl)-acetate 8.9 ml of tert-butyl acetate are added dropwise to 42 ml of a 1.5 molar solution of lithium diisopropylamide in cyclohexane in 75 ml of absolute tetrahydrofuran at −70° C. The mixture is stirred at −700° C. for 10 minutes and 9.4 ml of N-benzyl-piperid-4-one are then added dropwise. After 30 minutes at −700° C., the cooling bath is removed and stirring is continued until room temperature is reached. The reaction solution is poured into 100 ml of water and the aqueous phase obtained is extracted several times with ethyl acetate. The combined organic phases are washed with saturated sodium chloride solution and dried over sodium sulphate and the solvent is evaporated off under reduced pressure.

Yield: 16.1 g (quantitative) of crude product, Melting point: 560° C. $R_f$ value: 0.49 (silica gel; methylene chloride/methanol/concentrated ammonia=9:1:0.1)

b) tert-Butyl (4-Hydroxy-piperidin-4-yl)-acetate

A solution of 1.6 g of tert-butyl (1-benzyl-4-hydroxy-piperidin-4-yl)-acetate in 20 ml of methanol is hydrogenated with hydrogen in the presence of 0.3 g of palladium-on-charcoal at 500° C. under a hydrogen pressure of 3 bar. The catalyst is then filtered off and the filtrate is evaporated under reduced pressure. The crude product is chromatographed over silica gel with methylene chloride/methanol/concentrated ammonia (9:1:0.1 to 4:1:0.25).

Yield: 0.98 g (88% of theory), Melting point: 97–990° C.; $R_f$ value: 0.42 (silica gel; methylene chloride/methanol/concentrated ammonia=4:1:0.25)

c) tert-Butyl [1-[2-(methoxycarbonyl)-ethyl]-4-hydroxy-piperidin-4-yl]-acetate

Prepared from tert-butyl 4-hydroxy-piperidin-4-yl)-acetate analogously to Example 8.

Yield: Quantitative, $R_f$ value: 0.55 (silica gel; methylene chloride/methanol/concentrated ammonia=9:1:0.1)

d) tert-Butyl [1-(2-carboxy-ethyl)-4-hydroxy-piperidin-4-yl]-acetate

Prepared from tert-butyl [1-[2-(methoxycarbonyl)-ethyl]-4-hydroxy-piperidin-4-yl]-acetate analogously to Example 22.

Yield: Quantitative, Mass spectrum: M=287; $R_f$ value: 0.25 (silica gel; methylene chloride/methanol/concentrated ammonia=4:1:0.25)

Preparation of the End Products:

EXAMPLE 1

[4-trans-[3-[4-(4-Piperidinyl)-piperazin-1-yl] propionyl]-amino]cyclohexanecarboxylic acid dihydrochloride A solution of 0.22 g (0.00058 mol) of methyl [4-trans-[3-[4-(piperidinyl)-piperazin-1-yl]propionyl]amino]

cyclohexane-carboxylate in 20 ml of half-concentrated hydrochloric acid is left to stand at room temperature for 4 hours and then concentrated to dryness in vacuo. Acetone is added to the residue which remains and the mixture is concentrated to dryness again. The residue is triturated with acetone, filtered off with suction and dried.

Yield: 0.21 g (82.7% of theory), Melting point: 286–288° C. $R_f$ value: 0.10 (silica gel; methylene chloride/methanol/concentrated ammonia=2:1:0.25)

The following compounds can be prepared analogously to EXAMPLE 1:

(1) [3-[4-trans-[4-(4-Piperidinyl)-piperazin-1-yl] carbonylamino]cyclohexyl]propionic acid dihydrochloride Prepared from methyl [3-[4-trans-[4-[4-(piperidinyl)-piperazin-1-yl]carbonylamino]cyclohexyl]propionate dihydrochloride.

Melting point: 318–320° C. Mass spectrum: $M^+=366$ $R_f$ value: 0.10 (silica gel; methylene chloride/methanol/concentrated ammonia=4:1:0.2)

(2) [4-trans-[4-(4-Piperidinyl)-piperazin-1-yl] malonylamino]-cyclohexanecarboxylic acid dihydrochloride Prepared from methyl [4-trans-[4-(piperidinyl)-piperazin-1-yl]-malonylamino]cyclohexanecarboxylate dihydrochloride.

Melting point: 256–258° C.; Mass spectrum: $M^+=380$; $R_f$ value: 0.07 (silica gel; methylene chloride/methanol/concentrated ammonia=4:1:0.2)

(3) 3-[4-[4-(4-Piperidinyl)-piperazin-1-yl]carbonylamino] piperidino-propionic acid dihydrochloride Prepared from methyl 3-[4-[4-(4-piperidinyl)-piperazin-yl]carbonylamino]piperidino-propionic piperidinopropionate dihydrochloride.

Melting point: 281–283° C.; Mass spectrum: $M^+=335$; $R_f$ value: 0.10 (silica gel; methylene chloride/methanol/concentrated ammonia=4:1:0.2)

(4) [4-[4-(4-Piperidinyl)-piperazin-1-yl]carbonylamino]-piperidinoacetic acid trihydrochloride Prepared from methyl [4-[4-(4-piperidinyl)-piperazin-1-yl]carbonylamino]piperidino acetate trihydrochloride. Mass spectrum: $M^+=353$; $R_f$ value: 0.10 (silica gel; methylene chloride/methanol/concentrated ammonia=4:1:0.25)

(5) N-[4-[[4-(4-Piperidinyl)-piperazin-1-yl]carbonyl]piperidinyl]-β-alanine trihydrochloride Prepared from N-[4-[[4-(4-piperidinyl)-piperazin-1-yl]-carbonyl]-piperidinyl]-β-alanine methyl ester trihydrochloride.

Melting point: 282–284° C. (decomposition); Mass spectrum: $M^+=367$; $R_f$ value: 0.60 (reversed phase plate RP18; methanol/5% strength sodium chloride solution=6:4)

(6) N-[[4-(4-Piperidinyl)-piperazin-1-yl]-carbonyl]-3-(4-piperidinyl)-propionic acid dihydrochloride Prepared from methyl N-[[4-(4-piperidinyl)-piperazin-1-yl]carbonyl]-3-(4-piperidinyl)-propionate dihydrochloride.

Melting point: 293–294° C. (decomposition); $R_f$ value: 0.57 (reversed phase plate RP18; methanol/50% strength sodium chloride solution=6:4)

(7) N-Acetyl-N-[4-[[4-(4-piperidinyl)-piperazin-1-yl] carbonyl]piperidinyl]-β-alanine dihydrochloride Prepared from N-acetyl-N-[4-[[4-(4-piperidinyl)-piperazin-1-yl]carbonyl]piperidinyl]-β-alanine methyl ester dihydrochloride. Oil, Mass spectrum: $M^+=409$; $R_f$ value: 0.70 (reversed phase plate RP18; methanol/5% strength sodium chloride solution=3:2)

(8) N-Methyl-N-[4-[[4-(4-piperidinyl)-piperazin-1-yl] carbonyl]piperidinyl]-β-alanine trihydrochloride Prepared from N-methyl-N-[4-[[4-(4-piperidinyl)-piperazin-1-yl]carbonyl]piperidinyl]-β-alanine methyl ester trihydrochloride.

(9) N-[[[4-(4-Piperidinyl)-piperazin-1-yl]carbonyl]-(piperidin-4-yl)-carbonyl]-β-alanine dihydrochloride Prepared from N-[[[4-(4-piperidinyl)-piperazin-1-yl]carbonyl]-(piperidin-4-yl)-carbonyl]-β-alanine methyl ester dihydrochloride.

Melting point: 272–274° C. (decomposition); Mass spectrum: $M^+=395$; $R_f$ value: 0.20 (silica gel; methylene chloride/methanol/concentrated ammonia=2:1:0.25

(10) N-[4-[[4-(4-Piperidinyl)-piperazin-1-yl]carbonyl]piperidinyl]glycine trihydrochloride Prepared from N-[4-[[4-(4-piperidinyl)-piperazin-1-yl]carbonyl]piperidinyl]glycine methyl ester trihydrochloride.

(11) N-Methyl-N-[4-[[4-(4-piperidinyl)-piperazin-1-yl] carbonyl]piperidinyl]glycine trihydrochloride Prepared from N-methyl-N-[4-[[4-(4-piperidinyl)-piperazin-1-yl]carbonyl]piperidinyl]glycine methyl ester trihydrochloride.

(12) N-Acetyl-N-[4-[[4-(4-piperidinyl)-piperazin-1-yl] carbonyl]piperidinyl]glycine dihydrochloride Prepared from N-acetyl-N-[4-[[4-(4-piperidinyl)-piperazin-1-yl]carbonyl]piperidinyl]glycine methyl ester dihydrochloride.

(13) N-[[4-(4-Piperidinyl)-piperazin-1-yl]-carbonyl]-4-(4-piperidinyl)-butyric acid dihydrochloride Prepared from methyl N-[[4-(4-piperidinyl)-piperazin-1-yl]-carbonyl]-4-(4-piperidinyl)-butyrate dihydrochloride.

Melting point: 296–298° C. (decomposition); $R_f$ value: 0.45 (reversed phase plate RP18; methanol/5% strength sodium chloride solution=6:4)

(14) N-[[4-(4-Piperidinyl)-piperazin-1-yl]acetyl]-4-piperidinyloxy-acetic acid trihydrochloride Prepared from methyl N-[[4-(4-piperidinyl)-piperazin-1-yl]acetyl]-4-piperidinyloxyacetate trihydrochloride. Amorphous solid.

Mass spectrum: $M^+=368$; $R_f$ value: 0.24 (silica gel; methylene chloride/methanol/concentrated ammonia=4:1:0.2)

(15) N-[[4-(4-Piperidinyl)-piperazin-1-yl]acetyl]-4-piperidinyl-acetic acid trihydrochloride Prepared from methyl N-[[4-(4-piperidinyl)-piperazin-1-yl]acetyl]-4-piperidinylacetate trihydrochloride. Amorphous solid.

Mass spectrum: $M^+=352$; $R_f$ value 0.15 (silica gel; methylene chloride/methanol/concentrated ammonia=2:1:0.25)

(16) N-[[4-(4-Piperidinyl)-piperazin-1-yl]acetyl] piperazinoacetic acid tetrahydrochloride Prepared from methyl N-[[4-(4-piperidinyl)-piperazin-1-yl]acetyl]-piperazinoacetate tetrahydrochloride. Amorphous solid.

Mass spectrum: $(M+H)^+=354$;

(17) [4-trans-[[4-(4-Piperidinyl)-piperazin-1-yl]acetyl] amino]-cyclohexane-carboxylic acid trihydrochloride Prepared from methyl [4-trans-[[4-(4-piperidinyl)-piperazin-1-yl]-acetyl]amino]cyclohexanecarboxylate trihydrochloride. Amorphous solid.

Mass spectrum: $M^+=352$; $R_f$ value: 0.85 (reversed phase plate RP18; methanol/5% strength sodium chloride solution=3:2)

(18) N-[[4-(4-Piperidinyl)-piperazin-1-yl]acetyl]-3-(4-piperidinyl)-propionic acid trihydrochloride Prepared from methyl N-[[4-(4-piperidinyl)-piperazin-1-yl]acetyl]-3-(4-piperidinyl)-propionate trihydrochloride. Amorphous solid.

Mass spectrum: $(M+H)^+=367$; $R_f$ value: 0.63 (reversed phase plate RP18; methanol/5% strength sodium chloride solution=3:2)

(19) 4-[[4-(4-Piperidinyl)-piperazin-1-yl]acetyl]phenoxyl-acetic acid trihydrochloride Prepared from methyl [4-[[4-(4-piperidinyl)-piperazin-1-yl]acetyl]-phenoxy]acetate trihydrochloride.

Melting point: 265–270° C. (decomposition); Mass spectrum: $(M+H)^+=362$; $R_f$ value: 0.075 (silica gel; methylene chloride/methanol/concentrated ammonia=4:1:0.2)

(20) [3-[[4-(4-Piperidinyl)-piperazin-1-yl]carbonylaminolphenoxyl-acetic acid dihydrochloride Prepared from methyl [3-[[4-(4-piperidinyl)-piperazin-1-yl]carbonylamino]phenoxy]acetate dihydrochloride.

Melting point: 240–242° C. (decomposition); Mass spectrum: $(M+H)^+=363$; $R_f$ value: 0.07 (silica gel; methylene chloride/methanol/concentrated ammonia=4:1:0.2)

(21) 4-[[4-(4-Piperidinyl)-piperazin-1-yl]acetyl]phenyl-acetic acid trihydrochloride Prepared from methyl 4-[[4-(4-piperidinyl)-piperazin-1-yl]acetyl]-phenyl acetate trihydrochloride.

(22) [3-[[4-(4-Piperidinyl)-piperazin-1-yl]carbonylaminolphenyl]propionic acid dihydrochloride Prepared from methyl 3-[4-(4-piperidinyl)-piperazin-1-yl]carbonylamino]phenyl]propionate dihydrochloride.

Melting point: 289–292° C. (decomposition); Mass spectrum: $M^+=360$; $R_f$ value: 0.80 (reversed phase plate RP18; methanol/5% strength sodium chloride solution=6:4)

(23) [4-[[4-(4-Piperidinyl)-piperazin-1-yl]carbonylaminolphenoxyl-acetic acid dihydrochloride Prepared from methyl [4-[[4-(4-piperidinyl)-piperazin-1-yl]carbonylamino]phenoxy]acetate dihydrochloride.

Melting point: 263–2650C. (decomposition); Mass spectrum: $M^+=362$; $R_f$ value: 0.75 (reversed phase plate RP18; methanol/5% strength sodium chloride solution=6:4)

(24) N-[4-trans-[4-(4-Piperidinyl)-piperazin-1-yl]carbonylaminocyclohexyl]glycine trihydrochloride Prepared from N-[4-trans-[4-(4-piperidinyl)-piperazin-1-yl]-carbonylaminocyclohexyl]glycine methyl ester trihydrochloride. Amorphous solid.

Mass spectrum: $(M+H)^+=368$; $R_f$ value: 0.095 (silica gel; methylene; chloride/methanol/concentrated ammonia= 2:1:0.25)

(25) N-[4-trans-[4-(4-Piperidinyl)-piperazin-1-yl]carbonylaminocyclohexyl]sarcosine trihydrochloride Prepared from N-[4-trans-[4-(4-piperidinyl)-piperazin-1-yl]-carbonylaminocyclohexyl]sarcosine methyl ester trihydrochloride.

(26) N-Acetyl-N-[4-trans-[4-(4-piperidinyl)-piperazin-1-yl]-carbonylaminocyclohexyl]glycine dihydrochloride Prepared from N-acetyl-N-[4-trans-[4-(4-piperidinyl)-piperazin-1-yl]carbonylaminocyclohexyl]glycine methyl ester dihydrochloride.

(27) N-[4-[4-(4-Piperidinyl)-piperazin-1-yl]carbonylaminophenyl]glycine dihydrochloride Prepared from N-[4-[4-(4-piperidinyl)-piperazin-1-yl]carbonylaminophenyl]glycine methyl ester dihydrochloride. Amorphous solid.

Mass spectrum: $(M+H)^+=362$;

(28) N-[4-[4-(4-Piperidinyl)-piperazin-1-yl]carbonylaminophenyl]sarcosine dihydrochloride Prepared from N-[4-[4-(4-piperidinyl)-piperazin-1-yl]carbonylaminophenyl]sarcosine methyl ester dihydrochloride.

(29) N-Acetyl-N-[4-[4-(4-piperidinyl)-piperazin-1-yl]carbonylaminophenyl]glycine dihydrochloride Prepared from N-acetyl-N-[4-[4-(4-piperidinyl)-piperazin-1-yl]carbonylaminophenyl]glycine methyl ester dihydrochloride.

(30) N-[[4-(4-Piperidinyl)-piperazin-1-yl]carbonyl]-3-(piperidin-4-yloxy)-propionic acid dihydrochloride Prepared from ethyl N-[[4-(4-piperidinyl)-piperazin-1-yl]carbonyl]-3-(piperidin-4-yloxy)propionate dihydrochloride.

Melting point: 288–290° C. (decomposition); Mass spectrum: $M^+=368$; $R_f$ value: 0.65 (reversed phase plate RP 18; methanol/5 strength sodium chloride solution=3:2)

(31) [4-trans-[4-(4-Piperidinyl)-piperazin-1-yl]carbonylamino-cyclohexyloxy]-acetic acid dihydrochloride Prepared from methyl [4-trans-[4-(4-piperidinyl)-piperazin-1-yl]carbonylaminocyclohexyloxy]acetate dihydrochloride.

Melting point: 290–296° C. (decomposition); Mass spectrum: $(M+H)^+=369$; $R_f$ value: 0.75 (reversed phase plate RP 18; methanol/50 strength sodium chloride solution=3:2)

(32) N-[[4-(4-Piperidinyl)-piperazin-1-yl]carbonyl]-(piperidin-4-yloxy)-acetic acid dihydrochloride Prepared from methyl N-[[4-(4-piperidinyl)-piperazin-1-yl]carbonyl]-(piperidin-4-yloxy)acetate dihydrochloride.

(33) N-[[4-(4-Piperidinyl)-piperazin-1-yl]carbonyl]-(piperidin-4-yl)-carbonyl]glycine dihydrochloride Prepared from N-[[4-(4-piperidinyl)-piperazin-1-yl]carbonyl]-(piperidin-4-yl)-carbonyl]glycine ethyl ester dihydrochloride.

Melting point: 276–278° C. (decomposition); Mass spectrum: $(M+H)^+=382$; $R_f$ value: 0.21 (silica gel; methylene chloride/methanol/concentrated ammonia=2:1:0.25)

(34) N-Benzyl-N-[4-[4-(4-piperidinyl)-piperazin-1-yl]carbonylaminophenyl]glycine dihydrochloride Prepared from N-benzyl-N-[4-[4-(4-piperidinyl)-piperazin-1-yl]carbonylaminophenyl]glycine methyl ester dihydrochloride.

(35) [4-trans-[4-(4-Piperidinyl)-piperazin-1-yl]carbonylamino-cyclohexyloxyacetic acid dihydrochloride Prepared from tert-butyl [4-trans-[4-(4-piperidinyl)-piperazin-1-yl]carbonylamino-cyclohexyloxy]acetate.

Melting point: 290–2960C. (decomposition); Mass spectrum: $(M+H)^+=369$; $R_f$ value: 0.75 (reversed phase plate RP18; methanol/5% strength sodium chloride solution=3:2)

(36) [3,4-[[4-Piperidinyl)-piperazin-1-yl]carbonylamino]-phenylenedioxyldiacetic acid dihydrochloride Prepared from dimethyl [3,4-[[4-(4-piperidinyl)-piperazin-1-yl]carbonylamino]phenylenedioxy]diacetate dihydrochloride.

Melting point: 70–80° C. (decomposition); Mass spectrum: $(M-H)^-=435$

(37) 3-[4-[[4-(4-Piperidinyl)-piperazin-1-yl]carbonylamino]-phenoxylpropionic acid dihydrochloride Prepared from ethyl 3-[4-[[4-(4-piperidinyl)-piperazin-1-yl]carbonylamino]phenoxy]propionate dihydrochloride.

Melting point: 190–192° C. (decomposition); Mass spectrum: $(M+H)^+=377$; $R_f$ value: 0.55 (reversed phase plate RP18; methanol/5% strength sodium chloride solution=3:2)

(38) 3-[4-[[4-(4-Piperidinyl)-piperazin-1-yl]carbonyl]-phenoxylpropionic acid dihydrochloride Prepared from ethyl 3-[4-[[4-(4-piperidinyl)-piperazin-1-yl]carbonyl]phenoxy]propionate dihydrochloride.

Melting point: 277–280° C. (decomposition); Mass spectrum: $(M+H)^+=362$; $R_f$ value: 0.45 (reversed phase plate RP18; methanol/5% strength sodium chloride solution=3:2)

(39) 4-[[4-(4-Piperidinyl)-piperazin-1-yl]carbonylaminolphen-ylacetic acid dihydrochloride Prepared from ethyl 4-[[4-(4-piperidinyl)-piperazin-1-yl]carbonylamino]phenylacetate dihydrochloride.

(40) [4-trans-[[4-(4-Piperidinyl)-piperazin-1-yl]carbonylamino]cyclohexyl]acetic acid dihydrochloride Prepared from methyl [4-trans-[[4-(4-piperidinyl)-piperazin-1-yl]carbonylamino]cyclohexyl]acetate dihydrochloride.

(41) N-[4-[[4-(4-Piperidinyl)-piperazin-1-yl]carbonyl]phenyl]-β-alanine dihydrochloride Prepared from N-[4-[[4-(4-piperidinyl)-piperazin-1-yl]carbonyl]phenyl]-β-alanine ethyl ester dihydrochloride. Amorphous solid.

Mass spectrum: (M+H)$^+$=361; $R_f$ value: 0.52 (reversed phase plate RP18; methanol/5 % strength sodium chloride solution=3:2)

(42) N-[3-[[4-(4-Piperidinyl)-piperazin-1-yl]carbonyl]phenyl]-E-alanine dihydrochloride Prepared from N-[3-[[4-(4-piperidinyl)-piperazin-1-yl]carbonyl]phenyl]-β-alanine ethyl ester dihydrochloride. Amorphous solid.

Mass spectrum: M$^+$=360; $R_f$ value: 0.75 (reversed phase plate RP18; methanol/5% strength sodium chloride solution=3:2)

(43) 3-[3-[[4-(4-Piperidinyl)-piperazin-1-yl]carbonyl]phenyloxylpropionic acid dihydrochloride Prepared from ethyl 3-[3-[[4-(4-piperidinyl)-piperazin-1-yl]carbonyl]phenyloxy]propionate dihydrochloride.

Melting point: 262–264° C. (decomposition); Mass spectrum: (M+H)$^+$=362; $R_f$ value: 0.10 (silica gel; methylene chloride/methanol/concentrated ammonia=4:1:0.2)

(44) N-4-[[4-(4-Piperidinyl)-piperazin-1-yl]carbonylethyl]-piperidinyl-acetic acid trihydrochloride Prepared from ethyl N-4-[[4-(4-piperidinyl)-piperazin-1-yl]carbonylethyl]piperidinylacetate trihydrochloride.

Mass spectrum: M$^+$=366; $R_f$ value: 0.19 (silica gel; methylene chloride/methanol/concentrated ammonia=2:1:0.25)

(45) N-4-[[4-(4-Piperidinyl)-piperazin-1-yl]-malonyl]piperidinyl-acetic acid dihydrochloride Prepared from methyl N-4-[[4-(4-piperidinyl)-piperazin-1-yl]malonyl]piperidinylacetate dihydrochloride. Amorphous solid.

Mass spectrum: M$^+$=380; $R_f$ value: 0.13 (silica gel; methylene chloride/methanol/concentrated ammonia=2:1:0.25)

(46) N-4-[[4-(4-Piperidinyl)-piperazin-1-yl]-ethylcarbonyl]-piperidinyl-acetic acid trihydrochloride Prepared from methyl N-4-[[4-(4-piperidinyl)-piperazin-1-yl]ethylcarbonyl]piperidinylacetate trihydrochloride. Melting point: 229–233° C. (decomposition);

Mass spectrum: (M+H)$^+$=367; $R_f$ value: 0.55 (reversed phase plate RP18; methanol/5% strength sodium chloride solution=3:2)

(47) [4-trans-[2S-(4-(4-Piperidinyl)-piperazin-1-yl]propionylamino]cyclohexanecarboxylic acid trihydrochloride Prepared from methyl [4-trans-[2S-(4-(4-piperidinyl)-piperazin-1-yl]propionylamino]cyclohexanecarboxylate trihydrochloride. Amorphous substance.

Mass spectrum: M$^+$=366; $R_f$ value: 0.70 (reversed phase plate RP18; methanol/5% strength sodium chloride solution=3:2)

(48) [4-trans-[2S-(4-(4-Piperidinyl)-piperazin-1-yl)]-(3-(4-methoxyphenyl))propionylamino]cyclohexane-carboxylic acid trihydrochloride Prepared from methyl [4-trans-[2S-(4-(4-piperidinyl)-piperazin-1-yl)]-(3-(4-methoxyphenyl))propionylamino]-cyclohexanecarboxylate trihydrochloride. Amorphous substance.

Mass spectrum: M$^+$=472; $R_f$ value: 0.55 (reversed phase plate RP18; methanol/5% strength sodium chloride solution=3:2)

(49) N-[[2S-(4-(4-Piperidinyl)-piperazin-1-yl]propionyl]-4-piperidinyloxyacetic acid trihydrochloride Prepared from methyl N-[[2S-(4-(4-piperidinyl)-piperazin-1-yl]-propionyl]-4-piperidinyloxyacetate trihydrochloride.

(50) N-[[2S-(4-(4-Piperidinyl)-piperazin-1-yl)]-(3-(4-methoxyphenyl))propionyl]-4-piperidinyloxy-acetic acid trihydrochloride Prepared from ethyl N-[[2S-(4-(4-piperidinyl)-piperazin-1-yl)]-(3-(4-methoxyphenyl))propionyl]-4-piperidinyloxyacetate.

Mass spectrum: (M+H)$^+$=489; $R_f$ value: 0.68 (reversed phase plate RP18; methanol/5% strength sodium chloride solution=3:2)

(51) [N-trans-[4-(4-Piperidinyl)-piperazin-1-yl] oxalylamino]-cyclohexanecarboxylic acid dihydrochloride Prepared from methyl [4-trans-[4-(4-piperidinyl)-piperazin-1-yl]oxalylamino]-cyclohexanecarboxylate dihydrochloride.

(52) N-[[4-(4-Piperidinyl)-piperazin-1-yl]oxalyl]-4-piperidinyloxy-acetic acid dihydrochloride Prepared from methyl N-[[4-(4-piperidinyl)-piperazin-1-yl]oxalyl]-4-piperidinyloxyacetate dihydrochloride.

(53) 4-[[4-(4-Piperidinyl)-piperazin-1-yl]carbonylmethyl]-phenoxyl-acetic acid dihydrochloride Prepared from methyl 4-[[4-(4-piperidinyl)-piperazin-1-yl]carbonylmethyl]-phenoxy]acetate dihydrochloride.

Melting point: from 148° C. (decomposition);

Mass spectrum: M$^+$=361; $R_f$ value: 0.25 (silica gel; methylene chloride/methanol/concentrated ammonia=2:1:0.25)

(54) [4-[[4-(4-Piperidinyl)-piperazin-1-yl]-2-ethyl] phenoxyl-acetic acid trihydrochloride Prepared from methyl [4-[[4-(4-piperidinyl)-piperazin-1-yl]-2-ethyl]phenoxy]acetate trihydrochloride. Melting point: 312–315° C. (decomp.);

Mass spectrum: (M+H)$^+$=348; $R_f$ value: 0.25 (silica gel; methylene chloride/methanol/concentrated ammonia= 2:1:0.25)

(55) N-[4-(4-(1-Benzyl)-piperidinyl)-piperazin-1-yl]carbonyl]-piperidine-4-carboxylic acid Prepared by reaction of methyl [N-[4-(4-(1-benzyl)-piperidinyl)-piperazin-1-yl]carbonyl]piperidine-4-carboxylate with half-concentrated hydrochloric acid.

(56) [4-[[[-4-(Piperidin-4-yl)-piperazin-1-yl]-carbonyl]-amino-methyl]-piperidin-1-yl]-acetic acid trihydrochloride tert-Butyl [4-[[[-4-[1-(tert-butyloxycarbonyl)-piperidin-4-yl]-piperazin-1-yl]-carbonyl]-aminomethyl]-piperidin-1-yl]-acetate is employed and the mixture is stirred at room temperature for 2 hours. The residue is triturated with methanol and filtered off with suction. Melting point: Sintering from 270° C.;

Mass spectrum: (M+H)$^+$=368; $R_f$ value: 0.40 (silica gel; methylene chloride/methanol/concentrated ammonia= 3:1:0.2)

(57) [4-[[4-(Piperidin-4-yl)-piperazin-3-on-1-yl]-carbonylaminol-phenoxyl-acetic acid hydrochloride

(58) [4-[[2-Methyl-4-(piperidin-4-yl)-piperazin-3-on-1-yl]-carbonylamino]-phenoxy]-acetic acid hydrochloride

(59) [4-[[2-Methyl-4-(piperidin-4-yl)-piperazin-1-yl]-carbonylamino]-phenoxy]-acetic acid dihydrochloride

(60) [4-[[2-[[4-Methoxy-phenyl]-methyl]-4-(piperidin-4-yl)-piperazin-3-on-1-yl]-carbonylamino]-phenoxy]-acetic acid hydrochloride

(61) [4-[[4-(Piperidin-4-yl)-tetrahydroquinoxalin-1-yl]-carbonylamino]-phenoxy]-acetic acid dihydrochloride

(62) 4-[[4-(Piperidin-4-yl)-piperazine-2,5-dion-1-yl]-methylcarbonyl]-phenoxy]-acetic acid hydrochloride

(63) α-[trans-4-[[4-(piperidin-4-yl)-piperazin-1-yl]-carbonyl]-cyclohexylcarbonylamino]-α-(phenylmethyl)-acetic acid The residue is chromatographed over silica gel with methanol/dioxane/concentrated ammonia (2:1:0.2). Melting point: Sintering from 210–2200C.;

Mass spectrum: (M+H)⁺=471; $R_f$ value: 0.32 (silica gel; methylene chloride/methanol/concentrated ammonia=2:1:0.2)

(64) α-(Aminocarbonylmethyl)-α-[trans-4-[[4-(piperidin-4-yl)-piperazin-1-yl]-carbonyl]-cyclohexylcarbonylaminol-acetic acid di-trifluoroacetate Prepared from α-(aminocarbonylmethyl)-α-[trans-4-[[4-(piperidin-4-yl)-piperazin-1-yl]-carbonyl]-cyclohexylcarbonylamino]-acetic acid and 50% strength trifluoroacetic acid in methylene chloride.

Mass spectrum: (M+H)=438; $R_f$ value: 0.08 (silica gel, methylene chloride/methanol/concentrated ammonia=2:1:0.2)

EXAMPLE 2

Methyl 3-[4-trans-[[4-(4-piperidinyl)-piperazin-1-yl] carbonylamino]cyclohexyl]propionate dihydrochloride 20 ml of ethereal hydrochloric acid are added to a solution of 1.6 g (0.0033 mol) of methyl 3-[4-trans-[4-[4-(1-tert-butyloxycarbonyl)-piperidinyl)-piperazin-1-yl] carbonylamino]cyclohexyl]propionate in 10 ml of methanol and the mixture is left to stand overnight at room temperature. It is then concentrated to dryness in vacuo, acetone is added to the residue and the mixture is concentrated to dryness again. The solid residue is triturated with acetone, filtered off with suction and dried. Melting point: 311–313° C.;

Mass spectrum: M⁺=380; $R_f$ value: 0.09 (silica gel; methylene chloride/methanol =9:1)

The following compounds can be prepared analogously to EXAMPLE 2:

(1) Methyl [4-trans-[4-(4-piperidinyl)-piperazin-1-yl] malonylaminol-cyclohexylcarboxylate dihydrochloride Prepared from methyl [4-trans-[4-(4-(1-tert-butyloxycarbonyl)-piperidinyl)-piperazin-1-yl] malonylamino]cyclohexylcarboxylate and ethereal hydrochloric acid in methanol. Melting point: 254–2560C.;

Mass spectrum: M⁺=394; $R_f$ value: 0.08 (silica gel; methylene chloride/methanol/concentrated ammonia=9:1:0.1)

(2) Methyl 3-[4-[4-(4-piperidinyl)-piperazin-1-yl] carbonylaminolpiperidino propionate trihydrochloride Prepared from methyl 3-[4-[4-(4-(1-tert-butyloxycarbonyl)-piperidinyl)-piperazin-1-yl] carbonylamino]piperidino propionate and ethereal hydrochloric acid in methanol. Melting point: 275–277° C.;

Mass spectrum: M⁺=381; $R_f$ value: 0.08 (silica gel; methylene chloride/methanol/concentrated ammonia=9:1:0.1)

(3) Methyl [4-[4-(4-piperidinyl)-piperazin-1-yl] carbonylaminolpiperidino acetate trihydrochloride Prepared from methyl [4-[4-(4-(1-tert-butyloxycarbonyl)-piperidinyl]piperazin-1-yl]carbonylamino]piperidino acetate and ethereal hydrochloric acid in methanol. Melting point: 260–265° C. (decomposition);

Mass spectrum: M⁺=367; $R_f$ value: 0.10 (silica gel; methylene chloride/methanol =9:1)

(4) N-[4-[[4-(4-Piperidinyl)-piperazin-1-yl]-carbonyl] piperidinyl]-β-alanine methyl ester trihydrochloride Prepared from N-tert-butyloxycarbonyl-N-[4-[4-[4-(1-tertbutyloxycarbonyl-piperidinyl)-piperazin-1-yl]carbonyl] piperidinyl]-β-alanine methyl ester and 50% strength trifluoroacetic acid in methylene chloride. The trihydrochloride is prepared with hydrochloric acid. Melting point: 273–275° C. (decomposition);

Mass spectrum: M⁺=381;

(5) N-Acetyl-N-[4-[[4-(4-piperidinyl)-piperazin-1-yl] carbonyl]-piperidinyl]-β-alanine methyl ester dihydrochloride Prepared from N-acetyl-N-[4-[[4-(4-(1-tert-butyloxycarbonyl-piperidinyl)-piperazin-1-yl]carbonyl] piperidinyl]-β-alanine methyl ester and 50% strength trifluoroacetic acid in methylene chloride. Melting point: 260–2620° C. (decomposition);

(6) N-Methyl-N-[4-[[4-(4-piperidinyl)-piperazin-1-yl] carbonyl]piperidinyl]-β-alanine methyl ester trihydro chloride Prepared from N-[4-[[4-(4-(1-tert-butyloxycarbonyl)-piperidinyl)-piperazin-1-yl]carbonyl]piperidinyl]-N-methyl-β-alanine methyl ester and 50% strength trifluoroacetic acid in methylene chloride.

(7) N-[4-[[4-(4-Piperidinyl)-piperazin-1-yl]carbonyl] piperidinyl]glycine methyl ester trihydrochloride Prepared from N-tert-butyloxycarbonyl-N-[4-[[4-(4-(1-tert-butyloxycarbonyl)-piperidinyl)-piperazin-1-yl] carbonyl]piperidinyl]glycine methyl ester and 50% strength trifluoroacetic acid in methylene chloride (8) N-Methyl-N-[4-[[4-(4-piperidinyl)-piperazin-1-yl] carbonyl]piperidinyl]glycine methyl ester trihydrochloride Prepared from 4-[4-[[4-(4-(1-tert-butyloxycarbonyl)-piperidinyl)-piperazin-1-yl]carbonyl]piperidinyl]-N-methyl-glycine methyl ester and 50% strength trifluoroacetic acid in methylene chloride.

(9) N-Acetyl-N-[4-[[4-(4-piperidinyl)-piperazin-1-yl] carbonyl]piperidinyl]glycine methyl ester dihydrochloride Prepared from N-acetyl-N-[4-[[4-(4-(1-tert-butyloxycarbonyl)-piperidinyl)-piperazin-1-yl]carbonyl]-(piperidinyl]-glycine methyl ester and 50% strength trifluoroacetic acid in methylene chloride.

(10) Methyl N-[[4-(4-piperidinyl)-piperazin-1-yl]-carbonyl]-4-(4-piperidinyl)-butyrate dihydrochloride Prepared from methyl N-[[4-(4-(1-tert-butyloxycarbonyl)-piperidinyl]-piperazin-1-yl]carbonyl]-4-(4-piperidinyl)-butyrate and 50% strength trifluoroacetic acid in methylene chloride.

Melting point: 306–307° C. (decomposition); $R_f$ value: 0.15 (reversed phase plate RP18; methanol/5% strength sodium chloride solution=6:4)

(11) Methyl [4-[[4-(4-piperidinyl)-piperazin-1-yl]acetyl] phenoxyl-acetate trihydrochloride Prepared from methyl [4-[[4-(4-(1-tert-butyloxycarbonyl)-piperidinyl)-piperazin-1-yl]acetyl] phenoxy]acetate and ethereal hydrochloric acid. Melting point: 245–247° C.;

Mass spectrum: M⁺=375; $R_f$ value: 0.095 (silica gel; methylene chloride/methanol=9:1)

(12) Methyl [3-[[4-(4-piperidinyl)-piperazin-1-yl] carbonylaminolphenoxylacetate dihydrochloride Prepared from methyl [3-[[4-(4-(1-tert-butyloxycarbonyl)-piperidinyl)-piperazin-1-yl]acetyl] phenoxy]acetate and ethereal hydrochloric acid- Melting point: 250–252° C.;

Mass spectrum: M⁺=376; $R_f$ value: 0.095 (silica gel; methylene chloride/methanol=9:1)

(13) Methyl 4-[[4-(4-piperidinyl)-piperazin-1-yl]-acetyl] phenylacetate trihydrochloride Prepared from methyl 4-[[4-(4-(1-tert-butyloxycarbonyl)-piperidinyl)-piperazin-1-yl]acetyl]phenylacetate and ethereal hydrochloric acid.

(14) Methyl (4-trans-[4-(4-piperidinyl)-piperazin-1-yl] carbonylaminolphenyl]propionate dihydrochloride Prepared from methyl [3-[[4-(4-(1-tert-butyloxycarbonyl)-piperidinyl)-piperazin-1-yl]

carbonylamino]phenyl]propionate and ethereal hydrochloric acid. Melting point: 292–2950° C. (decomposition);

Mass spectrum: M$^+$=374; R$_f$ value: 0.80 (reversed phase plate RP 18; methanol/5% strength sodium chloride solution=3:2)

(15) Ethyl N-[[4-(4-piperidinyl)-piperazin-1-yl]-carbonyl]-3-(piperidin-4-yloxy)-propionate dihydrochloride Prepared from ethyl N-[[4-(4-(1-tert-butyloxycarbonyl)-piperidinyl)-piperazin-1-yl]carbonyl]-3-(piperidin-4-yloxy)-propionate and 50% strength trifluoroacetic acid in methylene chloride. Amorphous solid Mass spectrum: M$^+$=390; Rf-Wert: 0.12 (silica gel; methylene chloride/methanol=9:1)

(16) N-[[4-(4-Piperidinyl)-piperazin-1-yl]carbonyl]-piperidin-4-yl)-carbonyl]-β-alanine methyl ester dihydrochloride Prepared from N-[[4-(4-(1-tert-butyloxycarbonyl)-piperidinyl)-piperazin-1-yl]carbonyl]-piperidin-4-yl)-carbonyl]-β-alanine ethyl ester and ethereal hydrochloric acid in methanol. Melting point: 288–290° C.;

Mass spectrum: M$^+$=409; R$_f$ value: 0.50 (silica gel; methylene chloride/methanol/concentrated ammonia=2:1:0.25)

(17) Dimethyl [3,4-[[4-(4-piperidinyl)-piperazin-1-yl]carbonylamino]phenylenedioxy]diacetate dihydrochloride Prepared from dimethyl [3,4-[[4-(4-(1-tert-butyloxycarbonyl)-piperidinyl)-piperazin-1-yl]carbonylamino]-phenylenedioxy]diacetate and 50% strength trifluoroacetic acid in methylene chloride. Melting point: 240–2420° C.;

Mass spectrum: (M+H)$^+$=465;

(18) Ethyl 3-[4-[[4-(4-piperidinyl)-piperazin-1-yl]carbonylaminolphenoxylpropionate dihydrochloride Prepared from ethyl 3-[4-[[4-(4-(1-tert-butyloxycarbonyl)-piperidinyl)-piperazin-1-yl]carbonylamino]phenoxy]propionate and 50% strength trifluoroacetic acid in methylene chloride. Melting point: 245–250° C. (decomposition);

Mass spectrum: M$^+$=404; R$_f$ value: 0.85 (silica gel; methylene chloride/methanol=9:1)

(19) Ethyl 3-[4-[[4-(4-piperidinyl)-piperazin-1-yl]carbonyl] phenoxylpropionate hydrochloride Prepared from ethyl 3-[4-[[4-(4-(1-tert-butyloxycarbonyl)-piperidinyl)-piperazin-1-yl]carbonyl] phenoxy]propionate and 50% strength trifluoroacetic acid in methylene chloride. Melting point: 304–3060° C. (decomposition);

Mass spectrum: M$^+$=389; R$_f$ value: 0.09 (silica gel; methylene chloride/methanol=9:1)

(20) Ethyl 4-[[4-(4-piperidinyl)-piperazin-1-yl] carbonylaminolphenylacetate dihydrochloride Prepared from ethyl 4-[[4-(4-(1-tert-butyloxycarbonyl)-piperidinyl)-piperazin-1-yl]carbonylamino]phenylacetate and 50% strength trifluoroacetic acid in methylene chloride.

(21) Methyl [4-trans-[[4-(4-piperidinyl)-piperazin-1-yl]carbonylaminolcyclohexyl]acetate dihydrochloride Prepared from methyl [4-trans-[[4-(4-(1-tert-butyloxycarbonyl)piperidinyl)-piperazin-1-yl] carbonylamino]cyclohexyl]acetate and 50% strength trifluoroacetic acid in methylene chloride.

(22) N-[3-[[4-(4-Piperidinyl)-piperazin-1-yl]carbonyl] phenyl]-β-alanine ethyl ester dihydrochloride Prepared from N-[3-[[4-(4-(1-tert-butyloxycarbonyl)-piperidinyl)-piperazin-1-yl]carbonyl]-phenyl]-β-alanine ethyl ester and 50% strength trifluoroacetic acid in methylene chloride. Amorphous solid.

Mass spectrum: M$^+$=388;

(23) Ethyl 3-[3-[[4-(4-piperidinyl)-piperazin-1-yl]carbonyl] phenyloxylpropionate dihydrochloride Prepared from ethyl 3-[3-[[4-(4-(1-tert-butyloxycarbonyl)-piperidinyl)-piperazin-1-yl]carbonyl] phenyloxy]propionate and 50% strength trifluoroacetic acid in methylene chloride. Melting point: 290–2960° C. (decomposition);

Mass spectrum: M$^+$=389; R$_f$ value: 0.1 (silica gel; methylene chloride/methanol=9:1)

(24) Methyl N-4-[[4-(4-piperidinyl)-piperazin-1-yl] carbonylethyl]piperidinylacetate trihydrochloride Prepared from methyl N-4-[[4-(4-(1-tert-butyloxycarbonyl)-piperidinyl)-piperazin-1-yl] carbonylethyl]piperidinylacetate and 50% strength trifluoroacetic acid in methylene chloride. Amorphous solid.

Mass spectrum: M$^+$=380; R$_f$ value: 0.13 (silica gel; methylene chloride/methanol/concentrated ammonia=9:1:0.1)

(25) Methyl N-4-[[4-(4-piperidinyl)-piperazin-1-yl] malonyl]piperidinylacetate dihydrochloride Prepared from methyl N-4-[[4-(4-(1-tert-butyloxycarbonyl)-piperidinyl)-piperazin-1-yl]malonyl] piperidinylacetate and 50% strength trifluoroacetic acid in methylene chloride.

Foam, mass spectrum: M$^+$=394; R$_f$ value: 0.13 (silica gel; methylene chloride/methanol/concentrated ammonia= 9:1:0.1)

(26) Methyl N-4-[[4-(4-piperidinyl)-piperazin-1-yl] ethylcarbonyl]piperidinylacetate trihydrochloride Prepared from methyl N-4-[[4-(4-(1-tert-butyloxycarbonyl)-piperidinyl)-piperazin-1-yl] ethylcarbonyl]piperidinylacetate and 50 % strength trifluoroacetic acid in methylene chloride.

Foam, mass spectrum: M$^+$=394; R$_f$ value: 0.095 (silica gel; methylene chloride/methanol/concentrated ammonia= 9:1:0.1)

(27) Methyl [4-trans-[2S-(4-(4-piperidinyl)-piperazin-1-yl)] propionylamino]cyclohexanecarboxylate trihydrochloride Prepared from methyl [4-trans-[2S-(4-(4-(1-tert-butyloxycarbonyl)-piperidinyl)-piperazin-1-yl]propionyl-amino]cyclohexanecarboxylate and 50% strength trifluoroacetic acid in methylene chloride. Melting point: 262–2G6° C. (decomposition);

Mass spectrum: M$^+$=380; R$_f$ value: 0.06 (silica gel; methylene chloride/methanol=9:1)

(28) Methyl [4-trans-[2S-(4-(4-piperidinyl)-piperazin-1-yl)-(3-(4-methoxyphenyl))]propionylamino]cyclohexane-carboxylate trihydrochloride Prepared from methyl 4-trans-[2S-(4-(4-(1-tert-butyloxycarbonyl)-piperidinyl)-piperazin-1-yl]-(3-(4-methoxyphenyl))-propionylamino]-cyclohexanecarboxylate and 50% strength trifluoroacetic acid in methylene chloride. Amorphous solid.

Mass spectrum: M$^+$=486; R$_f$ value: 0.21 (silica gel; methylene chloride/methanol/concentrated ammonia=9:1:0.1)

(29) Methyl N-[2S-(4-(4-piperidinyl)-piperazin-1-yl)]-propionyl]-4-piperidinyloxyacetate trihydrochloride Prepared from methyl N-[2S-(4-(4-(1-tert-butyloxycarbonyl)-piperidinyl)-piperazin-1-yl]propionyl]-4-piperidinyloxy-acetate and 50% strength trifluoroacetic acid in methylene chloride.

(30) Methyl N-[[2S-(4-(4-piperidinyl)-piperazin-1-yl)]-(3-(4-methoxyphenyl))propionyl]-4-piperidinyloxyacetate trihydrochloride Prepared from methyl N-[2S-(4-(4-(1-tert-butyloxycarbonyl)-piperidinyl)-piperazin-1-yl]-(3-(4-methoxyphenyl))propionyl]-4-piperidinyloxyacetate and 50% strength trifluoroacetic acid in methylene chloride.

(31) Methyl [4-trans-[4-(4-piperidinyl)-piperazin-1-yl)] oxalylamino]cyclohexanecarboxylate dihydrochloride Prepared from methyl [4-trans-[4-(4-(1-tert-butyloxycarbonyl)-piperidinyl)-piperazin-1-yl)]oxalylamino]cyclohexane-carboxylate and ethereal hydrochloric acid. Melting point: 325° C. (decomposition);

Mass spectrum: M$^+$=380; R$_f$ value: 0.10 (silica gel; methylene chloride/methanol/concentrated ammonia=9:1:0.1)

(32) Methyl N-[[4-(4-piperidinyl)-piperazin-1-yl]oxalyl]-4-piperidinyloxyacetate dihydrochloride Prepared from methyl N-[[4-(4-(1-tert-butyloxycarbonyl)-piperidinyl)-piperazin-1-yl)]oxalyl]-4-piperidinyloxyacetate and ethereal hydrochloric acid. Melting point: 280–282° C.

Mass spectrum: M$^+$=396;

(33) Methyl N-[[4-(4-piperidinyl)-piperazin-1-yl]carbonyl]-4-piperidinyloxyacetate dihydrochloride Prepared from methyl N-[[4-(4-(1-tert-butyloxycarbonyl)-piperidinyl)-piperazin-1-yl)]carbonyl]-4-piperidinyloxy-acetate and ethereal hydrochloric acid.

(34) Methyl [4-[[4-(4-piperidinyl)-piperazin-1-yl]carbonylmethyl]phenoxylacetate dihydrochloride Prepared from methyl 4-[[4-(4-(1-tert-butyloxycarbonyl)-piperidinyl)-piperazin-1-yl)]carbonylmethyl]phenoxy]-acetate and ethereal hydrochloric acid.

Melting point: 265–267° C. (decomposition); Mass spectrum: M$^+$=375; R$_f$ value: 0.55 (silica gel; methylene chloride/methanol/concentrated ammonia=2:1:0.25)

(35) Methyl [4-[[4-(4-piperidinyl)-piperazin-1-yl]-2-ethyl]phenoxy]acetate trihydrochloride Prepared from methyl [4-[[4-(4-(1-tert-butyloxycarbonyl)-piperidinyl)-piperazin-1-yl)]-2-ethyl]phenoxy]acetate and ethereal hydrochloric acid.

Melting point: 182–188° C. (decomposition); Mass spectrum: (M+H)$^+$=362; Rfvalue: 0.25 (silica gel; methylene chloride/methanol/concentrated ammonia=4:1:0.1)

(36) N-Benzyl-N-[4-trans-[4-(4-piperidinyl)-piperazin-1-yl]-carbonylaminocyclohexyl]glycine trihydrochloride Prepared from N-benzyl-N-[4-trans-[4-(4-(1-tert-butyloxycarbonyl)-piperidinyl)-piperazin-1-yl)]carbonylaminocyclohexyl]glycine and 50% strength trifluoroacetic acid in methylene chloride. Oil.

R$_f$ value: 0.19 (silica gel; methylene chloride/methanol/concentrated ammonia=4:1:0.2)

(37) N-[4-[4-(4-Piperidinyl)-piperazin-1-yl]-carbonylamino-phenyl]glycine methyl ester dihydrochloride Prepared from N-[4-[4-(4-(1-tert-butyloxycarbonyl)-piperidinyl)-piperazin-1-yl)]carbonylaminophenyl]glycine methyl ester and ethereal hydrochloric acid.

Mass spectrum: M$^+$=375;

(38) N-[4-[4-(4-Piperidinyl)-piperazin-1-yl]-carbonylamino-phenyl]sarcosine methyl ester dihydrochloride Prepared from N-[4-[4-(4-(1-tert-butyloxycarbonyl)-piperidinyl)-piperazin-1-yl)]carbonylaminophenyl]-sarcosine methyl ester and ethereal hydrochloric acid.

(39) N-Benzyl-N-[4-[4-(4-piperidinyl)-piperazin-1-yl]carbonylaminophenyl]glycine methyl ester dihydrochloride Prepared from N-benzyl-N-[4-[4-(1-tert-butyloxycarbonyl)-piperidinyl)-piperazin- 1-yl)]carbonylaminophenyl]glycine methyl ester and ethereal hydrochloric acid.

(40) Cyclohexyl [4-[2-[[4-(piperidin-4-yl)-piperazin-1-yl]-carbonyl]ethyl]-piperidin-1-yl]acetate trihydrochloride The reaction is carried out in dioxane/ethereal hydrochloric acid (3:1). The precipitate is filtered off with suction and dried.

Mass spectrum: M$^+$=448; R$_f$ value: 0.36 (silica gel; methylene chloride/methanol/concentrated ammonia=4:1:0.2)

(41) Methyl [trans-4-[[4-(piperidin-4-yl)-piperazin-1-yl]-carbonyl]cyclohexylcarbonylamino]acetate dihydrochloride The reaction is carried out in a mixture of anhydrous methanol/dioxane/ethereal hydrochloric acid (1:1:1). After 1.5 hours, the precipitate is filtered off with suction and dried. Melting point: 303–306° C.;

Mass spectrum: M$^+$=394; R$_f$ value: 0.23 (silica gel; methylene chloride/methanol/concentrated ammonia=4:1:0.2)

(42) Methyl [4-[[[4-(piperidin-4-yl)-piperazin-1-yl]-carbonyl]-methyloxy]-piperidin-1-yl]acetate The crude product was chromatographed over silica gel with methylene chloride/methanol/concentrated ammonia (4:1:0.25).

Mass spectrum: M$^+$=382; R$_f$ value: 0.36 (silica gel; methylene chloride/methanol/concentrated ammonia=4:1:0.25)

(43) Ethyl 1-[2-[[4-(piperidin-4-yl)-piperazin-1-yl]-carbonylamino]ethyl]-piperidine-4-carboxylate trihydrochloride The reaction is carried out in a mixture of absolute dioxane/absolute ethanol/ethereal hydrochloric acid (1:1:2). The precipitate is filtered off with suction and dried.

Melting point: Sintering from 288° C.; Mass spectrum: M$^+$=395 R$_f$ value: 0.23 (silica gel; methylene chloride/methanol/concentrated ammonia=4:1:0.2)

(44) N-[[trans-4-[[4-(Piperidin-4-yl)-piperazin-1-yl]-carbonyl]-cyclohexyl]-methyl]-N-(phenylsulphonyl)-aminoacetic acid Prepared from tert-butyl N-[[trans-4-[[4-[1-(tert-butyloxycarbonyl)-piperidin-4-yl]-piperazin-1-yl]-carbonyl]-cyclohexyl]-methyl]-N-(phenylsulphonyl)-aminoacetate acid with 50% strength trifluoroacetic acid in methylene chloride. The crude product is chromatographed over silica gel with methylene chloride/methanol/concentrated ammonia (2:1:0.2).

Melting point: from 298° C. (decomposition); Mass spectrum: (M+H)$^+$=507 ; R$_f$ value: 0.22 (silica gel; methylene chloride/methanol/concentrated ammonia=2:1:0.2)

(45) Methyl 1-[trans-4-[[4-(piperidin-4-yl)-piperazin-1-yl]-carbonyl]-cyclohexylcarbonylamino]-1-(phenylmethyl)acetate dihydrochloride The reaction is carried out in a mixture of anhydrous methanol/dioxane/ethereal hydrochloric acid (1:1:1). After 4 hours, the precipitate is filtered off with suction and dried.

Melting point: 290–300° C.; Mass spectrum: M$^+$=484; R$_f$ value: 0.45 (silica gel; methylene chloride/methanol/concentrated ammonia=4:1:0.2)

(46) [4-Hydroxy-1-[2-[[4-(piperidin-4-yl)-piperazin-1-yl]-carbonyl]-ethyl]-piperidin-4-yl]-acetic acid trihydrochloride Prepared from tert-butyl [1-[2-[[4-(piperidin-4-yl)-piperazin-1-yl]-carbonyl]-ethyl]-4-hydroxy-piperidin-4-yl]acetate with ethereal hydrochloric acid. The trihydrochloride is prepared with 1N hydrochloric acid.

Mass spectrum: (M+H)$^+$=383; R$_f$ value: 0.12 (silica gel; methylene chloride/methanol/concentrated ammonia=2:1:0.25)

EXAMPLE 3

Methyl [4-trans-[3-[4-(4-piperidinyl)-piperazin-1-yl] propionyl]-amino]cyclohexanecarboxylate 0.8 g (0.0017 mol) of methyl [4-trans-[3-[4-(4-(1-benzyl)-piperidinyl)-piperazin-1-yl]propionyl]amino]cyclohexane-carboxylate is exhaustively hydrogenated in 20 ml of methanol at room temperature under a hydrogen pressure of 50 psi over palladium dihydroxide-on-charcoal as the catalyst. The catalyst is filtered off with suction and the solution is concentrated to a small volume. The crystals which have separated out are filtered off with suction.

Yield: 0.42 g (65% of theory); Melting point: 173–178° C.; Mass spectrum: M$^+$=380; R$_f$ value: 0.18 (silica gel; methylene chloride/methanol/concentrated ammonia=4:1:0.2)

The following compounds can be prepared analogously to Example 3:

(1) Methyl N-[[-(4-piperidinyl)-piperazin-1-yl]carbonyl]-3-(4-piperidinyl)-propionate dihydrochloride Prepared from methyl N-[[4-(4-(1-benzyl)-piperidinyl)-piperazin-1-yl]carbonyl]-3-(4-piperidinyl)-propionate dihydrochloride by hydrogenation over palladium-on-charcoal (10%).

Melting point: 284-286° C. (decomposition); R$_f$ value: 0.10 (silica gel; methylene chloride/methanol=9:1)

(2) Methyl N-[[4-(4-piperidinyl)-piperazin-1-yl]acetyl]-4-piperidinyloxyacetate trihydrochloride Prepared from methyl N-[[4-(4-(1-benzyl)-piperidinyl)-piperazin-1-yl]acetyl]-4-piperidinyloxyacetate by hydrogenation over palladium-on-charcoal (10%). Amorphous solid Mass spectrum: M$^+$=382; R$_f$ value: 0.32 (silica gel; methylene chloride/methanol/concentrated ammonia=4:1:0.2)

(3) Methyl N-[[4-(4-piperidinyl)-piperazin-1-yl]acetyl]-4-piperidinylacetate trihydrochloride Prepared from methyl N-[[4-(4-(1-benzyl)-piperidinyl)-piperazin-1-yl]acetyl]-4-piperidinylacetate by hydrogenation over palladium-on-charcoal (10%).

Melting point: 250–253° C.; Mass spectrum: M$^+$=366; R$_f$ value: 0.35 (silica gel; methylene chloride/methanol/concentrated ammonia=2:1:0.25)

(4) Methyl N-[[4-(4-piperidinyl)-piperazin-1-yl]acetyl] piperazinoacetate tetrahydrochloride Prepared from methyl N-[[4-(4-(1-benzyl)-piperidinyl)-piperazin-1-yl]acetyl]piperazinoacetate by hydrogenation over palladium-on-charcoal (10%).

Melting point: 130–135° C. (decomposition); Mass spectrum: M$^+$=367; R$_f$ value: 0.065 (silica gel; methylene chloride/methanol=9:1)

(5) Methyl [4-trans-[[4-(4-piperidinyl)-piperazin-1-yl]acetyl]amino]-cyclohexanecarboxylate trihydrochloride Prepared from methyl [4-trans[[4-(4-(1-benzyl)-piperidinyl)-piperazin-1-yl]acetyl]amino]cyclohexanecarboxylate trihydrochloride by hydrogenation over palladium-on-charcoal (10%).

Melting point: 275–277° C. (decomposition); Mass spectrum: M$^+$=366;

(6) Methyl N-[[4-(4-piperidinyl)-piperazin-1-yl]acetyl]-3-(4-piperidinyl)-propionate trihydrochloride Prepared from methyl N-[[4-(4-(1-benzyl)-piperidinyl)-piperazin-1-yl]acetyl]-3-(4-piperidinyl)-propionate trihydrochloride by hydrogenation over palladium-on-charcoal.

Melting point: 247–249° C. (decomposition); Mass spectrum: M$^+$=380;

(7) Methyl [4-[[4-(4-piperidinyl)-piperazin-1-yl]carbonylamino]phenoxy]acetate dihydrochloride Prepared from methyl [4-[[4-(4-(1-benzyl)-piperidinyl)-piperazin-1-yl]carbonylamino]phenoxy]acetate by hydrogenation over palladium dihydroxide-on-charcoal.

Melting point: 266–269° C.; Mass spectrum: M$^+$=376; R$_f$ value: 0.65 (reversed phase plate RP18; methanol/5% strength sodium chloride solution)

(8) 1-[[4-(4-piperidinyl)-piperazin-1-yl]carbonyl]-[(piperidin-4-yl)-carbonyl]glycine ethyl ester dihydrochloride Prepared from N-[[4-(4-(1-benzyl)-piperidinyl)-piperazin-1-yl]carbonyl]-[(piperidin-4-yl)-carbonyl]glycine ethyl ester and palladium-on-charcoal (10%) as the catalyst.

Melting point: 295–296° C. (decomposition); Mass spectrum: M$^+$=409; R$_f$ value: 0.50 (silica gel; methylene chloride/methanol/concentrated ammonia=2:1:0.25)

(9) Pivaloyloxymethyl [4-[[4-(4-piperidinyl)-piperazin-1-yl]carbonylamino]phenoxy]acetate Prepared from pivaloyloxymethyl [4-[[4-(4-(1-benzyl)-piperidinyl)-piperazin-1-yl]carbonylamino]phenoxy]acetate by hydrogenation over palladium dihydroxide-on-charcoal.

(10) (1-Ethoxy)-carbonyloxyethyl [4-[[4-(4-piperidinyl)-piperazin-1-yl]carbonylamino]phenoxy]acetate Prepared from (1-ethoxy)-carbonyloxyethyl[4-[[4-(4-(1-benzyl)-piperidinyl)-piperazin-1-yl]carbonylamino]-phenoxy]acetate by hydrogenation over palladium dihydroxide-on-charcoal.

(11) tert-Butyl [4-[[4-(4-piperidinyl)-piperazin-1-yl] carbonylamino]-phenoxy]acetate dihydrochloride Prepared from tert-butyl [4-[[4-[4-(1-benzyl)-piperidinyl)-piperazin-1-yl]carbonylamino]-phenoxy] acetate by hydrogenation over palladium-on-charcoal (10%) in water.

Melting point: 288–290° C. (decomposition); Mass spectrum: (M+H)$^+$=419; R$_f$ value: 0.08 (silica gel; methylene chloride/methanol/concentrated ammonia=9:1:0.1)

(12) N-[4-[[4-(4-Piperidinyl)-piperazin-1-yl)]carbonyl]-phenyl]-β-alanine ethyl ester dihydrochloride Prepared from N-[4-[[4-(4-(1-benzyl)-piperidinyl)-piperazin-1-yl]carbonyl]phenyl]-β-alanine ethyl ester dihydrochloride by hydrogenation over palladium-on-charcoal (10%).

Melting point: 286–290° C.; Mass spectrum: M$^+$=388;

(13) tert-Butyl N-[[2S-(4-(4-piperidinyl)-piperazin-1-yl)]-(3-(4-methoxyphenyl))propionyl]-4-piperidinyloxyacetate Prepared from tert-butyl N-[[2S-(4-(4-(1-benzyl)-piperidinyl)-piperazin-1-yl)]-(3-(4-methoxyphenyl)) propionyl]-4-piperidinyloxyacetate by hydrogenation over palladium-on-charcoal (10%).

(14) tert-Butyl [4-trans-[4-(4-piperidinyl)-piperazin-1-yl] carbonylamino]cyclohexyloxy]acetate Prepared from tert-butyl [4-trans-[4-(4-(1-benzyl)-piperidinyl)-piperazin-1-yl]carbonylamino]cyclohexyloxy]-acetate by hydrogenation over palladium-on-charcoal (10%).

Melting point: 139–141° C. (decomposition); Mass spectrum: M$^+$=424;

(15) N-[4-trans-[4-(4-Piperidinyl)-piperazin-1-yl)] carbonyl]-aminocyclohexyl]glycine trihydrochloride Prepared from N-benzyl-N-[4-trans-[4-(4-piperidinyl)-piperazin-1-yl)]carbonylaminocyclohexyl]glycine trihydrochloride by hydrogenation over palladium-on-charcoal (10%). Amorphous solid.

Mass spectrum: (M+H)$^+$=368; R$_f$ value: 0.095 (silica gel; methylene chloride/methanol/concentrated ammonia=2:1:0.25)

(16) tert-Butyl 3-[4-trans-[[4-(4-piperidinyl)-piperazin-1-yl)]carbonylamino]cyclohexyl]propionate Prepared from tert-butyl 3-[4-trans-[[4-(4-(1-benzyl)-piperidinyl)-piperazin-1-yl)]carbonylamino]-cyclohexyl] propionate by hydrogenation over palladium-on-charcoal (10%).

R$_f$ value: 0.16 (silica gel; methylene chloride/methanol/concentrated ammonia=4:1:0.2)

(17) Ethyl [4-[[4-(3-pyrrolidinyl)-piperazin-1-yl]-carbonylamino]-phenoxy]acetate The solvent is evaporated off and the crude product is chromatographed over silica gel.

Mass spectrum: M$^+$=376; R$_f$ value: 0.30 (silica gel; methylene chloride/methanol/concentrated ammonia=4:1:0.25)

(18) Ethyl 4-[4-[[4-(piperidin-4-yl)-piperazin-1-yl]-carbonyl]-piperidin-1-yl]butyrate A solution of 0.65 g of ethyl 4-[4-[[4-(1-benzyl-piperidin-4-yl)-piperazin-1-yl]-carbonyl]-piperidin-1-yl]butyrate in 40 ml of ethanol is hydrogenated in the presence of 0.2 g of palladium-on-active charcoal under a pressure of 50 psi at room temperature. The catalyst is filtered off and the solvent is evaporated off under reduced pressure. The residue is chromatographed over silica gel with methylene chloride/methanol/concentrated ammonia (4:1:0.2).

Yield: 0.31 g (59% of theory), Mass spectrum: $M^+$=394; $R_f$ value: 0.40 (silica gel; methylene chloride/methanol/concentrated ammonia=4:1:0.2)

(19) Ethyl [4-[2-[[4-(piperidin-4-yl)-piperazin-1-yl]-carbonyl]-ethyl]-piperidin-1-yl]acetate Prepared analogously to Example 3(17)

Melting point: from 240° C. sintering; Mass spectrum: $M^+$=394; $R_f$ value: 0.39 (silica gel; methylene chloride/methanol/concentrated ammonia=4:1:0.2)

(20) Methyl 3-[[4-[[4-(piperidin-4-yl)-piperazin-1-yl]-carbonyl]-piperidin-1-yl]-carbonyl] propionate hydrochloride The hydrogenation is carried out in methanol with the addition of one molar equivalent of 1M hydrochloric acid. The residue is triturated with a little ethyl acetate/methanol and filtered off with suction.

Melting point: from 275° C. sintering; Mass spectrum: $M^+$=394; $R_f$ value: 0.41 (silica gel; methylene chloride/methanol/concentrated ammonia=4:1:0.2)

(21) Methyl [4-[[4-(piperidin-4-yl)-piperazin-3-on-1-yl]-carbonylamino]-phenoxy]acetate

(22) Ethyl [4-[[2-methyl-4-(piperidin-4-yl)-piperazin-3-on-1-yl]-carbonylamino]-phenoxy]acetate

(23) Ethyl [4-[[2-methyl-4-(piperidin-4-yl)-piperazin-1-yl]-carbonylamino]-phenoxy]acetate

(24) Methyl [4-[[2-[[4-methoxy-phenyl]-methyl]-4-(piperidin-4-yl)-piperazin-3-on-1-yl]-carbonylamino]-phenoxy]acetate

(25) Methyl [4-[[4-(piperidin-4-yl)-tetrahydroquinoxalin-1-yl]-carbonylamino]-phenoxy]-acetate

(26) Methyl 4-[[4-(piperidin-4-yl)-piperazine-2,5-dion-1-yl]-methylcarbonyl]-phenoxy]-acetate

(27) Cyclohexyl [4-[2-[[4-(pyrrolidin-3-yl)-piperazin-1-yl]-carbonyl]-ethyl]-piperidin-1-yl]acetate Prepared analogously to Example 3(18).

Mass spectrum: $M^+$=434; $R_f$ value: 0.48 (silica gel; methylene chloride/methanol/concentrated ammonia=4:1:0.25)

(28) tert-Butyl [1-[2-[[4-(piperidin-4-yl)-piperazin-1-yl]-carbonyl]-ethyl]-4-hydroxy-piperidin-4-yl]acetate Prepared analogously to Example 3(18).

Mass spectrum: $M^+$=438; $R_f$ value: 0.27 (silica gel; methylene chloride/methanol/concentrated ammonia=4:1:0.25)

EXAMPLE 4

Cyclohexyl 3-[4-trans-[[4-(4-piperidinyl)-piperazin-1-yl]carbonylamino]-cyclohexylpropionate dihydrochloride A weak stream of hydrochloric acid gas is passed through a suspension of 300 mg (0.7 mmol) of 3-[4-trans-[[4-(4-piperidinyl)-piperazin-1-yl]carbonylamino]cyclohexyl] propionic acid dihydrochloride in 20 ml of cyclohexanol for half an hour. After about 5 minutes, a clear solution occurs. The solution is left to stand overnight at room temperature and is then heated at the reflux temperature for a further two hours. After cooling, the mixture is poured onto ether and the precipitate is filtered off with suction.

Yield: 240 mg (67.4% of theory), Melting point: 324–326° C.; Mass spectrum: $M^+$=448; $R_f$ value: 0.55 (silica gel; methylene chloride/methanol/concentrated ammonia= 2:1:0.25)

The following compounds can be prepared analogously to Example 4:

(1) Isobutyl 3-[4-trans-[[4-(4-piperidinyl)-piperazin-1-yl] carbonylamino]cyclohexyl]propionate dihydrochloride Prepared from 3-[4-trans-[[4-(4-piperidinyl)-piperazin-1-yl]carbonylamino]cyclohexyl]propionic acid dihydrochloride and isobutanol.

Melting point: >315° C.; Mass spectrum: $M^+$=422; $R_f$ value: 0.47 (silica gel; methylene chloride/methanol/concentrated ammonia=2:1:0.25)

(2) Isobutyl 3-[4-[4-(4-piperidinyl)-piperazin-1-yl] carbonylamino]piperidinopropionate trihydrochloride Prepared from 3-[4-[4-(4-piperidinyl)-piperazin-1-yl] carbonylamino]piperidinopropionic acid dihydrochloride and isobutanol.

(3) Cyclohexyl 3-[4-[4-(4-piperidinyl)-piperazin-1-yl] carbonylamino]piperidino propionate trihydrochloride Prepared from 3-[4-[4-(4-piperidinyl)-piperazin-1-yl] carbonylamino]piperidinopropionic acid dihydrochloride and cyclohexanol.

(4) Isobutyl 4-[[4-(4-piperidinyl)-piperazin-1-yl] carbonylamino]piperidinoacetate trihydrochloride Prepared from 4-[[4-(4-piperidinyl)-piperazin-1-yl] carbonylamino]piperidinoacetic acid dihydrochloride and isobutanol.

(5) Cyclohexyl 4-[[4-(4-piperidinyl)-piperazin-1-yl] carbonylamino]piperidinoacetate trihydrochloride Prepared from 4-[[4-(4-piperidinyl)-piperazin-1-yl] carbonylamino]piperidinoacetic acid dihydrochloride and cyclohexanol.

(6) Isopropyl [4-[[4-(4-piperidinyl)-piperazin-1-yl] carbonylamino]-phenoxy]acetate dihydrochloride Prepared from [4-[[4-(4-piperidinyl)-piperazin-1-yl] carbonyl-amino]-phenoxy]acetic acid dihydrochloride and isopropanol.

Melting point: 296–298° C. (decomposition); Mass spectrum: $(M+H)^+$=405; $R_f$ value: 0.38 (silica gel; methylene chloride/methanol/concentrated ammonia=2:1:0.25)

(7) Isobutyl [4-[[4-(4-piperidinyl)-piperazin-1-yl] carbonylamino]-phenoxy]acetate dihydrochloride Prepared from [4-[[4-(4-piperidinyl)-piperazin-1-yl] carbonyl-amino]-phenoxy]acetic acid dihydrochloride and isobutanol.

Melting point: 308–310° C. (decomposition); Mass spectrum: $(M+H)^+$=419; $R_f$ value: 0.50 (silica gel; methylene chloride/methanol/concentrated ammonia=2:1:0.25)

(8) Neopentyl [4-[[4-(4-piperidinyl)-piperazin-1-yl] carbonylamino]-phenoxy]acetate dihydrochloride Prepared from [4-[[4-(4-piperidinyl)-piperazin-1-yl] carbonylamino]-phenoxy]acetic acid dihydrochloride and neopentyl alcohol.

Melting point: 250–252° C. (decomposition); Mass spectrum: $(M+H)^+$=433; $R_f$ value: 0.45 (silica gel; methylene chloride/methanol/concentrated ammonia=2:1:0.25)

(9) Cyclopentyl [4-[[4-(4-piperidinyl)-piperazin-1-yl] carbonylamino]-phenoxy]acetate dihydrochloride Prepared from [4-[[4-(4-piperidinyl)-piperazin-1-yl] carbonyl-amino]-phenoxy]acetic acid dihydrochloride and cyclopentanol.

Melting point: 298–300° C. (decomposition); Mass spectrum: $(M+H)^+$=431; $R_f$ value: 0.65 (silica gel; methylene chloride/methanol/concentrated ammonia=2:1:0.2)

(10) Cycloheptyl [4-[[4-(4-piperidinyl)-piperazin-1-yl] carbonylamino]-phenoxy]acetate dihydrochloride Prepared from [4-[[4-(4-piperidinyl)-piperazin-1-yl] carbonyl-amino]-phenoxy]acetic acid dihydrochloride and cycloheptanol. Resin Mass spectrum: $(M+H)^+=459$; $R_f$ value: 0.65 (silica gel; methylene chloride/methanol/concentrated ammonia= 2:1:0.2)

(11) Butyl [4-[[4-(4-piperidinyl)-piperazin-1-yl] carbonylamino]-phenoxy]acetate dihydrochloride Prepared from [4-[[4-(4-piperidinyl)-piperazin-1-yl] carbonyl-amino]-phenoxy]acetic acid dihydrochloride and 1-butanol.

Melting point: 300–301° C. (decomposition); Mass spectrum: $(M+H)^+=419$; $R_f$ value: 0.50 (silica gel; methylene chloride/methanol/concentrated ammonia=2:1:0.25)

(12) Cyclohexyl [4-[[4-(4-piperidinyl)-piperazin-1-yl] carbonylamino]-phenoxy]acetate dihydrochloride Prepared from [4-[[4-(4-piperidinyl)-piperazin-1-yl] carbonyl-amino]-phenoxy]acetic acid dihydrochloride and cyclohexanol.

Melting point: 291–293° C. (decomposition); Mass spectrum: $(M+H)^+=445$; $R_f$ value: 0.35 (silica gel; methylene chloride/methanol/concentrated ammonia=4:1:0.2)

(13) Ethyl [4-[[4-(4-piperidinyl)-piperazin-1-yl] carbonylamino]-phenoxy]acetate dihydrochloride Prepared from [4-[[4-(4-piperidinyl)-piperazin-1-yl] carbonyl-amino]-phenoxy]acetic acid dihydrochloride and ethanol.

Melting point: 288–290° C. (decomposition); Mass spectrum: $(M+H)^+=391$; $R_f$ value: 0.35 (silica gel; methylene chloride/methanol/concentrated ammonia=4:1:0.2)

(14) Methyl [4-(4-trans-[4-(4-piperidinyl)-piperazin-1-yl] carbonylaminocyclohexyloxy]acetate dihydrochloride Prepared from [4-trans-[4-(4-piperidinyl)-piperazin-1-yl] carbonylaminocyclohexyloxy]acetic acid dihydrochloride and methanol.

(15) Ethyl N-[[2S-(4-(4-piperidinyl)-piperazin-1-yl)]-(3-(4-methoxyphenyl))propionyl]-4-piperidinyloxyacetate Prepared from N-[[2S-(4-(4-piperidinyl)-piperazin-1-yl)]-(3-(4-methoxyphenyl))propionyl]-4-piperidinyloxyacetic acid trihydrochloride and ethanol.

Melting point: Mass spectrum: $(M+H)^+=517$; $R_f$ value: 0.15 (silica gel; methylene chloride/methanol/concentrated ammonia=2:1:0.25)

(16) Ethyl [4-trans-[4-(4-piperidinyl)-piperazin-1-yl] carbonylamino-cyclohexyloxy]acetate dihydrochloride Prepared from [4-trans-[4-(4-piperidinyl)-piperazin-1-yl] carbonylaminocyclohexyloxy]acetic acid dihydrochloride and ethanol.

(17) Isopropyl [4-trans-[4-(4-piperidinyl)-piperazin-1-yl] carbonylaminocyclohexyloxy]acetate dihydrochloride Prepared from [4-trans-[4-(4-piperidinyl)-piperazin-1-yl] carbonylaminocyclohexyloxy]acetic acid dihydrochloride and isopropanol.

(18) Isobutyl [4-trans-[4-(4-piperidinyl)-piperazin-1-yl] carbonylamino-cyclohexyloxy]acetate dihydrochloride Prepared from [4-trans-[4-(4-piperidinyl)-piperazin-1-yl] carbonylaminocyclohexyloxy]acetic acid dihydrochloride and isobutanol.

Melting point: 316–320° C. (decomposition); Mass spectrum: $(M+H)^+=425$; $R_f$ value: 0.40 (silica gel; methylene chloride/methanol/concentrated ammonia=2:1:0.25)

(19) Cyclohexyl [4-trans-[4-(4-piperidinyl)-piperazin-1-yl] carbonylamino-cyclohexyloxy]acetate dihydrochloride Prepared from [4-trans-[4-(4-piperidinyl)-piperazin-1-yl] carbonylaminocyclohexyloxy]acetic acid dihydrochloride and cyclohexanol.

Melting point: 311–314° C. (decomposition); Mass spectrum: $(M+H)^+=451$; $R_f$ value: 0.40 (silica gel; methylene chloride/methanol/concentrated ammonia=2:1:0.25)

(20) Cyclopentyl [4-trans-[4-(4-piperidinyl)-piperazin-1-yl] carbonylamino-cyclohexyloxy]acetate dihydrochloride Prepared from [4-trans-[4-(4-piperidinyl)-piperazin-1-yl] carbonylaminocyclohexyloxy]acetic acid dihydrochloride and cyclopentanol.

Melting point: 309–311° C. (decomposition); Mass spectrum: $(M+H)^+=437$; $R_f$ value: 0.40 (silica gel; methylene chloride/methanol/concentrated ammonia=2:1:0.25)

(21) Butyl [4-trans-[4-(4-piperidinyl)-piperazin-1-yl] carbonylamino-cyclohexyloxy]acetate dihydrochloride Prepared from [4-trans-[4-(4-piperidinyl)-piperazin-1-yl] carbonylaminocyclohexyloxy]acetic acid dihydrochloride and 1-butanol.

EXAMPLE 5

N-tert-Butyloxycarbonyl-N-[[4-[4-(4-(1-tert-butyloxycarbonyl)-piperidinyl)-piperazin-1-yl] carbonyl]piperidinyl]-S-alanine methyl ester A mixture of 4.2 g (0.0068 mol) of crude N-tert-butyloxycarbonyl-N-[4-[1-(4-nitrophenyloxycarbonyl)-piperidinyl]]-β-alanine methyl ester, 1.8 g (0.0068 mol) of N-[4-(1-tert-butyloxycarbonyl)-piperidinyl]piperazine and 2.3 ml (0.0136 mol) of N-ethyl-diisopropylamine is heated at 140° C. for 4 hours. After cooling, the mixture is partitioned between ethyl acetate and water and the organic phase is washed with sodium bicarbonate solution, dried and concentrated. The residue is purified over a silica gel column (eluting agent: methylene chloride with 2.5%, 3% and 4% of methanol).

Yield: 1.3 g of a colourless foam (33.6% of theory), Mass spectrum: $M^+=581$; $R_f$ value: 0.48 (silica gel; methylene chloride/methanol=9:1)

The following compounds can be prepared analogously to Example 5:

(1) N-Acetyl-N-[[4-[4-(4-(1-tert-butyloxycarbonyl)-piperidinyl)-piperazin-1-yl]carbonyl]piperidinyl]-β-alanine methyl ester Prepared from N-acetyl-N-[4-[1-(4-nitrophenyloxycarbonyl)-piperidinyl]]-β-alanine methyl ester (preparation analogous to Example III) and N-[4-(1-tert-butyloxycarbonyl)-piperidyl]-piperazine Yield: 500 mg (9.1% of theory), $R_f$ value: 0.52 (silica gel; methylene chloride/methanol=9:1)

(2) N-[[4-[4-(4-(1-tert-Butyloxycarbonyl)-piperidinyl)-piperazin-1-yl]carbonyl]piperidinyl]-N-methyl-β-alanine methyl ester Prepared from N-methyl-N-[4-[1-(4-nitrophenyloxycarbonyl)-piperidinyl]]-β-alanine methyl ester (preparation analogous to Example III) and N-[4-(1-tert-butyloxycarbonyl)-piperidinyl]-piperazine.

(3) N-tert-Butyloxycarbonyl-N-[[4-[4-(4-(1-tert-butyloxycarbonyl)-piperidinyl)-piperazin-1-yl]carbonyl] piperidinyl]glycine methyl ester Prepared from N-tert-butyloxycarbonyl-N-[4-[1-(4-nitrophenyloxycarbonyl) -piperidinyl]]glycine methyl ester (preparation analogous to Example III) and N-[4-(1-tert-butyloxycarbonyl)-piperidinyl]-piperazine and N-ethyl-diisopropylamine.

(4) N-[[4-[4-(4-(1-tert-Butyloxycarbonyl)-piperidinyl)-piperazin-1-yl]carbonyl]piperidinyl]-N-methyl-glycine methyl ester Prepared from N-methyl-N-[4-[1-(4-nitrophenyloxycarbonyl)-piperidinyl]]-glycine methyl ester (preparation analogous to Example III) and N-[4-(1-tert-butyloxycarbonyl)-piperidinyl]-piperazine and N-ethyl-diisopropylamine.

(5) N-Acetyl-N-[[4-[4-(4-(1-tert-butyloxycarbonyl)-piperidinyl)-piperazin-1-yl]carbonyl]piperidinyl]glycine methyl ester Prepared from N-acetyl-N-[4-[1-(4-nitrophenyloxycarbonyl)-piperidinyl]]-glycine methyl ester (preparation analogous to Example III), N-[4-(1-tert-butyloxycarbonyl)-piperidinyl]-piperazine and N-ethyl-diisopropylamine.

(6) Methyl N-[[4-(4-(1-tert-butyloxycarbonyl)-piperidinyl)-piperazin-1-yl]carbonyl]-4-(4-piperidinyl)]butyrate Prepared from methyl N-(4-nitrophenyloxycarbonyl)-4-(4-piperidinyl)-butyrate and N-[4-(1-tert-butyloxycarbonyl)-piperidinyl]piperazine. $R_f$ value: 0.48 (silica gel; methylene chloride/methanol=9:1)

(7) Ethyl N-[[4-(4-(1-tert-butyloxycarbonyl)-piperidinyl)-piperazin-1-yl]carbonyl]-3-(piperidin-4-yloxy)-propionate Prepared from ethyl N-(4-nitrophenyloxycarbonyl)-3-(piperidin-4-yloxy)-propionate (preparation analogous to Example III) and N-[4-(i-tert-butyloxycarbonyl)-piperidinyl]piperazine. Oil $R_f$ value: 0.60 (silica gel; methylene chloride/methanol= 9:1)

(8) N-[[4-(4-(1-tert-butyloxycarbonyl)-piperidinyl)-piperazin-1-yl]carbonyl]-piperidin-4-yl)-carbonyl]-9-alanine ethyl ester Prepared from N-[1-(4-nitrophenyloxycarbonyl)-piperidin-4-yl)carbonyl]-β-alanine ethyl ester (preparation analogous to Example III) and N-[-(1-tert-butyloxycarbonyl)-piperidinyl]-piperazine. Amorphous substance.

$R_f$ value: 0.39 (silica gel; methylene chloride/methanol= 9:1)

(9) Methyl [4-[[4-(4-(1-benzyl)-piperidinyl)-piperazin-1-yl)]carbonyl]phenoxy]acetate Prepared by reaction of 4-methyloxycarbonylmethyloxyaniline with p-nitrophenyl chloroformate in the presence of triethylamine in methyl 4-(4-nitrophenyloxycarbonylamino)-phenoxyacetate and subsequent reaction of this intermediate product with N-(4-(1-benzyl-piperidinyl)]piperazine in the presence of triethylamine.

Yield: 1.2 g (37.3% of theory), Mass spectrum: M$^+$=466; $R_f$ value: 0.40 (silica gel; methylene chloride/methanol/concentrated ammonia=9:1:0.1)

(10) Methyl [N-[4-(4-(1-benzyl)-piperidinyl)-piperazin-1-yl)]carbonyl]piperidine-4-carboxylate Prepared by reaction of methyl piperidine-4-carboxylate with p-nitro-phenyl chloroformate in the presence of triethylamine to give methyl N-(4-nitrophenyloxycarbonyl)-piperidine-4-carboxylate and subsequent reaction of this intermediate product with (4-(1-benzyl)-piperidinyl)-piperazine.

EXAMPLE 6

Methyl [3-[4-trans-[4-[4-(1-tert-butyloxycarbonyl)-piperidinyl]piperazin-1-yl]carbonylamino] cyclohexyl]-propionate A solution of 2.5 g (0.0093 mol) of methyl 3-[4-(trans-aminocyclohexyl]propionate in 20 ml of absolute dimethylformamide is added dropwise to a solution of 2 g (0.0123 mol) of N,N'-carbonyldiimidazole and 1.2 g (0.0176 mol) of imidazole in 150 ml of absolute dimethylformamide at −5° C., while stirring, and the mixture is stirred at −5° C. for a further hour and then at room temperature for 3 hours. A solution of 3 g (0.0135 mol) of N-[4-(1-tert-butyloxycarbonyl)piperidinyl]piperazine in 20 ml of absolute dimethylformamide is then added dropwise and the mixture is stirred overnight at room temperature. It is concentrated to dryness in vacuo and the residue is purified over a silica gel column, methylene chloride containing 2% and 4% of methanol being used as the eluting agent.

Yield: 1.75 g (32.3% of theory), Mass spectrum: M$^+$=480; $R_f$ value: 0.50 (silica gel; methylene chloride/methanol=9:1)

The following compound can be prepared analogously to Example 6:

(1) Methyl [4-[4-(4-(1-tert-butyloxycarbonyl)-piperidinyl)-piperazin-1-yl]carbonylamino]-piperidinoacetate Prepared from N-[4-(1-tert-butyloxycarbonyl) piperidinyl)-piperazine, methyl 4-aminopiperidinoacetate dihydrochloride, N,N'-carbonyldiimidazole and imidazole. $R_f$ value: 0.30 (silica gel; methylene chloride/methanol=9:1)

EXAMPLE 7

Methyl [4-trans-[4-(4-(1-tert-butyloxycarbonyl) piperidinyl)-piperazin-1yl]malonylamino] cyclohexylcarboxylate Prepared from 4-[(4-(1-tert-butyloxycarbonyl) piperidinyl)-piperazin-1-yl]malonic acid, methyl trans-4-aminocyclohexylcarboxylate hydrochloride, 2-(1H-benzotriazol-1yl)-1,1,3,3-tetramethyluronium tetrafluoroborate, 1-hydroxy-1H-benzotriazole and triethylamine in dry dimethylformamide analogously to Example XIIIa.

Yield: 0.6 g (35.9% of theory), Mass spectrum: (M+H)$^+$= 495; $R_f$ value: 0.48 (silica gel; methylene chloride/methanol/concentrated ammonia=9:1:0.1)

The following compounds can be prepared analogously to Example 7:

(1) Ethyl 3-[[4-(4-(1-tert-butyloxycarbonyl)-piperidinyl)-piperazin-1-yl]carbonyl]phenoxy]propionate Prepared from [4-(1-tert-butyloxycarbonyl)piperidinyl]-piperazine hydrochloride, 4-[2-(ethoxycarbonylethyl)oxy]-benzoic acid, 2-(1H-benzotriazol-1-yl)-1,1,3,3-tetramethyl-uronium tetrafluoroborate and triethylamine in dry dimethylformamide analogously to Example XIIIa. Oil. $R_f$ value: 0.43 (silica gel; methylene chloride/methanol=9:1)

(2) Ethyl 3-[3-[[4-(4-(1-tert-butyloxycarbonyl)piperidinyl)-piperazin-1-yl]carbonyl]phenoxy]propionate Prepared from [4-(1-tert-butyloxycarbonyl)piperidinyl)-piperazine hydrochloride, 3-[2-(ethoxycarbonylethyl)oxy]-benzoic acid, 2-(1H-benzotriazol-1-yl)-1,1,3,3-tetramethyluronium tetrafluoroborate and triethylamine analogously to Example XIIIa. Oil;

$R_f$ value: 0.65 (silica gel; methylene chloride/methanol= 9:1)

(3) Methyl N-4-[[4-[4-(4-(1-tert-butyloxycarbonyl)-piperidinyl)piperazin-1-yl)]carbonylethyl]piperidiny] acetate Prepared from [4-(1-tert-butyloxycarbonyl)piperidinyl]-piperazine hydrochloride, 3-[(4-methoxycarbonylmethyl)-piperidinyl]propionic acid hydrochloride, triethylamine and 2-(1H-benzothiazol-1yl)-1,1,3,3-tetramethyluronium tetrafluoroborate analogously to Example XIIIa.

Melting point: 214–216° C. (decomposition); $R_f$ value: 0.40 (silica gel; methylene chloride/methanol/concentrated ammonia=9:1:0.1)

(4) Methyl N-4-[[4-[4-(4-(1-tert-butyloxycarbonyl)-piperidinyl)piperazin-1-yl)]malonyl]piperidiny]acetate Prepared from 4-[(4-(1-tert-butyloxycarbonyl) piperidinyl)-piperazin-1-yl)]malonic acid, methyl 4-piperidinylacetate hydrochloride, triethylamine and 2-(1H-benzotriazol-1yl)-1,1,3,3-tetramethyluronium tetrafluoroborate analogously to Example XIIIa. Oil;

$R_f$ value: 0.60 (silica gel; methylene chloride/methanol/concentrated ammonia=9:1:0.1).

(5) Methyl N-4-[[4-[4-(1-tert-butyloxycarbonyl)piperidinyl)-piperazin-1yl)]ethylenecarbonyl]piperidinyl]acetate Prepared from 3-[4-[(4-(1-tert-butyloxycarbonyl)piperidinyl)-piperazin-1-yl)]propionic acid, methyl 4-piperidinylacetate hydrochloride, triethylamine and 2-(1H-benzotriazol-1yl)-1,1,3,3-tetramethyluronium tetrafluoroborate analogously to Example XIIIa.

$R_f$ value: 0.42 (silica gel; methylene chloride/methanol/concentrated ammonia=9:1:0.1)

(6) Methyl [4-trans-[4-(4-(1-tert-butyloxycarbonyl)-piperidinyl)piperazin-1-yl)]oxalylamino]cyclohexanecarboxylate Prepared from [4-(4-(1-tert-butyloxycarbonyl)piperidinyl)-piperazin-1-yl)]oxalic acid, methyl trans-4-aminocyclohexanecarboxylate hydrochloride, triethylamine and 2-(1H-benzotriazol-1-yl)-1,1,3,3-tetramethyluronium tetrafluoroborate analogously to Example XIIIa.

Mass spectrum: $M^+$=480; $R_f$ value: 0.55 (silica gel; methylene chloride/methanol/concentrated ammonia=9:1:0.1)

(7) Methyl N-[[4-[4-(1-tert-butyloxycarbonyl)-piperidinyl)-piperazin-1-yl)]oxalyl]-4-piperidinyloxyacetate Prepared from [4-(4-(1-tert-butyloxycarbonyl)-piperidinyl)-piperazin-1yl)]oxalic acid, methyl 4-piperidinyloxyacetate hydrochloride, triethylamine and 2-(1H-benzotriazol-1yl)-1,1,3,3-tetramethyluronium tetrafluoroborate analogously to Example XIIIa.

(8) Methyl [4-[[4-[4-(1-tert-butyloxycarbonyl)piperidinyl)-piperazin-1-yl]carbonylmethyl]phenoxy]acetate Prepared from [4-(1-tert-butyloxycarbonyl)piperidinyl)-piperazine hydrochloride, 4-methoxycarbonylmethyloxyphenylacetic acid, 2-(1H-benzotriazol-1yl)-1,1,3,3-tetramethyluronium tetrafluoroborate and triethylamine analogously to Example XIIIa. Oil Mass spectrum: $M^+$=475;

(9) Methyl N-[4-trans-[3-[4-(1-benzyl)piperidinyl)piperazin-1-yl]-propionyl]amino]cyclohexanecarboxylate Prepared from [3-[4-[4-(1-benzyl)piperidinyl)piperazin-1-yl]propionic acid dihydrochloride, methyl 4-trans-aminocyclohexylcarboxylate hydrochloride, 2-(1H-benzotriazol-1-yl)-1,1,3,3-tetramethyluronium tetrafluoroborate, 1-hydroxy-1H-benzotriazole and N-methylmorpholine analogously to Example XIIIa.

Mass spectrum: $(M+H)^+$=471; $R_f$ value: 0.65 (silica gel; methylene chloride/methanol/concentrated ammonia=4:1:0.2)

(10) Methyl N-[[4-(4-(1-benzyl)piperidinyl)piperazin-1-yl]acetyl]-4-piperidinyloxyacetate trihydrochloride Prepared from 4-[(4-(1-benzyl)piperidinyl)piperazin-1-yl]acetic acid, methyl 4-piperidinyloxyacetate hydrochloride, 2-(1H-benzotriazol-1-yl)-1,1,3,3-tetramethyluronium tetrafluoroborate and triethylamine analogously to Example XIIIa.

Mass spectrum: $M^+$=472; $R_f$ value: 0.40 (silica gel; methylene chloride/methanol/concentrated ammonia=9:1:0.1)

(11) Methyl N-[[4-(4-(1-benzyl)piperidinyl)piperazin-1-yl]acetyl]-4-piperidinylacetate trihydrochloride Prepared from 4-[(4-(1-benzyl)piperidinyl)piperazin-1-yl]acetic acid, methyl 4-piperidinyloxyacetate hydrochloride, 2-(1H-benzotriazol-1-yl)-1,1,3,3-tetramethyluronium tetrafluoroborate and triethylamine analogously to Example XIIIa.

Mass spectrum: $M^+$=456; $R_f$ value: 0.38 (silica gel; methylene chloride/methanol/concentrated ammonia=9:1:0.1)

(12) Methyl N-[[[4-(4-(1-benzyl)piperidinyl)piperazin-1-yl]acetyl]piperazin-1-yl]acetate tetrahydrochloride Prepared from 4-[4-(1-benzyl)piperidinyl)piperazin-1-yl]acetic acid, methyl piperazinoacetate dihydrochloride, 2-(1H-benzotriazol-1yl)-1,1,3,3-tetramethyluronium tetrafluoroborate and triethylamine analogously to Example XIIIa.

(13) Ethyl [4-trans-[4-(4-(1-benzyl)piperidinyl)piperazin-1-yl]acetylamino]cyclohexanecarboxylate trihydrochloride Prepared from 4-[4-(1-benzyl)piperidinyl)piperazin-1-yl]acetic acid, methyl 4-trans-aminocyclohexanecarboxylate hydrochloride, 2-(1H-benzotriazol-1yl)-1,1,3,3-tetramethyluronium tetrafluoroborate and triethylamine analogously to Example XIIIa.

(14) Methyl N-[[4-(4-(1-benzyl)piperidinyl)piperazin-1-yl]acetyl]-3-(4-piperidinyl)propionate trihydrochloride Prepared from 4-[4-(1-benzyl)piperidinyl)piperazin-1-yl]acetic acid, methyl 3-[4-piperidinyl)propionate hydrochloride, 2-(1H-benzotriazol-1yl)-1,1,3,3-tetramethyluronium tetrafluoroborate and triethylamine analogously to Example XIIIa.

(15) [N-[4-(4-(1-Benzyl)piperidinyl)piperazin-1-yl]carbonyl]-[(4-piperidin-4-yl)carbonyl]glycine methyl ester Prepared by reaction of [N-[4-(4-(1-benzyl)piperidinyl)-piperazin-1-yl]carbonyl]piperidine-4-carboxylic acid, glycine methyl ester hydrochloride, 2-(1H-benzotriazol-1-yl)-1,1,3,3-tetramethyluronium tetrafluoroborate and 1-hydroxy-1H-benzotriazole analogously to Example XIIIa.

(16) Ethyl 4-[4-[[4-(1-benzylpiperidin-4-yl)piperazin-1-yl]-carbonyl]piperidin-1-yl]butyrate Prepared from N-(1-benzylpiperidin-4-yl)piperazine, 1-(3-ethoxycarbonyl-propyl)-piperidin-4-yl-carboxylic acid, 2-(1H-benzotriazol-1yl)-1,1,3,3-tetramethyluronium tetrafluoroborate and triethylamine in dry dimethylformamide analogously to Example XIIIa.

Mass spectrum: $M^+$=484; $R_f$ value: 0.21 (silica gel; methylene chloride/methanol/concentrated ammonia=9:1:0.1)

(17) Ethyl [4-[2-[[4-(1-benzylpiperidin-4-yl)piperazin-1-yl]-carbonyl]ethyl]piperidin-1yl]acetate Prepared from N-(1-benzylpiperidin-4-yl)piperazine, 4-[2-(carboxy) ethyl]-1-[(ethoxycarbonyl)methyl] piperidine, 2-(1H-benzotriazol-1-yl)-1,1,3,3-tetramethyluronium tetrafluoroborate and triethylamine in dry dimethylformamide analogously to Example XIIIa. The reaction solution is evaporated under reduced pressure and the residue is partitioned between 0.5N sodium hydroxide solution and ethyl acetate. The organic phase is washed with saturated sodium chloride solution and dried and the solvent is evaporated off under reduced pressure. The residue is chromatographed over silica gel with methylene chloride/methanol/concentrated ammonia (9:1:0.1).

Mass spectrum: $(M+H)^+$=484; $R_f$ value: 0.35 (silica gel; methylene chloride/methanol/concentrated ammonia=9:1:0.1)

(18) Cyclohexyl [4-[2-[[4-[1-(tert-butyloxycarbonyl)piperidin-4-yl]-piperazin-1-yl]carbonyl]ethyl]piperidin-1-yl]acetate Prepared from N-[1-(tert-butyloxycarbonyl)piperidin-4-yl]-piperazine, 4-[2-(carboxy)ethyl]-1-[(cyclohexyloxycarbonyl)-methyl]piperidine, 2-(1H-benzotriazol-1-yl)-1,1,3,3-tetramethyluronium tetrafluoroborate and triethylamine in dry dimethylformamide analogously to Example XIIIa. The reaction solution is evaporated under reduced pressure and the residue is partitioned between 0.5N sodium hydroxide solution and ethyl acetate. The organic phase is washed with saturated sodium chloride solution and dried and the solvent is evaporated off under reduced pressure. The residue is chromatographed over silica gel with methylene chloride/methanol/concentrated ammonia (9:1:0.1).

Mass spectrum: $M^+$=548; $R_f$ value: 0.48 (silica gel; methylene chloride/methanol/concentrated ammonia=9:1:0.1)

(19) Methyl [trans-4-[[-4-[1-(tert-butyloxycarbonyl)piperidin-4-yl]piperazin-1-yl]carbonyl]cyclohexylcarbonylaminolacetate Prepared from trans-4-[[-4-[1-(tert-butyloxycarbonyl)piperidin-4-yl]piperazin-1-yl]carbonyl] cyclohexanecarboxylic acid, glycine methyl ester hydrochloride, 2-(1H-benzotriazol-1yl)-1,1,3,3-tetramethyluronium tetrafluoroborate and triethylamine in dry dimethylformamide analogously to Example XIIIa. The reaction solution is evaporated under reduced pressure and the residue is partitioned between 0.5N sodium hydroxide solution and ethyl acetate. The organic phase is washed with saturated sodium chloride solution and dried and the solvent is evaporated off under reduced pressure. The crude product is reacted further.

Mass spectrum: $M^+$=494; $R_f$ value: 0.40 (silica gel; methylene chloride/methanol/concentrated ammonia=9:1:0.1)

(20) Methyl 3-[[4-[[4-(1-benzylpiperidin-4-yl)piperazin-1-yl]-carbonyl]piperidin-1-yl]carbonyl]propionate Prepared from 1-(4-benzylpiperidin-1-yl)-4-(piperidin-4-yl)-piperazine trihydrochloride, succinic acid monomethyl ester, 2-(1H-benzotriazol-1yl)-1,1,3,3-tetramethyluronium tetrafluoroborate and triethylamine in dry dimethylformamide analogously to Example XIIIa.

Mass spectrum: $M^+$=484; $R_f$ value: 0.35 (silica gel; methylene chloride/methanol/concentrated ammonia=9:1:0.1)

(21) Cyclohexyl [4-[2-[[4-(1-methylpiperidin-4-yl)piperazin-1-yl]carbonyl]ethyl]piperidin-1-yl]acetate Prepared from N-(1-methyl-piperidin-4-yl)-piperazine, 4-[2-(carboxy)ethyl]-1-[(cyclohexyloxycarbonyl)methyl]-piperidine, 2-(1H-benzotriazol-1-yl)-1,1,3,3-tetramethyluronium tetrafluoroborate and triethylamine in dry dimethylformamide analogously to Example XIIIa. The residue is chromatographed over silica gel with methylene chloride/methanol/concentrated ammonia (9:1:0.1).

Mass spectrum: $(M+H)^+$=462; $R_f$ value: 0.14 (silica gel; methylene chloride/methanol/concentrated ammonia=9:1:0.1)

(22) Cyclohexyl [4-[2-[[4-(1-benzylpiperidin-4-yl)piperazin-1-yl]carbonyl]ethyl]piperidin-1-yl]acetate Prepared from N-(1-benzylpiperidin-4-yl)piperazine, 4-[2-(carboxy)ethyl]-1-[(cyclohexyloxycarbonyl)methyl]-piperidine, 2-(1H-benzotriazol-1-yl)-1,1,3,3-tetramethyluronium tetrafluoroborate and triethylamine in dry dimethylformamide analogously to Example XIIIa. The residue is chromatographed over silica gel with methylene chloride/methanol/concentrated ammonia (16:1:0.1).

Mass spectrum: $(M+H)^+$=538; $R_f$ value: 0.50 (silica gel; methylene chloride/methanol/concentrated ammonia=9:1:0.1)

(23) Cyclohexyl [4-[2-[[4-(1-benzylpyrrolidin-3-yl)piperazin-1-yl]carbonyl]ethyl]piperidin-1-yl]acetate Prepared from N-(1-benzylpyrrolidin-3-yl)piperazine, 4-[2-(carboxy)ethyl]-1-[(cyclohexyloxycarbonyl)methyl]-piperidine, 2-(1H-benzotriazol-1-yl)-1,1,3,3-tetramethyluronium tetrafluoroborate and triethylamine in dry dimethylformamide analogously to Example XIIIa. The residue is chromatographed over silica gel with methylene chloride/methanol/concentrated ammonia (16:1:0.1).

Mass spectrum: $M^+$=524; $R_f$ value: 0.39 (silica gel; methylene chloride/methanol/concentrated ammonia=9:1:0.1)

(24) Methyl 4-[[[4-[1-(tert-butyloxycarbonyl)piperidin-4-yl]-piperazin-1-yl]carbonyl]methyloxy]piperidin-1-yl]acetate Prepared from N-[1-(tert-butyloxycarbonyl)piperidin-4-yl]-piperazine, methyl [4-(carboxymethyloxy)-1-piperidyl]-acetate, 2-(1H-benzotriazol-1-yl)-1,1,3,3-tetramethyluronium tetrafluoroborate and triethylamine in dry dimethylformamide analogously to Example XIIIa. The residue is chromatographed over silica gel with methylene chloride/methanol/concentrated ammonia (16:1:0.1).

Mass spectrum: $M^+$=482; $R_f$ value: 0.51 (silica gel; methylene chloride/methanol/concentrated ammonia=9:1:0.1)

(25) tert-Butyl N-[[trans-4-[[4-[1-(tert-butyloxycarbonyl)-piperidin-4-yl]piperazin-1-yl]carbonyl]cyclohexyl]methyl]-N-(phenylsulphonyl)aminoacetate Prepared from N-[1-(tert-butyloxycarbonyl)-piperidin-4-yl]-piperazine, trans-4-[N-(tert-butyloxycarbonylmethyl)-N-(phenyl-sulphonyl)aminomethyl]cyclohexanecarboxylic acid, 2-(1H-benzotriazol-1-yl)-1,1,3,3-tetramethyluronium tetrafluoroborate and triethylamine in dry dimethylformamide analogously to Example XIIIa. The residue is chromatographed over silica gel with methylene chloride/methanol/concentrated ammonia (20:1:0.1).

Mass spectrum: $(M+H)^+$=663; $R_f$ value: 0.26 (silica gel; methylene chloride/methanol/concentrated ammonia=20:1:0.1)

(26) Methyl α-[trans-4-[[1-(tert-butyloxycarbonyl)-piperidin-4-yl]piperazin-1-yl]carbonyl]cyclohexylcarbonylamino]-α-(phenylmethyl)acetate Prepared from trans-4-[[-4-[1-(tert-butyloxycarbonyl)-piperidin-4-yl]-piperazin-1-yl]-carbonyl] cyclohexanecarboxylic acid, D,L-phenylalanine methyl ester, 2-(1H-benzotriazol-1-yl)-1,1,3,3-tetramethyluronium tetrafluoroborate and triethylamine in dry dimethylformamide analogously to Example XIIIa. The reaction solution is evaporated under reduced pressure and the residue is partitioned between 0.5N sodium hydroxide solution and ethyl acetate. The organic phase is washed with saturated sodium chloride solution and dried and the solvent is evaporated off under reduced pressure. The crude product is chromatographed over silica gel with methylene chloride/methanol/concentrated ammonia (9:1:0.1).

Mass spectrum: $M^+$=584; $R_f$ value: 0.55 (silica gel; methylene chloride/methanol/concentrated ammonia=9:1:0.1)

(27) tert-Butyl [1-[2-[[4-(1-benzylpiperidin-4-yl)piperazin-1-yl]carbonyl]ethyl]-4-hydroxypiperidin-4-yl]acetate Prepared from tert-butyl [1-(2-carboxyethyl)-4-hydroxy-piperidin-4-yl]acetate, N-(1-benzyl-piperidin-4-yl) piperazine, 2-(1H-benzotriazol-1-yl)-1,1,3,3-tetramethyluronium tetrafluoroborate and triethylamine in dry dimethylformamide analogously to Example XIIIa. The crude product is chromatographed over silica gel with methylene chloride/methanol/concentrated ammonia (9:1:0.1).

Mass spectrum: $M^+$=528; $R_f$ value: 0.27 (silica gel; methylene chloride/methanol/concentrated ammonia=9:1:0.1)

(28) α-(Aminocarbonylmethyl)-α-[trans-4-[[4-[1-(tert-butyloxy-carbonyl)piperidin-4-yl]piperazin-1-yl]carbonyl]cyclo-hexylcarbonylamino]acetic acid Prepared from trans-4-[[4-[1-(tert-butyloxycarbonyl)piperidin-4-yl]piperazin-1yl]carbonyl] cyclohexanecarboxylic acid, D,L-asparagine silyated in situ (prepared by reacting D,L-asparagine hydrate with 4.5 equivalents of trimethylsilyl chloride and 5 equivalents of N-methylmorpholine in dimethylformamide), 2-(1H-benzotriazol-1-yl)-1,1,3,3-tetramethyluronium tetrafluoroborate and N-methylmorpholine in dry dimethylformamide analogously to Example XIIIa. The crude product is chromatographed over silica gel with methylene chloride/methanol/concentrated ammonia (4:1:0.2).

Mass spectrum: (M+H)⁺=538; $R_f$ value: 0.17 (silica gel; methylene chloride/methanol/concentrated ammonia= 4:1:0.2)

EXAMPLE 8

Methyl 3-[4-[4-[4-(1-tert-butyloxycarbonyl) piperidinyl]-piperazin-1-yl]-carbonylamino] piperidinopropionate 1 g (0.011 mol) of methyl acrylate (1 ml) is added to a solution of 4.3 g (0.011 mol) of 4-[4-[4-[(1-tert-butyloxycarbonyl)piperidinyl]piperazino]carbonylamino]piperidine in 100 ml of methanol at room temperature, while stirring, and the mixture is left to stand at room temperature for 4 hours. It is then concentrated to dryness in vacuo and the residue is purified by chromatography over a silica gel column (eluting agent: methylene chloride/methanol/ concentrated ammonia=9:0.5:0.05).

Yield: 2.5 g (47.8% of theory), Mass spectrum: M⁺=481; $R_f$ value: 0.37 (silica gel; methylene chloride/methanol/ concentrated ammonia=9:1:0.1)

The following compounds can be prepared analogously to Example 8:
(1) [N-[3-[[4-(4-(1-tert-Butyloxycarbonyl)-piperidinyl)-piperazin-1yl]carbonyl]phenyl]-β-alanine ethyl ester Prepared from 3-[[4-(4-(1-tert-butyloxycarbonyl)piperidinyl)-piperazin-1-yl]carbonyl]aniline, ethyl acrylate and Triton B. Oil, $R_f$ value: 0.60 (silica gel; methylene chloride/methanol=9:1)

(2) N-[4-[[4-(4-(1-Benzyl)piperidinyl)piperazin-1-yl)carbonyl]phenyl]-β-alanine ethyl ester dihydrochloride Prepared from 4-[[4-(4-(1-benzyl)piperidinylpiperazin-1-yl)carbonyl]aniline and ethyl acrylate and Triton B. Amorphous solid.

$R_f$ value: 0.35 (silica gel; methylene chloride/methanol/ concentrated ammonia=9:1:0.1)

EXAMPLE 9

Methyl [4-[4-[4-(1-tert-butyloxycarbonyl) piperidinyl]-piperazin-1-yl]acetyl]phenoxyacetate A solution of 1.3 g (0.0048 mol) of α-bromo-4-methoxycarbonylmethyloxyacetophenone, 1.3 g (0.0048 mol) of N-[4-(1-tert-butyloxycarbonyl)piperidinyl]piperazine and 0.62 g (0.0048 mol) of N-ethyldiisopropylamine (0.82 ml) in 50 ml of methylene chloride is left to stand overnight at room temperature. It is then concentrated to dryness in vacuo and the residue which remains is partitioned between ethyl acetate and water. The combined organic extracts are dried and concentrated to dryness in vacuo. The residue which remains is purified on a silica gel column (eluting agent: methylene chloride which contains 3% of methanol). The eluates containing substance are evaporated. The residue is dissolved in a little methanol and this solution is acidified to pH 6 with ethereal hydrochloric acid and evaporated. The residue is triturated with acetone, filtered off with suction and dried.

Yield: 350 mg of a colourless solid (15.3% of theory), Mass spectrum: M⁺=475; $R_f$ value: 0.60 (silica gel; methylene chloride/methanol=9:1)

The following compound can be prepared analogously to Example 9:
(1) [4-[4-[4-(1-tert-Butyloxycarbonyl)piperidinyl)-piperazin-1-yl]acetyl]-phenylacetic acid Prepared from N-[4-(1-tert-butyloxycarbonyl) piperidinyl)-piperazine and methyl 4-(α-bromoacetyl) phenylacetate.

EXAMPLE 10

Methyl [3-[4-[4-(1-tert-butyloxycarbonyl) piperidinyl]-piperazin-1-yl]acetyl]phenoxyacetate A solution of 2 g (0.011 mol) of 3-methoxycarbonylmethyloxy-aniline in 20 ml of absolute tetrahydrofuran is added dropwise to a solution of 1.8 g (0.011 mol) of 1,1'-carbonyldi(1,2,4-triazole) in 50 ml of absolute tetrahydrofuran, which is cooled to −5° C., while stirring. The mixture is stirred at −5° C. for a further half an hour and then at room temperature for 1 hour, a solution of 2.95 g (0.011 mol) of N-[4-(1-tert-butyloxycarbonyl) piperidinyl]piperazine in 20 ml of tetrahydrofuran is then added and the mixture is subsequently heated at the reflux temperature for 2.5 hours. After the mixture has been stirred overnight at room temperature it is concentrated in vacuo and the residue is partitioned between ethyl acetate and water. The organic phase is separated off, dried and concentrated. The residue obtained is purified on a silica gel column, methylene chloride which contains 2.5% of methanol being used as eluting agent.

Yield: 1.8 g (34.2% of theory), Mass spectrum: M⁺=476; $R_f$ value: 0.50 (silica gel; methylene chloride/methanol=9:1)

The following compounds can be prepared analogously to Example 10:
(1) Methyl [3-[4-(4-(1-tert-butyloxycarbonyl)-piperidinyl)-piperazin-1-yl]carbonylamino]phenyl-propionate Prepared from methyl 3-[4-aminophenyl]propionate hydrochloride, N-[4-(1-tert-butyloxycarbonyl)piperidinyl]-piperazine, N-ethyldiisopropylamine and 1,1-carbonyldi-(1, 2,4-triazole).

(2) tert-Butyl [4-[[4-(4-(1-benzyl)piperidinyl)-piperazin-1-yl]carbonylamino]phenoxyacetate Prepared from N-(4-(1-benzyl)piperidinyl)piperazine, 4-tert-butyloxycarbonylmethyloxyaniline, 1,1-carbonyldi(1, 2,4-triazole) and triethylamine.

Melting point: 295–298° C. (decomposition); $R_f$ value: 0.43 (silica gel; methylene chloride/methanol=9:1)

(3) Dimethyl [3,4-[[4-[4-(1-tert-butyloxycarbonyl)-piperidinyl)piperazin-1-yl)carbonylamino]-phenylenedioxy]-diacetate Prepared from dimethyl 4-amino-1,2-phenylenedioxy-diacetate hydrochloride, N-[4-(1-tert-butyloxycarbonyl)-piperidinyl]piperazine, N-ethyl-diisopropylamine and 1,1-carbonyldi(1,2,4-triazole). Oil $R_f$ value: 0.38 (silica gel; methylene chloride/methanol= 9:1)

(4) Ethyl 3-[4-[[4-(1-tert-butyloxycarbonyl)piperidin-yl)-piperazin-1-yl)carbonylamino]phenoxy]propionate Prepared from ethyl 3-(4-aminophenoxy)propionate hydrochloride, N-[4-(1-tert-butyloxycarbonyl)piperidinyl]-piperazine, triethylamine and 1,1-carbonyldi(1,2,4-triazole).

Melting point: 86–88° C., $R_f$ value: 0.35 (silica gel; methylene chloride/methanol=9:1)

(5) Ethyl 4-[[4-[4-(1-tert-butyloxycarbonyl)-piperidinyl)-piperazin-1-yl)carbonylaminolphenylacetate Prepared from N-[4-(1-tert-butyloxycarbonyl) piperidinyl]-piperazine, ethyl 4-aminophenylacetate hydrochloride, triethylamine and 1,1-carbonyldi(1,2,4-triazole).

(6) Methyl [4-trans-[4-[4-(1-tert-butyloxycarbonyl)-piperidinyl)piperazin-1-yl)carbonylaminocyclohexyl] acetate Prepared from methyl trans-4-aminocyclohexylacetate hydrochloride, N-[4-(1-tert-butyloxycarbonyl)piperidinyl]-piperazine, triethylamine and 1,1-carbonyldi(1,2,4-triazole).
(7) tert-Butyl [4-trans-[4-(4-(1-benzyl)piperidinyl)-piperazin-1-yl)carbonylaminocyclohexyloxy]acetate Prepared from tert-butyl trans-4-aminocyclohexylacetate, 4-(1-benzyl)piperidinyl]piperazine dihydrochloride, N-ethyldiisopropylamine and 1,1-carbonyldi(1,2,4-triazole).

Melting point: 110–120° C.; $R_f$ value: 0.15 (silica gel; methylene chloride/methanol=9:1)

(8) Methyl N-[[4-(4-(1-tert-butyloxycarbonyl)-piperidinyl]-piperazin-1-yl]carbonyl]-4-piperidinyloxyacetate Prepared from N-[4-(1-tert-butyloxycarbonyl) piperidinyl]-piperazine hydrochloride, methyl 4-piperidinyloxyacetate hydrochloride, triethylamine and 1,1-carbonyldi(1,2,4-triazole).

(9) N-[4-[4-(4-(1-tert-Butyloxycarbonyl)piperidinyl]-piperazin-1-yl]carbonylamnophenyl]glycine methyl ester Prepared from N-(1-tert-butyloxycarbonyl) piperidinyl]-piperazine hydrochloride, N-4-aminophenyl-glycine methyl ester, triethylamine and 1,1-carbonyldi(1,2,4-triazole).

(10) tert-Butyl [4-[[[-4-[1-(tert-butyloxycarbonyl)piperidin-4-yl]piperazin-1-yl]carbonyl]aminomethyl]piperidin-1-yl]-acetate Melting point: 131–133° C.; $R_f$ value: 0.48 (silica gel; methylene chloride/methanol/concentrated ammonia= 9:1:0.1)

(11) Ethyl 1-[2-[[4-[1-(tert-butyloxycarbonyl)piperidin-4-yl]-piperazin-1-yl]carbonylamino]ethyl]piperidine-4-carboxylate Mass spectrum: $(M+H)^+=496$; $R_f$ value: 0.32 (silica gel; methylene chloride/methanol/concentrated ammonia= 9:1:0.1)

EXAMPLE 11

(R)-sec-Butyl [4-[[4-(4-piperidinyl)piperazin-1-yl] carbonylamino]phenoxy]acetate dihydrochloride A suspension of 0.5 g (13 mmol) of [4-[[4-(4-piperidinyl)-piperazin-1-yl]carbonylamino]phenoxy]acetic acid dihydrochloride and 10 ml of thionyl chloride is stirred at room temperature for 2 hours and is then heated at the reflux temperature for a further 2 hours. The excess thionyl chloride is then distilled off under reduced pressure and the residue is suspended in 40 ml of methylene chloride. 1 ml of R-butan-2-ol is added and the mixture is heated at the reflux temperature for 6 hours. After the solvent has been distilled off, the residue is triturated in acetone and filtered off with suction. The solid substance thus obtained is purified by means of chromatography over silica gel, methylene chloride/methanol/ concentrated ammonia=2:1:0.25 being used as the eluting agent. The solid obtained after evaporation is dissolved in methylene chloride and converted into the dihydrochloride with ethereal hydrochloric acid and, after renewed evaporation, the residue is triturated with ether.

Yield: 120 mg (21% of theory), Melting point: 294–296° C. (decomposition); Mass spectrum: $(M+H)^+=419$; $R_f$ value: 0.40 (silica gel; methylene chloride/methanol/concentrated ammonia=2:1:0.25)

The following compound is prepared analogously to Example 11:

(1) (S)-sec-Butyl [4-[[4-(4-piperidinyl)piperazin-1-yl] carbonylamino]phenoxy]acetate dihydrochloride Prepared from [4-[[4-(4-piperidinyl)piperazin-1-yl] carbonyl-amino]phenoxy]acetic acid dihydrochloride, thionyl chloride and (S)-butan-2-ol. Amorphous solid Mass spectrum: $(M+H)^+=419$; $R_f$ value: 0.40 (silica gel; methylene chloride/methanol/concentrated ammonia= 2:1:0.25)

EXAMPLE 12

4-[2-[4-(4-Piperidinyl)piperazin-1-yl]-2-hydroxyethyl]-phenoxyacetic acid dihydrochloride 8.5 mg (0.22 mmol) of sodium borohydride are added to a solution of 100 mg (0.22 mmol) of 4-[[4-(4-piperidinyl)-piperazin-1yl]acetyl]phenoxyacetic acid trihydrochloride in 10 ml of methanol and the mixture is stirred overnight. 2 ml of a 0.1N hydrochloric acid are then added and the solution is concentrated to dryness under reduced pressure. The residue is partitioned between saturated sodium chloride solution and ethyl acetate and, after drying over sodium sulphate, the organic phase is concentrated to dryness. Mass spectrum: $(M+H)^+=364$;

EXAMPLE 13

Methyl [4-trans-[2S(4-(4-tert-butyloxycarbonyl) piperidinyl)-piperazin-1-yl]-propionylamino] cyclohexanecarboxylate 0.3 g of sodium cyanoborohydride is added to a solution of 0.7 g (0.0026 mol) of methyl 4-trans-[2S-(4-piperazinyl) propionylamino]cyclohexanecarboxylate, 0.53 g (0.0026 mmol) of N-tert-butyloxycarbonylpiperazin-4-one and 0.9 ml (0.0029 mol) of titanium(IV) isopropylate in 20 ml of absolute ethanol at room temperature, while stirring, and stirring is continued overnight. The mixture is then concentrated to dryness under reduced pressure and the residue is partitioned between water and ethyl acetate. The organic phase is dried and concentrated and the residue is purified by chromatography over silica gel, methylene chloride which contains 2% and 4% of methanol being used as the eluting agent.

Yield: 0.73 g (58% of theory), $R_f$ value: 0.65 (silica gel; methylene chloride/methanol=9:1)

The following compounds can be prepared analogously to Example 13:

(1) Methyl [4-trans-[2S-(4-(4-(1-tert-butyloxycarbonyl)-piperidinyl)piperazin-1-yl)]-(3-(4-methoxyphenyl)) propionyl-amino]cyclohexanecarboxylate Prepared from methyl 4-trans-[2S-4-piperazinyl)-(3-(4-methoxyphenyl)) propionylamino]cyclohexanecarboxylate and N-tert-butyloxycarbonylpiperidin-4-one. $R_f$ value: 0.42 (silica gel; methylene chloride/methanol/concentrated ammonia=9:1:0.1)

(2) Methyl N-[[2S-(4-(4-(1-tert-butyloxycarbonyl)-piperidinyl)piperazin-1-yl)]propionyl]-4-piperidinyloxyacetate Prepared from methyl N-[2S-(4-piperazinyl)propionyl]-4-piperidinyloxyacetate and N-tert-butyloxycarbonyl-piperidin-4-one.

(3) Ethyl N-[[2S-(4-(4-(1-tert-butyloxycarbonyl) piperidinyl)-piperazin-1-yl)]-(3-(4-methoxyphenyl)) propionyl]-4-piperidinyloxyacetate Prepared from ethyl N-[2S-(4-piperazinyl)-(3-(4-methoxyphenyl))propionyl]-4-piperidinyloxyacetate and N-tert-butyloxycarbonylpiperidin-4-one.

$R_f$ value: 0.60 (silica gel; methylene chloride/methanol/ concentrated ammonia=9:1:0.1)

EXAMPLE 14

Methyl [4-[[4-(4-(1-tert-butyloxycarbonyl) piperidinyl)-piperazin-1-yl)]-2-ethyl]phenoxy] acetate A solution of equimolar amounts of [4-(1-tert-butyloxycarbonyl) piperidinyl]piperazine and 2-(4-methoxycarbonyl-methyloxyphenyl)ethyl iodide and 2 equivalents of N-ethyldiisopropylamine in dimethylformamide is left to stand at room temperature for 1 day. The solution is then concentrated to dryness under reduced pressure and the residue is purified by means of column

EXAMPLE 15

N-Benzyl-N-[4-trans-[4-(4-(1-tert-butyloxycarbonyl)-piperidinyl) piperazin-1-yl)]carbonylaminocyclohexyl]glycine A solution of 21 g (4.2 mmol) of N-[4-trans-[4-(1-tert-butyloxycarbonyl)piperidinyl) piperazin-1-yl)]carbonylaminocyclohexyl]benzylamine and 0.8 g (8.4 mmol) of glyoxylic acid hydrate in 100 ml of methanol is hydrogenated exhaustively over 0.4 g of Raney nickel at 50° C. under a hydrogen pressure of 50 psi. After the catalyst has been filtered off with suction, the filtrate is concentrated to dryness under reduced pressure. The residue is purified by means of column chromatography over silica gel, methylene chloride/methanol/concentrated ammonia 9:1:0.1 being used as the eluting agent.

Yield: 450 mg (20.4% of theory), $R_f$ value: 0.45 (silica gel; methylene chloride/methanol/concentrated ammonia= 4:1:0.2)

EXAMPLE 16

N-[4-[4-(4-(1-tert-Butyloxycarbonyl)-piperidinyl)-piperazin-1-yl]-carbonylaminophenyl]sarcosine methyl ester Prepared from N-[4-[4-(4-(1-tert-butyloxycarbonyl)-pipe-ridinyl)-piperazin-1-yl]carbonylaminophenyl]glycine methyl ester, paraformaldehyde and sodium cyanoborohydride analogously to Example VIIa.

The following compound can be prepared analogously to Example 16:
(1) N-Benzyl-N-[4-[4-(4-(1-tert-butyloxycarbonyl)-piperidinyl)-piperazin-1-yl)]carbonylaminophenyl]-glycine methyl ester Prepared from N-[4-[4-(4-(1-tert-butyloxycarbonyl)-piperidinyl)-piperazin-1-yl)]carbonylaminophenyl]-glycine methyl ester, benzaldehyde and sodium cyanoborohydride analogously to Example VIIa.

EXAMPLE 17

[4-[[4-(4-Piperidinyl)-piperazin-1-yl]-carbonylamino]phenoxy]-acetic acid 30 g (0.0553 mol) of benzyl [4-[[4-(1-benzyl) piperidinyl)-piperazin-1-yl]-carbonylamino]phenoxy]-acetate are dissolved in 300 ml of methanol and hydrogenated with hydrogen in the presence of 6 g of palladium/charcoal (10%) at room temperature under 5 bar. After uptake of 1 mol of hydrogen, the hydrogenation is interrupted briefly in order to add 810 ml of water. The hydrogenation is then continued for about 1.5 hours, until the theoretical amount of hydrogen has been taken up. Thereafter, the catalyst is filtered off with suction and the filtrate is concentrated to dryness in vacuo. The residue is suspended in acetone (about 500 ml) and filtered off with suction. The product is suspended in 300 ml of methanol and the suspension is boiled up briefly and then filtered hot with suction. 19.5 g (97.3%) of the desired product are obtained, and the product is dried at 90° C. in a vacuum drying cabinet for 15 hours in order to free it from residual solvent.

Melting point: 313–315° C. (decomposition); Mass spectrum: $M^+$=362;

EXAMPLE 18

Methyl 3-[4-[4-(4-(1-benzyl)-piperidinyl)-piperazin-1-yl]carbonyl-piperidinyl]propionate dihydrochloride A solution of 0.7 g (0.0018 mol) of methyl 3-[4-[4-(4-pyridyl)-piperazin-1-yl]carbonylpiperidinyl]propionate hydrochloride, 0.21 ml (0.0018 mol) of benzyl bromide and 0.3 ml of N-ethyl-diisopropylamine in 30 ml of acetonitrile is heated at the reflux temperature for 2 hours. The solution is concentrated to dryness in vacuo and the residue is dissolved in 30 ml of methanol. 1 g of sodium borohydride is added to the solution and the mixture is stirred at room temperature for 48 hours. Thereafter, another 0.6 g of sodium borohydride is added and the mixture is stirred overnight. It is concentrated to dryness in vacuo and the residue is partitioned between ethyl acetate and water. The ethyl acetate phase is separated off, dried and concentrated. The residue which remains is purified over a silica gel column, methylene chloride with 5% of methanol being used as the eluting agent. After evaporation of the eluates, a residue is obtained, which is taken up in methanol, and the solution is acidified with ethereal hydrochloric acid. After evaporation, a colourless foam remains.

Yield: 0.3 g (36.6% of theory), Mass spectrum: $M^+$=456; $R_f$ value: 0.37 (silica gel; methylene chloride/methanol=9:1)

EXAMPLE 19

Pivaloyloxymethyl [4-[[4-(4-(1-benzyl)-piperidinyl)-piperazin-1-yl]carbonylamino]phenoxy]acetate A mixture of equimolar parts of [4-[[4-(4-(1-benzyl)-piperidinyl)-piperazin-1-yl]carbonylamino]phenoxy]acetic acid, chloromethyl pivalate, potassium iodide and potassium carbonate is stirred in dimethylformamide at room temperature for 2 days. It is then poured into water and extracted with ethyl acetate. The combined organic phases are dried and concentrated to dryness in vacuo. The residue which remains is purified by means of chromatography over a silica gel column.

The following compound can be prepared analogously to Example 19:
(1) (1-Ethoxy)-carbonyloxyethyl [4-[[4-(4-(1-benzyl)-piperidinyl)-piperazin-1-yl]-carbonylamino]phenoxy]-acetate Prepared from [4-[[4-(4-(1-benzyl)-piperidinyl)-piperazin-1-yl]carbonylamino]phenoxy]acetic acid and 1-chloroethyl ethyl carbonate.

EXAMPLE 20 tert-Butyl 3-[4-trans-[[4-(4-(1-benzyl)-piperidinyl)-piperazin-1-yl]-carbonylamino]cyclohexyl] propionate 0.8 g (4 mmol) of N,N-dimethylformamide di-tert-butyl acetal is added dropwise to a suspension of 0.45 g (1 mmol) of 3-[4-trans-[[4-(4-(1-benzyl)-piperidinyl)-piperazin-1-yl]-carbonylamino]cyclohexyl]propionic acid in 6 ml of toluene at 80° C., while stirring, and the mixture is heated at 80° C. for a further hour. Another 0.8 ml of N,N-dimethylformamide di-tert-butyl acetal is then added and the mixture is heated at 80° C. for a further hour. It is concentrated to dryness under reduced pressure and the solid which remains is purified by chromatography over silica gel, methylene chloride/methanol/concentrated ammonia= 95:5:0.5 being used as the eluting agent.

chromatography over silica gel. $R_f$ value: 0.55 (silica gel; methylene chloride/methanol/concentrated ammonia= 9:1:0.1)

EXAMPLE 21

Benzyl [4-[[4-(4-(1-benzyl)-piperidinyl)-piperazin-1-yl]-carbonylamino]phenoxy]acetate 57.4 g (0.172 mol) of 1-(4-(1-benzyl)-piperidinyl)-piperazine×2 HCl are taken up in 500 ml of a saturated sodium carbonate solution and the mixture is then extracted 5× with 200 ml of methylene chloride each time. The combined organic phases are dried over sodium sulphate and concentrated. The residue is dissolved in 200 ml of dioxane and the solution is added dropwise to a solution of 44 g (0.155 mol) of benzyl 2-(4-isocyanato-phenoxy)-acetate in 100 ml of dioxane at room temperature, while stirring vigorously. When the addition has ended, the reaction solution is subsequently stirred at 60° C. (oil bath temperature) for a further 3 hours and then at room temperature overnight. The solvent is distilled off in vacuo and the residue is stirred with ether. The undissolved material is filtered off with suction and dried.

Yield: 72.0 g (85.4% of theory), Mass spectrum: M$^+$=542

The following compound can be prepared analogously to Example 21:
(1) Ethyl [4-[[4-(1-benzyl-3-pyrrolidinyl)-piperazin-1-yl]-carbonylamino]-phenoxy]-acetate Instead of benzyl 2-(4-isocyanato-phenoxy)-acetate, the corresponding ethyl ester is employed. The crude product is chromatographed over silica gel.

Mass spectrum: (M+H)$^+$=467; R$_f$ value: 0.48 (silica gel; methylene chloride/methanol/concentrated ammonia=9:1:0.1)

EXAMPLE 22

[4-[[4-(1-Benzyl-3-pyrrolidinyl)-piperazin-1-yl]-carbonylamino]-phenoxy]-acetic acid Methanol is added to an emulsion of 300 mg of ethyl [4-[[4-(1-benzyl-3-pyrrolidinyl)-piperazin-1-yl]-carbonylamino]-phenoxy]-acetate in 10 ml of tetrahydrofuran and 2.5 ml of 1M sodium hydroxide solution in an amount such that a clear solution forms. The solution is stirred at room temperature for 2 hours, 2.5 ml of 1M hydrochloric acid are added and the solvent is evaporated off under reduced pressure. The residue is triturated with a mixture of anhydrous ethanol/methylene chloride and filtered. The filtrate is evaporated and the residue is dried.

Yield: 280 mg (99% of theory), Mass spectrum: (M+H)$^+$=439; R$_f$ value: 0.18 (silica gel; methylene chloride/methanol/concentrated ammonia=4:1:0.25)

The following compounds are obtained analogously to Example 22:
(1) [4-[[4-(3-Pyrrolidinyl)-piperazin-1-yl]-carbonylamino]phenoxy]acetic acid The residue is triturated with a mixture of anhydrous methanol/methylene chloride.

Mass spectrum: (M+H)$^+$=349; R$_f$ value: 0.11 (silica gel; methylene chloride/methanol/concentrated ammonia=2:1:0.25)

(2) [4-[[4-(1-Methyl-3-pyrrolidinyl)-piperazin-1-yl]-carbonylamino]phenoxy]acetic acid The residue is triturated with a mixture of anhydrous methanol/methylene chloride.

Mass spectrum: (M+H)$^+$=363; R$_f$ value: 0.30 (silica gel; methylene chloride/methanol/concentrated ammonia=2:1:0.25)

(3) [4-[2-[[4-(1-Benzyl-piperidin-4-yl)-piperazin-1-yl]-carbonyl]-ethyl]-piperidin-1-yl]-acetic acid The reaction solution is acidified with 1M hydrochloric acid and the solvent is evaporated off under reduced pressure. The residue is chromatographed over silica gel with methylene chloride/methanol/concentrated ammonia (4:1:0.25).

Mass spectrum: M$^+$=456; R$_f$ value: 0.30 (silica gel; methylene chloride/methanol/concentrated ammonia=4:1:0.25)

(4) [4-[2-)[[4-(1-Methyl-piperidin-4-yl)-piperazin-1-yl]-carbonyl]-ethyl]-piperidin-1-yl]-acetic acid Mass spectrum: (M+H)$^+$=381; R$_f$ value: 0.31 (silica gel; methylene chloride/methanol/concentrated ammonia=2:1:0.25)

(5) [4-[2-[[4-(1-Benzyl-pyrrolidin-3-yl)-piperazin-1-yl]-carbonyl]-ethyl]-piperidin-1yl]-acetic acid The reaction solution is extracted with ether and the aqueous phase is evaporated. The residue is triturated with absolute ethanol/methylene chloride, the suspension is filtered and the filtrate is evaporated on a rotary evaporator. The residue is triturated with ether and filtered off with suction.

Mass spectrum: M$^+$=442; R$_f$ value: 0.30 (silica gel; methylene chloride/methanol/concentrated ammonia 4:1:0.25)

(6) [4-[2-[[4-(Pyrrolidin-3-yl)-piperazin-1-yl]-carbonyl]-ethyl]-piperidin-1-yl]-acetic acid The reaction solution is extracted with ether and the aqueous phase is evaporated. The residue is triturated with absolute ethanol/methylene chloride, the suspension is filtered and the filtrate is evaporated on a rotary evaporator. The residue is triturated with ether and filtered off with suction.

Mass spectrum: (M+H)$^+$=353; R$_f$ value: 0.12 (silica gel; methylene chloride/methanol/concentrated ammonia=2:1:0.25)

(7) [4-[2-[[4-(1-Methyl-pyrrolidin-3-yl)-piperazin-1-yl]-carbonyl]-ethyl]-piperidin-1-yl]-acetic acid The reaction solution is diluted with water and extracted with ether and the aqueous phase is evaporated. The residue is triturated with absolute ethanol/methylene chloride and filtered off with suction.

Mass spectrum: M$^+$=366; R$_f$ value: 0.12 (silica gel; methylene chloride/methanol/concentrated ammonia=4:1:0.25)

(8) [4-[[[4-(piperidin-4-yl)-piperazin-1-yl]-carbonyl]-methyloxy]-piperidin-1-yl]-acetic acid Mass spectrum: M$^+$=369; R$_f$ value: 0.12 (silica gel; methylene chloride/methanol/concentrated ammonia=2:1:0.25)

EXAMPLE 23

Ethyl [4-[[4-(1-methyl-3-pyrrolidinyl)-piperazin-1-yl]-carbonylamino]-phenoxy]-acetate 320 mg of 37% strength formaline and 270 mg of sodium cyanoborohydride are added to a suspension of 700 mg of ethyl [4-[[4-(3-pyrrolidinyl)-piperazin-1-yl]-carbonylamino]-phenoxy]-acetate in 30 ml of ethanol. The mixture is acidified with ethereal hydrochloric acid and stirred at room temperature for 1 hour. The solvent is evaporated off and the residue is chromatographed over silica gel with methylene chloride/methanol/concentrated ammonia (9:1:0.1).

Yield: 250 mg (34% of theory), Mass spectrum: M$^+$=390; R$_f$ value: 0.54 (silica gel; methylene chloride/methanol/concentrated ammonia=4:1:0.25)

The following compound is obtained analogously to Example 23:
(1) Cyclohexyl [4-[2-[[4-(1-methyl-pyrrolidin-3-yl)-piperazin-1-yl]-carbonyl]-ethyl]-piperidin-1-yl]-acetate Mass spectrum: M$^+$=448; R$_f$ value: 0.26 (silica gel; methylene chloride/methanol/concentrated ammonia=9:1:0.1)

---

Yield: 0.5 g (49.5% of theory), R$_f$ value: 0.50 (silica gel; methylene chloride/methanol/concentrated ammonia=9:1:0.1)

EXAMPLE 24

3-[[4-[[4-(1-Benzyl-piperidin-4-yl)-piperazin-1-yl]-carbonyl]-piperidin-1-yl]-carbonyl]-propionic acid A solution of 120 mg of ethyl 3-[[4-[[4-(1-benzyl-piperidin-4-yl)-piperazin-1-yl]-carbonyl]-piperidin-1-yl]-carbonyl]-propionate and 42 mg of lithium hydroxide hydrate in a mixture of 4 ml of tetrahydrofuran and 5 ml of water is stirred at room temperature for 4 hours. It is neutralized with 1N hydrochloric acid and the solvent is evaporated off under reduced pressure. The residue is chromatographed over silica gel with methylene chloride/methanol/concentrated ammonia (4:1:0.2).

Yield: 70 mg (52% of theory), Mass spectrum: $(M+H)^+=471$; $R_f$ value: 0.23 (silica gel; methylene chloride/methanol/concentrated ammonia=4:1:0.2)

The following compounds are obtained analogously to Example 24:

(1) [4-[2-[[4-(Piperidin-4-yl)-piperazin-1-yl]-carbonyl]-ethyl]-piperidin-1-yl]-acetic acid trihydrochloride The reaction solution is acidified with 1M hydrochloric acid and the solvent is evaporated off under reduced pressure. The residue is triturated with acetone several times and dried.

Mass spectrum: $(M+H)^+=367$; $R_f$ value: 0.06 (silica gel; methylene chloride/methanol/concentrated ammonia=2:1:0.2)

(2) 4-[4-[[4-(Piperidin-4-yl)-piperazin-1-yl]-carbonyl]-piperidin-1-yl]-butyric acid trihydrochloride The reaction solution is acidified with 1M hydrochloric acid and the solvent is evaporated off under reduced pressure. The residue is triturated with acetone several times and dried.

Mass spectrum: $(M+H)^+=367$; $R_f$ value: 0.46 (silica gel; methylene chloride/methanol/concentrated ammonia=1:3:0.2)

(3) [trans-4-[[4-(Piperidin-4-yl)-piperazin-1-yl]-carbonyl]-cyclohexylcarbonylamino]-acetic acid Melting point: 260–270° C. (sintering); Mass spectrum: $M^+=380$; $R_f$ value: 0.08 (silica gel; methylene chloride/methanol/concentrated ammonia=2:1:0.2)

(4) 3-[[4-[[4-(Piperidin-4-yl)-piperazin-1-yl]-carbonyl]-piperidin-1-yl]-carbonyl]-propionic acid Mass spectrum: $(M+H)^+=381$; $R_f$ value: 0.05 (silica gel; methylene chloride/methanol/concentrated ammonia=3:1:0.2)

(5) 1-[2-[[4-(Piperidin-4-yl)-piperazin-1-yl]-carbonylamino]-ethyl]-piperidine-4-carboxylic acid Melting point: 239–244° C. (decomposition); Mass spectrum: $M^+=367$; $R_f$ value: 0.33 (silica gel; methylene chloride/methanol/concentrated ammonia=2:1:0.2)

EXAMPLE 25

Dry ampoule with 2.5 mg of active compound per 1 ml
Composition:

| | |
|---|---|
| Active compound | 2.5 mg |
| Mannitol | 50.0 mg |
| Water for injection to | 1.0 ml |

Preparation:

The active compound and mannitol are dissolved in water. After filling the ampoules, the solution is freeze dried. Dissolving to give the ready-to-use solution is carried out with water for injection.

EXAMPLE 26

Dry ampoule with 35 mg of active compound per 2 ml
Composition:

| | |
|---|---|
| Active compound | 35.0 mg |
| Mannitol | 100.0 mg |
| Water for injection to | 2.0 ml |

Preparation:

The active compound and mannitol are dissolved in the water. After filling the ampoules, the solution is freeze dried. Dissolving to give the ready-to-use solution is carried out with water for injection.

EXAMPLE 27

Tablet with 50 mg of active compound
Composition:

| | |
|---|---|
| (1) Active compound | 50.0 mg |
| (2) Lactose | 98.0 mg |
| (3) Maize starch | 50.0 mg |
| (4) Polyvinylpyrrolidone | 15.0 mg |
| (5) Magnesium stearate | 2.0 mg |
| | 215.0 mg |

Preparation:

(1), (2) and (3) are mixed and the mixture is granulated with an aqueous solution of (4). (5) is admixed with the dried granules. Biplanar tablets faceted on both sides and with a dividing groove on one side are pressed from this mixture. Diameter of the tablets: 9 mm.

EXAMPLE 28

Tablet with 350 mg of active compound
Composition:

| | |
|---|---|
| (1) Active compound | 350.0 mg |
| (2) Lactose | 136.0 mg |
| (3) Maize starch | 80.0 mg |
| (4) Polyvinylpyrrolidone | 30.0 mg |
| (5) Magnesium stearate | 4.0 mg |
| | 600.0 mg |

Preparation:

(1), (2) and (3) are mixed and the mixture is granulated with an aqueous solution of (4). (5) is admixed with the dried granules. Biplanar tablets faceted on both sides and with a dividing groove on one side are pressed from this mixture. Diameter of the tablets: 12 mm.

EXAMPLE 29

Capsules with 50 mg of active compound
Composition:

| | |
|---|---|
| (1) Active compound | 50.0 mg |
| (2) Dried maize starch | 58.0 mg |
| (3) Powdered lactose | 50.0 mg |
| (4) Magnesium stearate | 2.0 mg |
| | 160.0 mg |

Preparation:

(1) is triturated with (3). This triturated mixture is added to the mixture of (2) and (4) with intensive mixing.

Hard gelatin capsules of size 3 are filled with this powder mixture on a capsule filling machine.

EXAMPLE 30

Capsules with 350 mg of active compound
Composition:

| | | |
|---|---|---|
| (1) | Active compound | 350.0 mg |
| (2) | Dried maize starch | 46.0 mg |
| (3) | Powdered lactose | 30.0 mg |
| (4) | Magnesium stearate | 4.0 mg |
| | | 430.0 mg |

Preparation:

(1) is triturated with (3). This triturated mixture is added to the mixture of (2) and (4) with intensive mixing.

Hard gelatin capsules of size 0 are filled with this powder mixture on a capsule filling machine.

We claim:

1. A piperazine derivative of formula

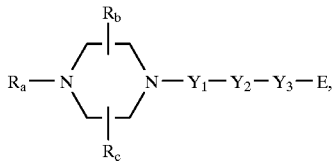

(I)

in which $R_a$ is a 3-piperidinyl or 4-piperidinyl group, wherein the hydrogen atom of a 3-piperidinyl or 4-piperidinyl group can be replaced by a $C_{1-4}$-alkoxycarbonyl or benzyloxycarbonyl group, or by a $C_{1-5}$-alkyl or phenyl-$C_{1-3}$-alkyl group, wherein each alkyl part can be substituted by a carboxyl, $C_{1-3}$-alkoxycarbonyl, aminocarbonyl, N-$C_{1-3}$-alkyl-aminocarbonyl or N,N-di-($C_{1-3}$-alkyl)-aminocarbonyl group or also, if the above-mentioned substituents are not on an a-carbon atom adjacent to a nitrogen atom, by a hydroxyl, $C_{1-3}$-alkoxy, amino, $C_{1-3}$-alkylamino or di-($C_{1-3}$-alkyl) amino group, $R_b$ and $R_c$, which can be identical or different, are hydrogen atoms or $C_{1-3}$-alkyl or phenyl-$C_{1-3}$-alkyl groups, $Y_1$ is —CO—

$Y_2$ is an —NH—B—group, where the carbonyl group of $Y_1$, is attached to the nitrogen atom of $Y_2$ and
B is a phenylene or cyclohexylene $Y_3$ is —O—CH$_2$—CO— and E is a —OH, $C_{1-6}$-alkoxy, or a $C_{5-7}$-cycloalkoxy group
or a tautomer thereof or a stereoisomer thereof or a mixture, or a salt thereof.

2. The piperazine derivative as recited in claim 1, in which $R_a$ is a 4-piperidinyl group, wherein the hydrogen atom of the imino group can be replaced by a $C_{1-5}$-alkyl or phenyl-$C_{1-3}$-alkyl group, by a $C_{1-4}$-alkoxycarbonyl or benzyloxycarbonyl group, $R_b$ and $R_c$, which can be identical or different, are hydrogen atoms or $C_{1-3}$-alkyl or phenyl-$C_{1-3}$-alkyl groups, $Y_1$ is —CO—, $Y_2$ is an —NH—B— group, where the carbonyl group of $Y_1$ is attached to the nitrogen atom of $Y_2$ and
B is a 1,3-phenylene, 1,4-phenylene or 1,4-cyclohexylene group, $Y_3$ is —O—CH$_2$—CO— and E is a —OH, $C_{1-6}$-alkoxy, or a $C_{5-7}$-cycloalkoxy group
or a tautomer thereof or a stereoisomer thereof or a mixture, or a salt thereof.

3. The piperazine derivative as recited in claim 1, in which $R_a$ is a 4-piperidinyl group, wherein the hydrogen atom of the imino group can be replaced by a $C_{1-3}$-alkyl, benzyl or tert-butyloxycarbonyl group, $R_b$ and $R_c$ in each case are a hydrogen atom, $Y_1$ is an —CO—, $Y_2$ is an —NH—B— group, where the carbonyl group of $Y_1$, is attached to the nitrogen atom of $Y_2$ and
B is a 1,3-phenylene, 1,4-phenylene or 1,4-cyclohexylene group, $Y_3$ is —O—CH$_2$—CO— and E is a —OH, $C_{1-6}$-alkoxy, or a $C_{5-7}$-cycloalkoxy group
or a tautomer thereof or a stereoisomer thereof or a mixture, or a salt thereof.

4. [4-[[4-(4-Piperidinyl)-piperazin-1-yl]carbonylamino] phenoxy]acetic acid, the butyl, isobutyl, cyclopentyl or a cyclohexyl ester thereof, or a tautomer thereof, or a stereo isomer thereof or a salt thereof.

5. The piperazine derivative as recited in claim 1, in which $R_a$ is a 4-piperidinyl group, $R_b$ and $R_c$ in each case are a hydrogen atom, $Y_1$ is —CO—, $Y_2$ is an —NH—B— group, where the carbonyl group of $Y_1$, is attached to the nitrogen atom of $Y_2$ and
B is a 1,4-phenylene or 1,4-cyclohexylene group, $Y_3$ is —O—CH$_2$—CO—, and E is a —OH, $C_{1-6}$-alkoxy, or a $C_{5-7}$-cycloalkoxy group
or a tautomer thereof or a stereoisomer thereof or a mixture, or a salt thereof.

6. A physiologically tolerated salt of the piperazine derivative as recited in claim 1, with an inorganic or organic acid or base.

* * * * *